US011198717B2

(12) United States Patent
Mendoza et al.

(10) Patent No.: US 11,198,717 B2
(45) Date of Patent: Dec. 14, 2021

(54) VARIANT TYPE III INTERFERONS AND SYNTHEKINES

(71) Applicant: The Board of Trustees of the Leland Stanford Junior University, Stanford, CA (US)

(72) Inventors: Juan Luis Mendoza, Redwood City, CA (US); Kenan Christopher Garcia, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/336,598

(22) PCT Filed: Sep. 29, 2017

(86) PCT No.: PCT/US2017/054498
§ 371 (c)(1),
(2) Date: Mar. 26, 2019

(87) PCT Pub. No.: WO2018/064574
PCT Pub. Date: Apr. 5, 2018

(65) Prior Publication Data
US 2019/0225665 A1    Jul. 25, 2019

Related U.S. Application Data

(60) Provisional application No. 62/402,204, filed on Sep. 30, 2016.

(51) Int. Cl.
*C07K 14/555* (2006.01)
*A61P 31/20* (2006.01)
*A61P 35/00* (2006.01)
*A61K 38/00* (2006.01)
*A61K 31/7088* (2006.01)

(52) U.S. Cl.
CPC ........ *C07K 14/555* (2013.01); *A61K 31/7088* (2013.01); *A61P 31/20* (2018.01); *A61P 35/00* (2018.01); *A61K 38/00* (2013.01)

(58) Field of Classification Search
None
See application file for complete search history.

(56) References Cited

U.S. PATENT DOCUMENTS 7,829,076 B2    11/2010  Sheppard et al.
2007/0041975 A1  2/2007  Brady et al.

2011/0008283 A1    1/2011  Artymiuk et al.
2012/0308517 A1   12/2012  Arregui et al.
2016/0228512 A1    8/2016  Kotenko et al.

FOREIGN PATENT DOCUMENTS

WO    WO2014074186    5/2014
WO    WO 2015103749   7/2015

OTHER PUBLICATIONS

Kolchanov, 1988, Journal of Molecular Evolution, vol. 27, pp. 154-162. (Year: 1988).*
Pasquo, 2012, PLoS ONE, vol. 7, Issue 2, e32555 (Year: 2012).*
Levin et al., "Multifaceted activities of type I interferon are revealed by a receptor antagonist," Science Signaling, May 27, 2014, pp. 1-30, vol. 7, Issue 327, American Association for the Advancement of Science, Washington, D.C.
Yu et al. "Design and evaluation of novel interferon lambda analogs with enhanced antiviral activity and improved drug attributes," Drug Design, Development and Therapy, Jan. 6, 2016, pp. 163-182, vol. 10, National Center for Biotechnology Information, Bethesda MD.
Levin et al. (2014) "Multifaceted activities of type I interferon are revealed by a receptor antagonist," Science Signaling, vol. 27 No. 7(327), pp. 1-30.
Yu et al. (2016) "Design and evaluation of novel interferon lambda analogs with enhanced antiviral activity and improved drug attributes," Drug Design, Development and Therapy,vol. 10, pp. 163-182.
Donnelly et al. (2010) "Interferon-Lambda: A New Addition to an Old Family" Journal of Interferon and Cytokine Research 30:8 555-564.
Mendoza et al. (2017) "The IFN-[lambda]-IFN-[lambda] R1-IL-10R[beta] Complex Reveals Structural Features Underlying Type III IFN Functional Plasticity" Immunity 46:3 379-392.
Moraga et al. (2017) "Synthekines are surrogate cytokine and growth factor agonists that compel signaling through non-natural receptor dimers" E-LIFE 1-22.
Ng et al. (2014) "Concise Review: Engineering the Fusion of Cytokines for the Modulation of Immune Cellular Responses in Cancer and Autoimmune Disorders: Fusion Cytokines for Use in Immunotherapy II" Stem Cells Translational Medicine 1:1 66-73.
Sommereyns et al. (2008) "IFN-Lambda (IFN-[lambda]) is Expressed in a Tissue-Dependent Fashion and Primarily Acts on Epithelial Cells In Vivo" PLOS Pathogens 4:3 e1000017.

* cited by examiner

*Primary Examiner* — Gary B Nickol
*Assistant Examiner* — Jegatheesan Seharaseyon
(74) *Attorney, Agent, or Firm* — Pamela J. Sherwood; Bozicevic, Field & Francis LLP

(57) ABSTRACT

Compositions and methods are provided relating to Type III interferons.

13 Claims, 16 Drawing Sheets
Specification includes a Sequence Listing.

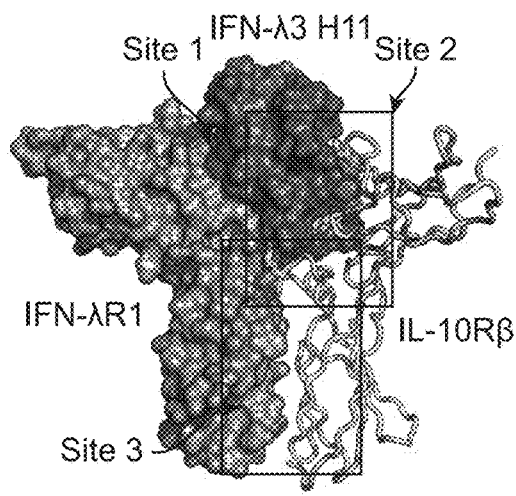
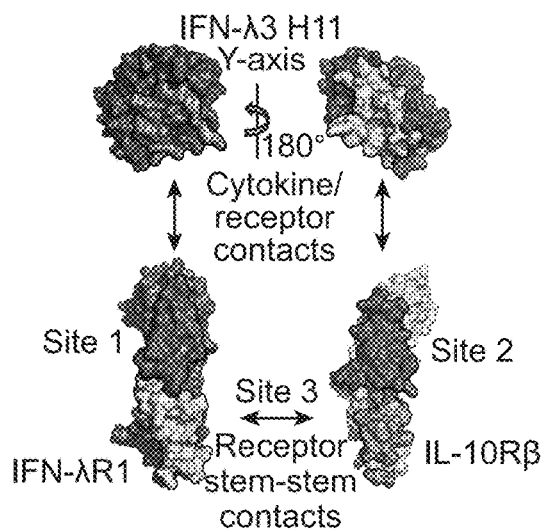
FIG. 3A
FIG. 3B
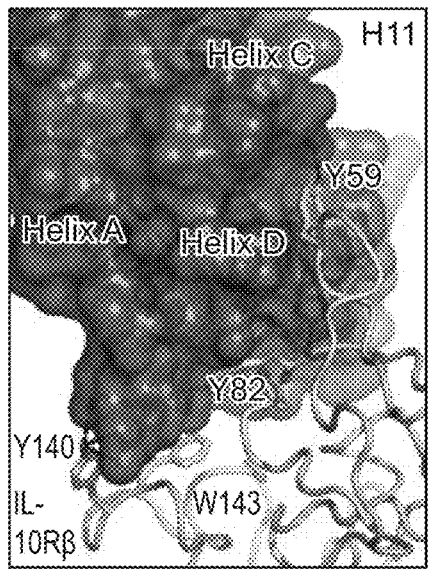
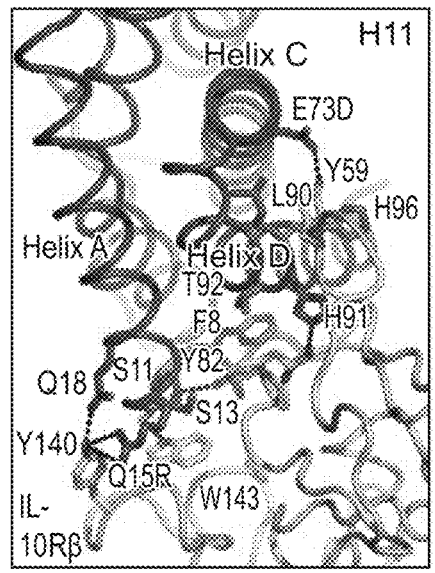
FIG. 3C
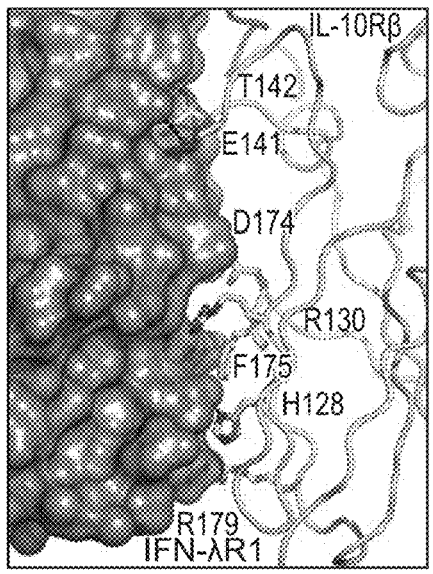
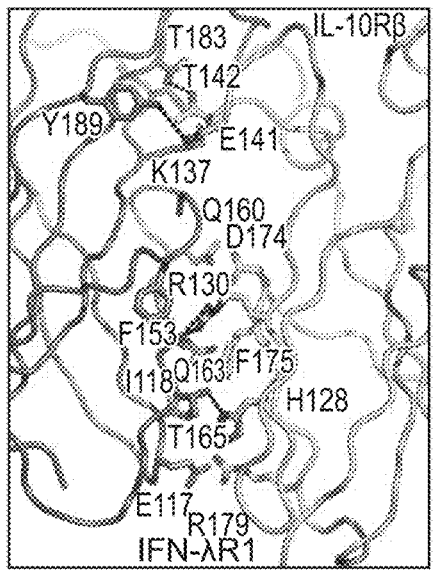
FIG. 3D

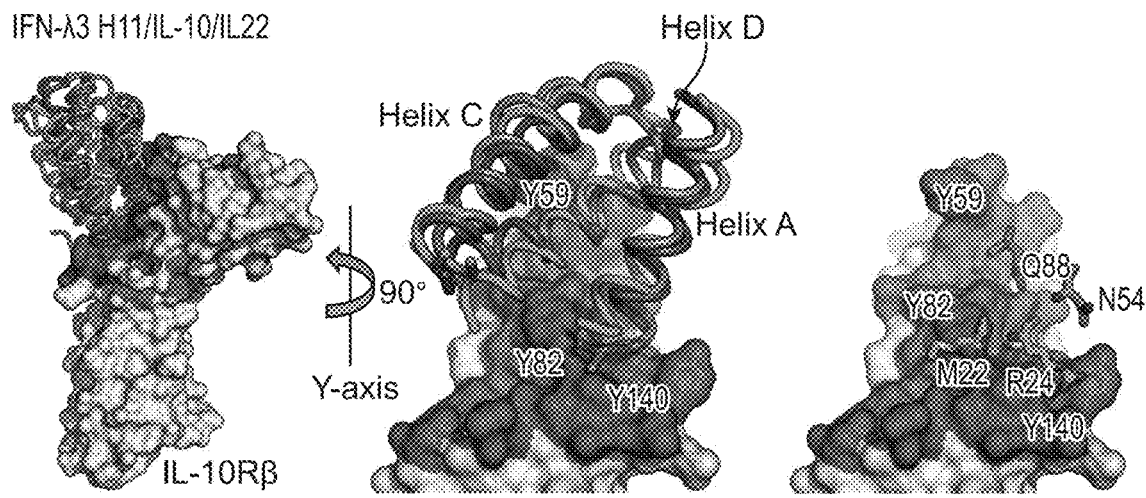
FIG. 4A
| ▓ IFN-λ3 H11 | ░ IL-10 | ▓ IL-22 |
Pre-Helix A
```
IL-10      14 HFPGNLPNM 22
IL-22      42 LD-KSNFQQ 49
IFN-λ3      6 IA-QFKSLS 34
IFN-λ3 H11
```
Helix C
```
IL-10      71 FYLEEVMPQAE  81
IL-22      98 FTLEEVLFPQS 108
IFN-λ3     67 LTL-KVLEATA  76
IFN-λ3 H11              D
```
Helix A
```
IL-10      24 RDLRDAFSR 32
IL-22      50 PYITNRTFM 58
IFN-λ3     14 PQELQAFKR 22
IFN-λ3 H11    R
```
Helix D
```
IL-10      88 IKAHVNSLGENLKTLRL 103
IL-22     112 FQPYMQEVVPFLARLSN 127
IFN-λ3     82 LGDVLDQPLHTLHHILS  97
IFN-λ3 H11
```
FIG. 4B
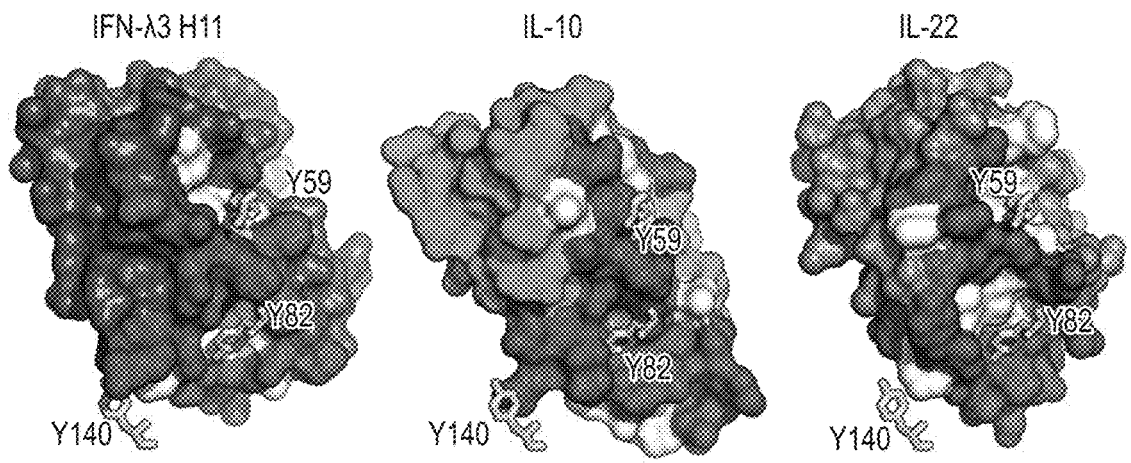
FIG. 4C

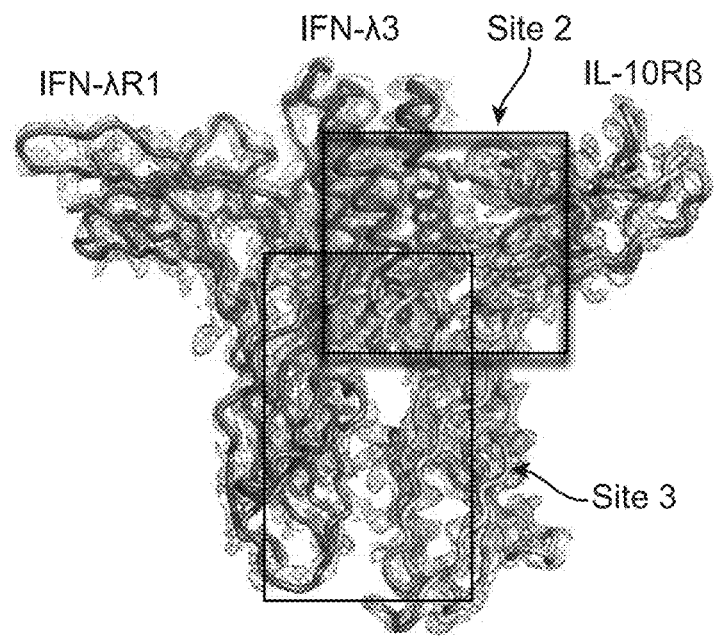
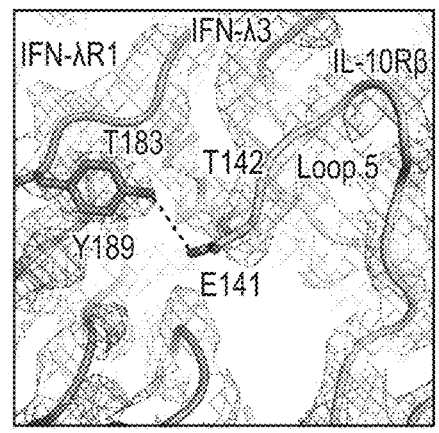
FIG. 8A
FIG. 8B
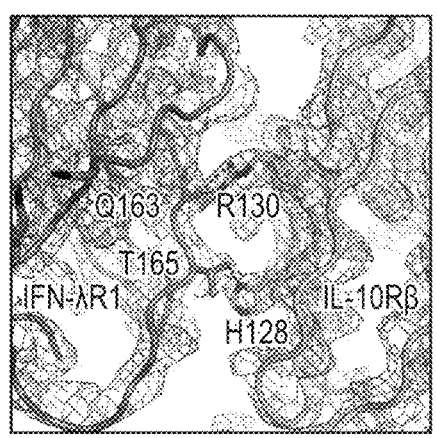
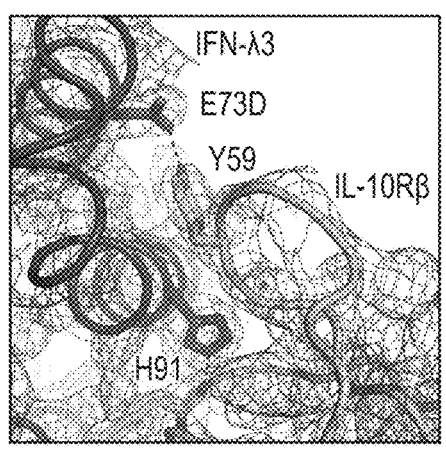
FIG. 8C
FIG. 8D
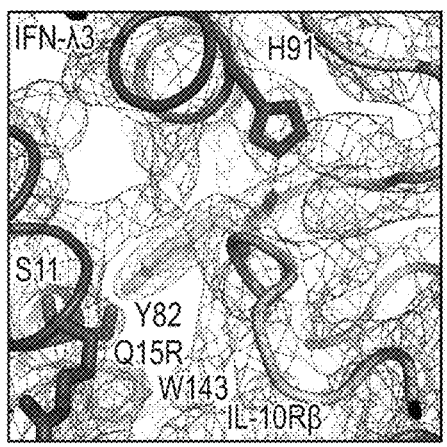
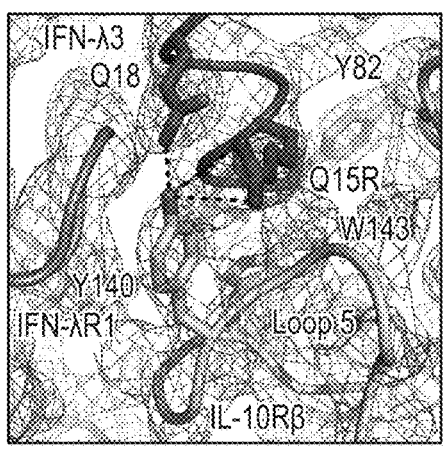
FIG. 8E
FIG. 8F

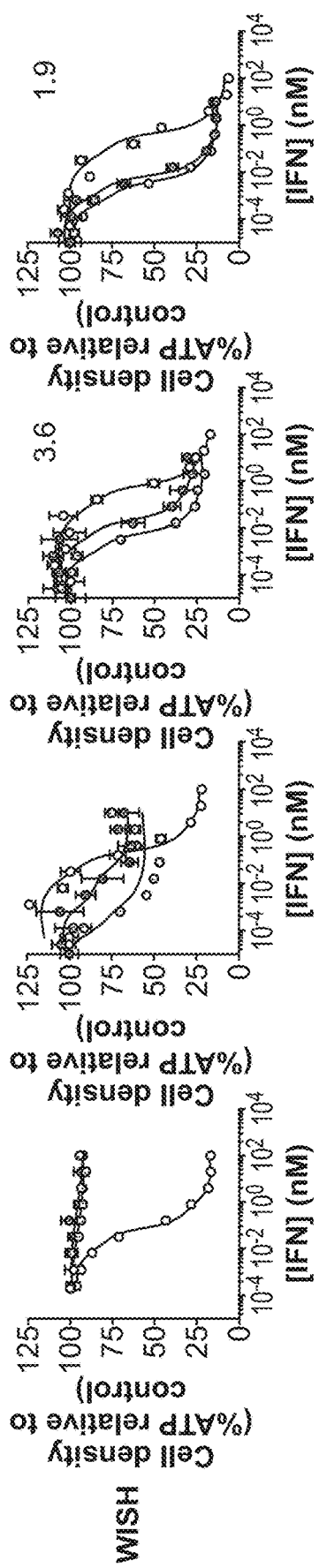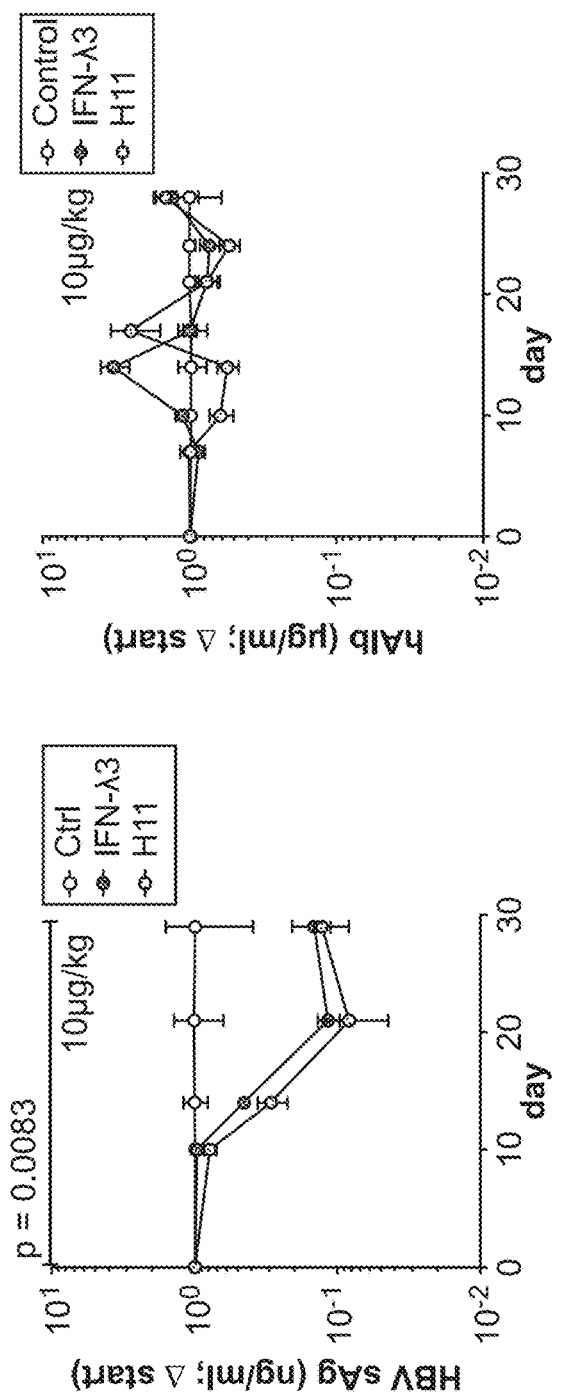
FIG. 10B (Cont.)
FIG. 10C
FIG. 10D

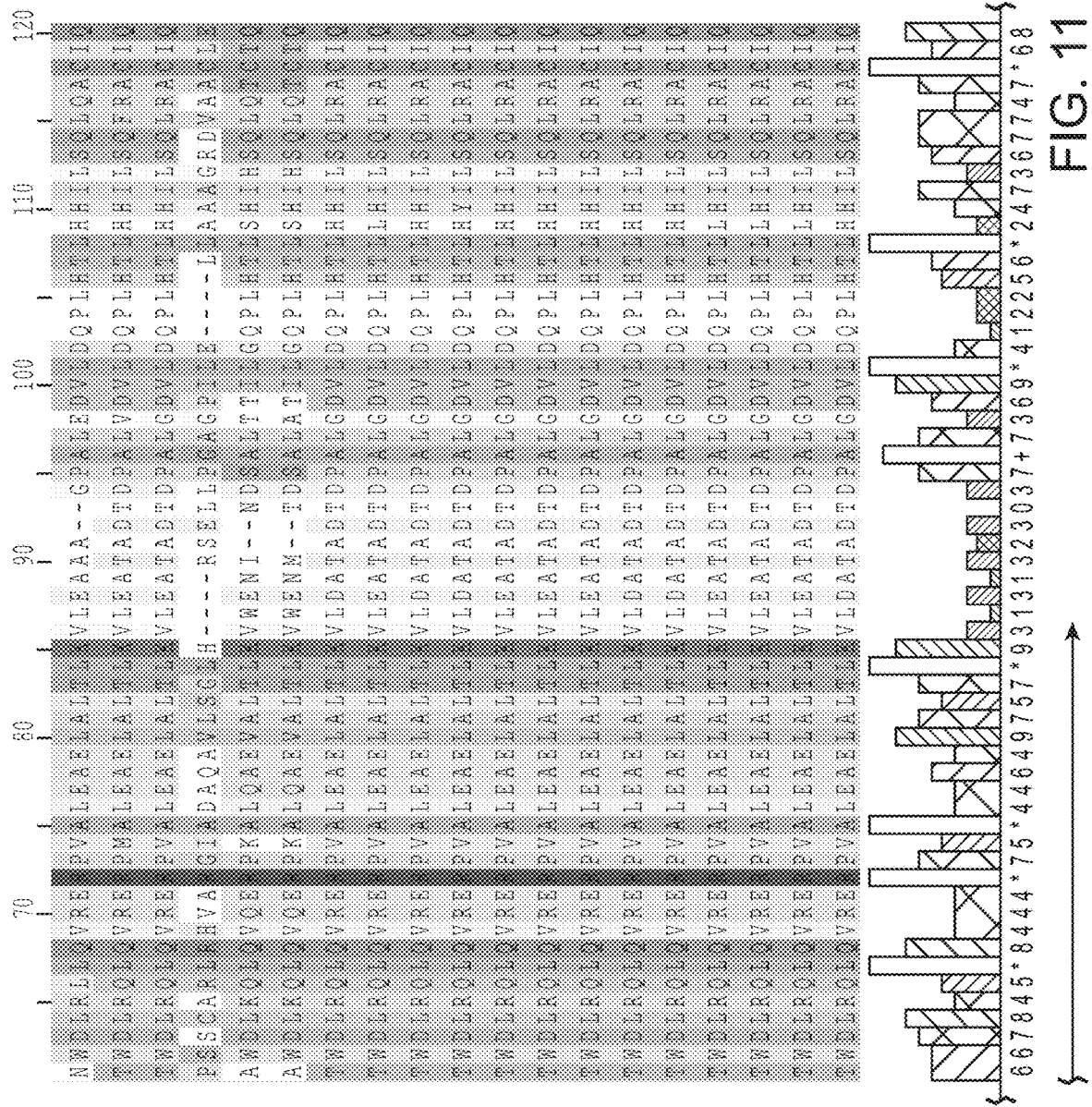
FIG. 11 (Cont. 1)

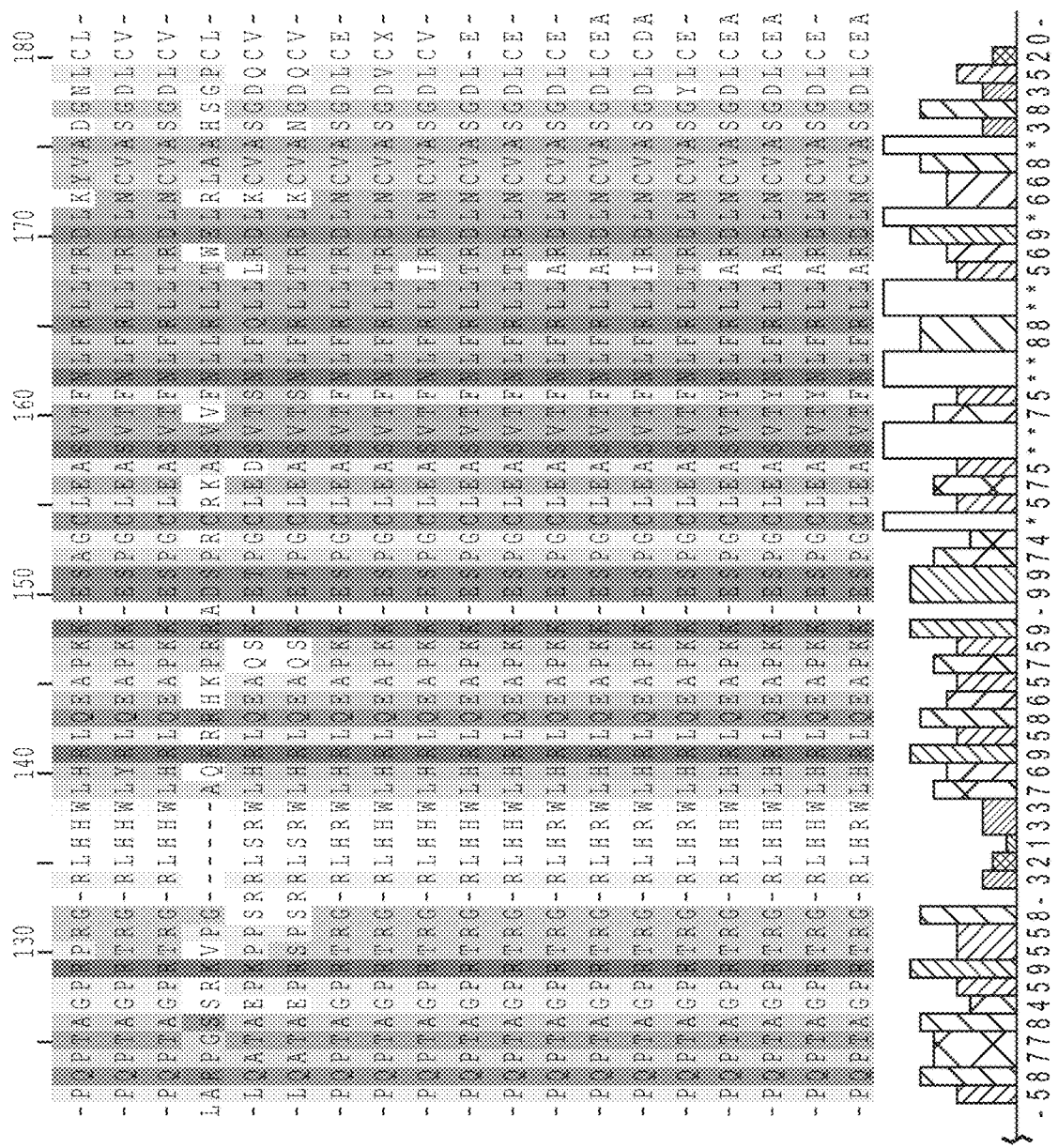
FIG. 11 (Cont. 2)

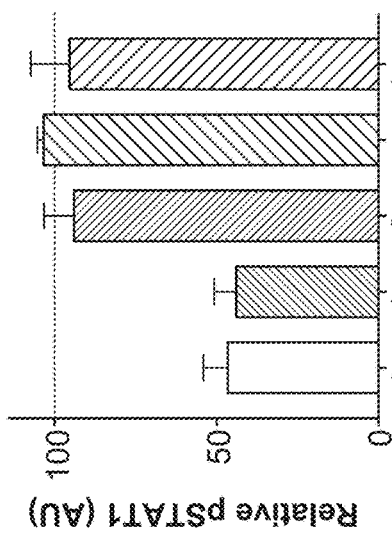
FIG. 12A
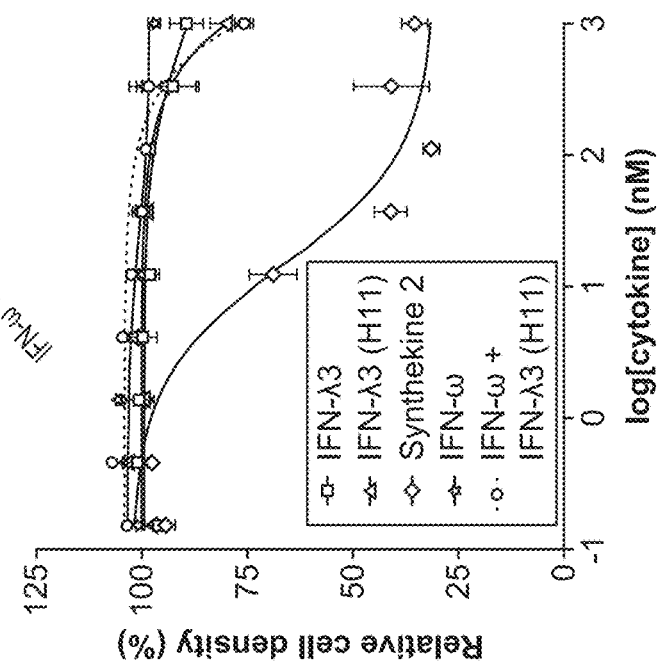
FIG. 12C
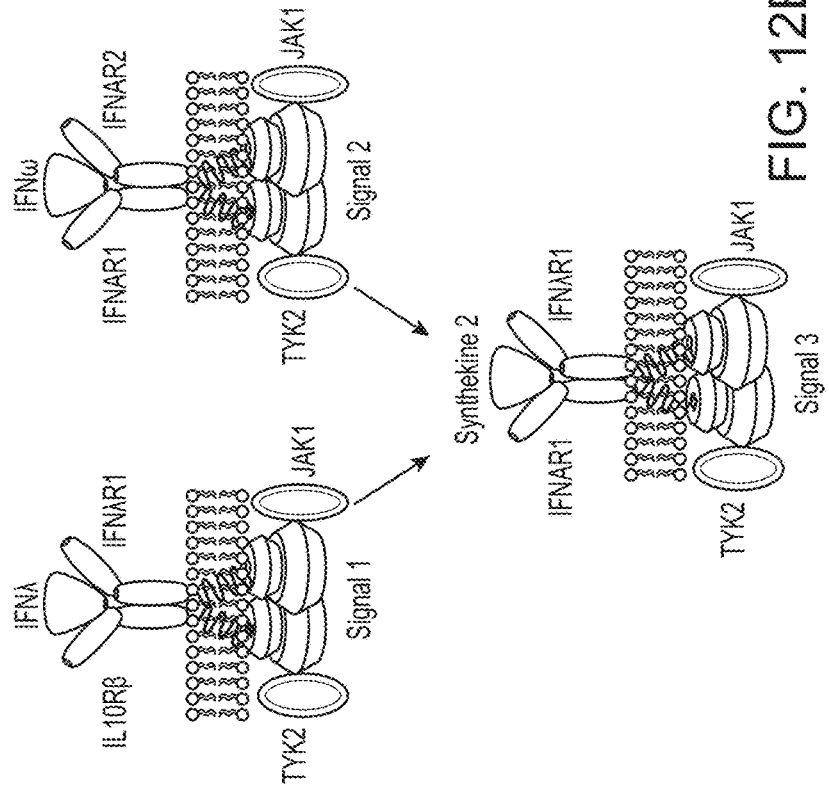
FIG. 12B
FIG. 12D

```
                              SEQUENCE LISTING

<160> NUMBER OF SEQ ID NOS: 47

<210> SEQ ID NO 1
<211> LENGTH: 169
<212> TYPE: PRT
<213> ORGANISM: Homo sapiens

<400> SEQUENCE: 1

Pro Thr Ser Lys Pro Thr Thr Gly Lys Gly Cys His Ile Gly Arg
1               5                   10                  15

Phe Lys Ser Leu Ser Pro Gln Glu Leu Ala Ser Phe Lys Lys Ala Arg
                20                  25                  30

Asp Ala Leu Glu Glu Ser Leu Lys Leu Lys Asn Trp Ser Cys Ser Ser
                35                  40                  45

Pro Val Phe Pro Gly Asn Trp Asp Leu Arg Leu Leu Gln Val Arg Glu
            50              55                  60

Arg Pro Val Ala Leu Glu Ala Glu Leu Ala Leu Thr Leu Lys Val Leu
65                  70                  75                  80

Glu Ala Ala Ala Gly Pro Ala Leu Glu Asp Val Leu Asp Gln Pro Leu
                85                  90                  95

His Thr Leu His His Ile Leu Ser Gln Leu Gln Ala Cys Ile Gln Pro
                100                 105                 110

Gln Pro Thr Ala Gly Pro Arg Pro Arg Gly Arg Leu His His Trp Leu
            115                 120                 125

His Arg Leu Gln Glu Ala Pro Lys Lys Glu Ser Ala Gly Cys Leu Glu
130                 135                 140

Ala Ser Val Thr Phe Asn Leu Phe Arg Leu Leu Thr Arg Asp Leu Lys
145                 150                 155                 160

Tyr Val Ala Asp Gly Asn Leu Cys Leu
                165

<210> SEQ ID NO 2
<211> LENGTH: 174
<212> TYPE: PRT
<213> ORGANISM: Homo sapiens

<400> SEQUENCE: 2

Pro Val Ala Arg Leu His Gly Ala Leu Pro Asp Ala Arg Gly Cys His
1               5                   10                  15

Ile Ala Gln Phe Lys Ser Leu Ser Pro Gln Glu Leu Gln Ala Phe Lys
                20                  25                  30

Arg Ala Lys Asp Ala Leu Glu Glu Ser Leu Leu Leu Lys Asp Cys Arg
            35                  40                  45

Cys His Ser Arg Leu Phe Pro Arg Thr Trp Asp Leu Arg Gln Leu Gln
            50                  55                  60

Val Arg Glu Arg Pro Met Ala Leu Glu Ala Glu Leu Ala Leu Thr Leu
65                  70                  75                  80

Lys Val Leu Glu Ala Thr Ala Asp Thr Asp Pro Ala Leu Val Asp Val
                85                  90                  95

Leu Asp Gln Pro Leu His Thr Leu His His Ile Leu Ser Gln Phe Arg
            100                 105                 110
```

```
Ala Cys Ile Gln Pro Gln Pro Thr Ala Gly Pro Arg Thr Gly Arg
            115                 120                 125

Leu His His Trp Leu Tyr Arg Leu Gln Glu Ala Pro Lys Lys Glu Ser
        130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Val
                165                 170

<210> SEQ ID NO 3
<211> LENGTH: 174
<212> TYPE: PRT
<213> ORGANISM: Homo sapiens

<400> SEQUENCE: 3

Pro Val Ala Arg Leu Arg Gly Ala Leu Pro Asp Ala Arg Gly Cys His
1               5                   10                  15

Ile Ala Gln Phe Lys Ser Leu Ser Pro Gln Glu Leu Gln Ala Phe Lys
            20                  25                  30

Arg Ala Lys Asp Ala Leu Glu Glu Ser Leu Leu Leu Lys Asp Cys Lys
        35                  40                  45

Cys Arg Ser Arg Leu Phe Pro Arg Thr Trp Asp Leu Arg Gln Leu Gln
    50                  55                  60

Val Arg Glu Arg Pro Val Ala Leu Glu Ala Glu Leu Ala Leu Thr Leu
65                  70                  75                  80

Lys Val Leu Glu Ala Thr Ala Asp Thr Asp Pro Ala Leu Gly Asp Val
                85                  90                  95

Leu Asp Gln Pro Leu His Thr Leu His His Ile Leu Ser Gln Leu Arg
            100                 105                 110

Ala Cys Ile Gln Pro Gln Pro Thr Ala Gly Pro Arg Thr Arg Gly Arg
        115                 120                 125

Leu His His Trp Leu His Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Val
                165                 170

<210> SEQ ID NO 4
<211> LENGTH: 156
<212> TYPE: PRT
<213> ORGANISM: Homo sapiens

<400> SEQUENCE: 4

Pro Arg Arg Cys Leu Leu Ser His Tyr Arg Ser Leu Glu Pro Arg Thr
1               5                   10                  15

Leu Ala Ala Ala Lys Ala Leu Arg Asp Arg Tyr Glu Glu Glu Ala Leu
            20                  25                  30

Ser Trp Gly Gln Arg Asn Cys Ser Phe Arg Pro Arg Arg Asp Pro Pro
        35                  40                  45

Arg Pro Ser Ser Cys Ala Arg Leu Arg His Val Ala Arg Gly Ile Ala
    50                  55                  60

Asp Ala Gln Ala Val Leu Ser Gly Leu His Arg Ser Glu Leu Leu Pro
65                  70                  75                  80

Gly Ala Gly Pro Ile Leu Glu Leu Leu Ala Ala Gly Arg Asp Val
                85                  90                  95
```

```
Ala Ala Cys Leu Glu Leu Ala Arg Pro Gly Ser Ser Arg Lys Val Pro
            100                 105                 110

Gly Ala Gln Lys Arg Arg His Lys Pro Arg Arg Ala Asp Ser Pro Arg
            115                 120                 125

Cys Arg Lys Ala Ser Val Val Phe Asn Leu Leu Arg Leu Leu Thr Trp
            130                 135                 140

Glu Leu Arg Leu Ala Ala His Ser Gly Pro Cys Leu
145                 150                 155
```

```
<210> SEQ ID NO 5
<211> LENGTH: 173
<212> TYPE: PRT
<213> ORGANISM: Mus musculus

<400> SEQUENCE: 5

Pro Val Pro Arg Ala Thr Arg Leu Pro Val Glu Ala Lys Asp Cys His
1               5                   10                  15

Ile Ala Gln Phe Lys Ser Leu Ser Pro Lys Glu Leu Gln Ala Phe Lys
            20                  25                  30

Lys Ala Lys Gly Ala Ile Glu Lys Arg Leu Leu Glu Lys Asp Met Arg
            35                  40                  45

Cys Ser Ser His Leu Ile Ser Arg Ala Trp Asp Leu Lys Gln Leu Gln
        50                  55                  60

Val Gln Glu Arg Pro Lys Ala Leu Gln Ala Glu Val Ala Leu Thr Leu
65                  70                  75                  80

Lys Val Trp Glu Asn Ile Asn Asp Ser Ala Leu Thr Thr Ile Leu Gly
                85                  90                  95

Gln Pro Leu His Thr Leu Ser His Ile His Ser Gln Leu Gln Thr Cys
            100                 105                 110

Thr Gln Leu Gln Ala Thr Ala Glu Pro Lys Pro Pro Ser Arg Arg Leu
            115                 120                 125

Ser Arg Trp Leu His Arg Leu Gln Glu Ala Gln Ser Lys Glu Thr Pro
        130                 135                 140

Gly Cys Leu Glu Asp Ser Val Thr Ser Asn Leu Phe Gln Leu Leu Leu
145                 150                 155                 160

Arg Asp Leu Lys Cys Val Ala Ser Gly Asp Gln Cys Val
                165                 170
```

```
<210> SEQ ID NO 6
<211> LENGTH: 173
<212> TYPE: PRT
<213> ORGANISM: Mus musculus

<400> SEQUENCE: 6

Pro Val Pro Arg Ala Thr Arg Leu Pro Val Glu Ala Lys Asp Cys His
1               5                   10                  15

Ile Ala Gln Phe Lys Ser Leu Ser Pro Lys Glu Leu Gln Ala Phe Lys
            20                  25                  30

Lys Ala Lys Asp Ala Ile Glu Lys Arg Leu Leu Glu Lys Asp Leu Arg
            35                  40                  45

Cys Ser Ser His Leu Phe Pro Arg Ala Trp Asp Leu Lys Gln Leu Gln
        50                  55                  60

Val Gln Glu Arg Pro Lys Ala Leu Gln Ala Glu Val Ala Leu Thr Leu
65                  70                  75                  80

Lys Val Trp Glu Asn Met Thr Asp Ser Ala Leu Ala Thr Ile Leu Gly
                85                  90                  95
```

```
Gln Pro Leu His Thr Leu Ser His Ile His Ser Gln Leu Gln Thr Cys
                100                 105                 110

Thr Gln Leu Gln Ala Thr Ala Glu Pro Arg Ser Pro Ser Arg Arg Leu
            115                 120                 125

Ser Arg Trp Leu His Arg Leu Gln Glu Ala Gln Ser Lys Glu Thr Pro
130                 135                 140

Gly Cys Leu Glu Ala Ser Val Thr Ser Asn Leu Phe Arg Leu Leu Thr
145                 150                 155                 160

Arg Asp Leu Lys Cys Val Ala Asn Gly Asp Gln Cys Val
                165                 170
```

<210> SEQ ID NO 7
<211> LENGTH: 174
<212> TYPE: PRT
<213> ORGANISM: Homo sapiens

<400> SEQUENCE: 7

```
Pro Val Ala Gly Leu Gly Gly Ala Leu Pro Asp Ala Arg Gly Cys His
1               5                   10                  15

Ile Ala Gln Phe Lys Ser Leu Ser Pro Gln Glu Leu Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
50                  55                  60

Val Arg Glu Arg Pro Val Ala Leu Glu Ala Glu Leu Ala Leu Thr Leu
65                  70                  75                  80

Lys Val Leu Asp Ala Thr Ala Asp Thr Asp Pro Ala Leu Gly Asp Val
                85                  90                  95

Leu Asp Gln Pro Leu His Thr Leu His His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His Arg Trp Leu His Arg Leu Gln Glu Ala Pro Lys Lys Glu Ser
130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Glu
                165                 170
```

<210> SEQ ID NO 8
<211> LENGTH: 174
<212> TYPE: PRT
<213> ORGANISM: Homo sapiens
<220> FEATURE:
<221> NAME/KEY: misc_feature
<222> LOCATION: (174)..(174)
<223> OTHER INFORMATION: Xaa can be any naturally occurring amino acid

<400> SEQUENCE: 8

```
Pro Val Ala Arg Leu Gly Gly Ala Leu Pro Asp Ala Arg Gly Cys His
1               5                   10                  15

Ile Ala Gln Phe Lys Ser Leu Tyr Pro Gln Glu Leu Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
50                  55                  60
```

```
Val Arg Glu Arg Pro Val Ala Leu Glu Ala Glu Leu Ala Leu Thr Leu
 65                  70                  75                  80

Lys Val Leu Glu Ala Thr Ala Asp Thr Asp Pro Ala Leu Gly Asp Val
                 85                  90                  95

Leu Asp Gln Pro Leu His Thr Leu Leu His Ile Leu Ser Gln Leu Arg
            100                 105                 110

Ala Cys Ile Gln Pro Gln Pro Thr Ala Gly Pro Arg Thr Arg Gly Arg
        115                 120                 125

Leu His His Trp Leu His Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Val Cys Xaa
                165                 170
```

<210> SEQ ID NO 9
<211> LENGTH: 174
<212> TYPE: PRT
<213> ORGANISM: Homo sapiens

<400> SEQUENCE: 9

```
Pro Val Ala Arg Leu Thr Gly Ala Leu Pro Val Ala Arg Gly Cys His
  1               5                  10                  15

Ile Ala Gln Phe Lys Ser Leu Ser Pro Gln Leu Gln Ala Phe Lys
                 20                  25                  30

Arg Ala Lys Asp Ala Leu Glu Glu Ser Leu Leu Leu Lys Asp Cys Lys
             35                  40                  45

Cys Arg Ser Arg Leu Phe Pro Arg Thr Trp Asp Leu Arg Gln Leu Gln
         50                  55                  60

Val Arg Glu Arg Pro Val Ala Leu Glu Ala Glu Leu Ala Leu Thr Leu
 65                  70                  75                  80

Lys Val Leu Asp Ala Thr Ala Asp Thr Asp Pro Ala Leu Gly Asp Val
                 85                  90                  95

Leu Asp Gln Pro Leu His Thr Leu His His Ile Leu Ser Gln Leu Arg
            100                 105                 110

Ala Cys Ile Gln Pro Gln Pro Thr Ala Gly Pro Arg Thr Arg Gly Arg
        115                 120                 125

Leu His His Trp Leu His Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Ile Arg Asp Leu Asn Cys Val Ala Ser Gly Asp Leu Cys Val
                165                 170
```

<210> SEQ ID NO 10
<211> LENGTH: 173
<212> TYPE: PRT
<213> ORGANISM: Homo sapiens

<400> SEQUENCE: 10

```
Pro Val Ala Gly Leu Ser Gly Ala Leu Pro Asp Ala Arg Gly Cys His
  1               5                  10                  15

Ile Ala Gln Phe Lys Ser Leu Phe Pro Gln Glu Val Gln Ala Phe Lys
                 20                  25                  30

Arg Ala Lys Asp Ala Leu Glu Glu Ser Leu Leu Leu Lys Asp Cys Lys
             35                  40                  45
```

```
Cys Arg Ser Arg Leu Phe Pro Arg Thr Trp Asp Leu Arg Gln Leu Gln
        50                  55                  60

Val Arg Glu Arg Pro Val Ala Leu Glu Ala Glu Leu Ala Leu Thr Leu
 65                  70                  75                  80

Lys Val Leu Asp Ala Thr Ala Asp Thr Asp Pro Ala Leu Gly Asp Val
                85                  90                  95

Leu Asp Gln Pro Leu His Thr Leu His Tyr Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His His Trp Leu His Arg Leu Gln Glu Ala Pro Lys Lys Glu Ser
        130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Glu
                165                 170

<210> SEQ ID NO 11
<211> LENGTH: 174
<212> TYPE: PRT
<213> ORGANISM: Homo sapiens

<400> SEQUENCE: 11

Pro Val Ala Arg Leu Ser Gly Ala Leu Pro Asp Ala Arg Gly Cys His
 1               5                  10                  15

Ile Ala Gln Phe Lys Ser Leu Phe Pro Gln Glu Val Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
        50                  55                  60

Val Arg Glu Arg Pro Val Ala Leu Glu Ala Glu Leu Ala Leu Thr Leu
 65                  70                  75                  80

Lys Val Leu Glu Ala Thr Ala Asp Thr Asp Pro Ala Leu Gly Asp Val
                85                  90                  95

Leu Asp Gln Pro Leu His Thr Leu His His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His His Trp Leu His Arg Leu Gln Glu Ala Pro Lys Lys Glu Ser
        130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Asp Leu Cys Glu
                165                 170

<210> SEQ ID NO 12
<211> LENGTH: 174
<212> TYPE: PRT
<213> ORGANISM: Homo sapiens

<400> SEQUENCE: 12

Pro Asp Ala Arg Leu Arg Gly Ala Leu Pro Asp Ala Arg Gly Cys His
 1               5                  10                  15

Ile Ala Gln Phe Lys Ser Leu Ser Pro Arg Glu Leu Gln Ala Phe Lys
                20                  25                  30
```

```
Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
 50                      55                  60

Val Arg Glu Arg Pro Val Ala Leu Glu Ala Glu Leu Ala Leu Thr Leu
 65                  70                  75                  80

Lys Val Leu Glu Ala Thr Ala Asp Thr Asp Pro Ala Leu Gly Asp Val
                 85                  90                  95

Leu Asp Gln Pro Leu His Thr Leu His His Ile Leu Ser Gln Leu Arg
            100                 105                 110

Ala Cys Ile Gln Pro Gln Pro Thr Ala Gly Pro Arg Thr Arg Gly Arg
            115                 120                 125

Leu His Arg Trp Leu His Arg Leu Gln Glu Ala Pro Lys Lys Glu Ser
130                 135                 140

Pro Gly Cys Leu Glu Ala Ser Val Thr Phe Asn Leu Phe Arg Leu Leu
145                 150                 155                 160

Ala Arg Asp Leu Asn Cys Val Ala Ser Gly Asp Leu Cys Glu
                165                 170
```

<210> SEQ ID NO 13
<211> LENGTH: 175
<212> TYPE: PRT
<213> ORGANISM: Homo sapiens

<400> SEQUENCE: 13

```
Pro Val Ala Arg Leu Ser Gly Ala Leu Pro Asp Ala Arg Gly Cys His
 1               5                  10                  15

Ile Ala Gln Phe Lys Ser Leu Ser Pro Arg Glu Leu Gln Ala Phe Lys
                20                  25                  30

Arg Ala Lys Asp Ala Leu Lys Glu Ser Leu Leu Leu Lys Asp Cys Lys
            35                  40                  45

Cys Arg Ser Arg Leu Phe Pro Arg Thr Trp Asp Leu Arg Gln Leu Gln
 50                      55                  60

Val Arg Glu Arg Pro Val Ala Leu Glu Ala Glu Leu Ala Leu Thr Leu
 65                  70                  75                  80

Lys Val Leu Glu Ala Thr Ala Asp Thr Asp Pro Ala Leu Gly Asp Val
                 85                  90                  95

Leu Asp Gln Pro Leu His Thr Leu His His Ile Leu Ser Gln Leu Arg
            100                 105                 110

Ala Cys Ile Gln Pro Gln Pro Thr Ala Gly Pro Arg Thr Arg Gly Arg
            115                 120                 125

Leu His Arg Trp Leu His Arg Leu Gln Glu Ala Pro Lys Lys Glu Ser
130                 135                 140

Pro Gly Cys Leu Glu Ala Ser Val Thr Phe Asn Leu Phe Arg Leu Leu
145                 150                 155                 160

Ala Arg Asp Leu Asn Cys Val Ala Ser Gly Asp Leu Cys Glu Ala
                165                 170                 175
```

<210> SEQ ID NO 14
<211> LENGTH: 175
<212> TYPE: PRT
<213> ORGANISM: Homo sapiens

<400> SEQUENCE: 14

```
Pro Ala Ala Arg Leu Arg Gly Ala Leu Pro Asp Ala Arg Gly Cys His
 1               5                  10                  15
```

```
Ile Ala Gln Phe Lys Ser Leu Ser Pro Arg Glu Leu Gln Ala Phe Lys
            20                  25                  30

Arg Ala Lys Asp Ala Leu Glu Glu Ser Leu Leu Leu Lys Asp Cys Lys
        35                  40                  45

Cys Arg Ser Arg Leu Phe Pro Arg Thr Trp Asp Leu Arg Gln Leu Gln
 50                  55                  60

Val Arg Glu Arg Pro Val Ala Leu Glu Ala Glu Leu Ala Leu Thr Leu
 65                  70                  75                  80

Lys Val Leu Asp Ala Thr Ala Asp Thr Asp Pro Ala Leu Gly Asp Val
                85                  90                  95

Leu Asp Gln Pro Leu His Thr Leu His His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His Arg Trp Leu His Arg Leu Gln Glu Ala Pro Lys Lys Glu Ser
        130                 135                 140

Pro Gly Cys Leu Glu Ala Ser Val Thr Phe Asn Leu Phe Arg Leu Leu
145                 150                 155                 160

Ile Arg Asp Leu Asn Cys Val Ala Ser Gly Asp Leu Cys Asp Ala
                165                 170                 175

<210> SEQ ID NO 15
<211> LENGTH: 174
<212> TYPE: PRT
<213> ORGANISM: Homo sapiens

<400> SEQUENCE: 15

Pro Ala Ala Arg Leu Arg Gly Ala Leu Pro Asp Ala Arg Gly Cys His
1               5                   10                  15

Ile Ala Gln Phe Lys Ser Leu Ser Pro Arg Glu Leu Gln Ala Phe Lys
            20                  25                  30

Arg Ala Lys Asp Ala Leu Glu Glu Ser Leu Leu Leu Lys Asp Cys Lys
        35                  40                  45

Cys Arg Ser Arg Leu Phe Pro Arg Thr Trp Asp Leu Arg Gln Leu Gln
 50                  55                  60

Val Arg Glu Arg Pro Val Ala Leu Glu Ala Glu Leu Ala Leu Thr Leu
 65                  70                  75                  80

Lys Val Leu Asp Ala Thr Ala Asp Thr Asp Pro Ala Leu Gly Asp Val
                85                  90                  95

Leu Asp Gln Pro Leu His Thr Leu His His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His Arg Trp Leu His Arg Leu Gln Glu Ala Pro Lys Lys Glu Ser
        130                 135                 140

Pro Gly Cys Leu Glu Ala Ser Val Thr Phe Asn Leu Phe Arg Leu Leu
145                 150                 155                 160

Thr Arg Asp Leu Asn Cys Val Ala Ser Gly Tyr Leu Cys Glu
                165                 170

<210> SEQ ID NO 16
<211> LENGTH: 175
<212> TYPE: PRT
<213> ORGANISM: Homo sapiens

<400> SEQUENCE: 16
```

```
Pro Ala Arg Leu Arg Gly Ala Leu Pro Asp Ala Arg Gly Cys His
1               5                   10                  15

Ile Ala Gln Phe Lys Ser Leu Ser Pro Arg Glu Leu Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
50                      55                  60

Val Arg Glu Arg Pro Val Ala Leu Glu Ala Glu Leu Ala Leu Thr Leu
65                  70                  75                  80

Lys Val Leu Glu Ala Thr Ala Asp Thr Asp Pro Ala Leu Gly Asp Val
                85                  90                  95

Leu Asp Gln Pro Leu His Thr Leu Leu His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His His Trp Leu His Arg Leu Gln Glu Ala Pro Lys Lys Glu Ser
130                 135                 140

Pro Gly Cys Leu Glu Ala Ser Val Thr Tyr Asn Leu Phe Arg Leu Leu
145                 150                 155                 160

Ala Arg Asp Leu Asn Cys Val Ala Ser Gly Asp Leu Cys Glu Ala
                165                 170                 175

<210> SEQ ID NO 17
<211> LENGTH: 175
<212> TYPE: PRT
<213> ORGANISM: Homo sapiens

<400> SEQUENCE: 17

Pro Val Ala Arg Leu Ser Gly Ala Leu Pro Asp Ala Arg Gly Cys His
1               5                   10                  15

Ile Ala Gln Phe Lys Ser Leu Ser Pro Arg Glu Leu Gln Ala Phe Lys
                20                  25                  30

Arg Ala Lys Asp Ala Leu Glu Glu Ser Leu Leu Leu Lys Asp Cys Lys
            35                  40                  45

Cys Arg Ser Arg Leu Phe Pro Arg Thr Trp Asp Leu Arg Gln Leu Gln
50                      55                  60

Val Arg Glu Arg Pro Val Ala Leu Glu Ala Glu Leu Ala Leu Thr Leu
65                  70                  75                  80

Lys Val Leu Glu Ala Thr Ala Asp Thr Asp Pro Ala Leu Gly Asp Val
                85                  90                  95

Leu Asp Gln Pro Leu His Thr Leu Leu His Ile Leu Ser Gln Leu Arg
                100                 105                 110

Ala Cys Ile Gln Pro Gln Pro Thr Ala Gly Pro Arg Thr Arg Gly Arg
            115                 120                 125

Leu His His Trp Leu His Arg Leu Gln Glu Ala Pro Lys Lys Glu Ser
130                 135                 140

Pro Gly Cys Leu Glu Ala Ser Val Thr Tyr Asn Leu Phe Arg Leu Leu
145                 150                 155                 160

Ala Arg Asp Leu Asn Cys Val Ala Ser Gly Asp Leu Cys Glu Ala
                165                 170                 175

<210> SEQ ID NO 18
<211> LENGTH: 174
<212> TYPE: PRT
```

<213> ORGANISM: Homo sapiens

<400> SEQUENCE: 18

```
Pro Val Ala Arg Leu Ser Gly Ala Leu Pro Asp Ala Arg Gly Cys His
1               5                   10                  15

Ile Ala Gln Phe Lys Ser Leu Ser Pro Gln Glu Leu Gln Ala Phe Lys
            20                  25                  30

Arg Ala Lys Asp Ala Leu Glu Glu Ser Leu Leu Leu Lys Asp Cys Lys
        35                  40                  45

Cys Arg Ser Arg Leu Phe Pro Arg Thr Trp Asp Leu Arg Gln Leu Gln
    50                  55                  60

Val Arg Glu Arg Pro Val Ala Leu Glu Ala Leu Ala Leu Thr Leu
65                  70                  75                  80

Lys Val Leu Glu Ala Thr Ala Asp Thr Asp Pro Ala Leu Gly Asp Val
                85                  90                  95

Leu Asp Gln Pro Leu His Thr Leu Leu His Ile Leu Ser Gln Leu Arg
            100                 105                 110

Ala Cys Ile Gln Pro Gln Pro Thr Ala Gly Pro Arg Thr Arg Gly Arg
        115                 120                 125

Leu His His Trp Leu His Arg Leu Gln Glu Ala Pro Lys Lys Glu Ser
    130                 135                 140

Pro Gly Cys Leu Glu Ala Ser Val Thr Tyr Asn Leu Phe Arg Leu Leu
145                 150                 155                 160

Ala Arg Asp Leu Asn Cys Val Ala Ser Gly Asp Leu Cys Glu
                165                 170
```

<210> SEQ ID NO 19
<211> LENGTH: 175
<212> TYPE: PRT
<213> ORGANISM: Homo sapiens

<400> SEQUENCE: 19

```
Pro Val Ala Gly Leu Arg Gly Ala Leu Pro Asp Ala Arg Gly Cys His
1               5                   10                  15

Ile Ala Gln Phe Lys Ser Leu Ser Pro Arg Glu Leu Gln Ala Phe Lys
            20                  25                  30

Arg Ala Lys Asp Ala Leu Glu Glu Ser Leu Leu Leu Lys Asp Cys Lys
        35                  40                  45

Cys Arg Ser Arg Leu Phe Pro Arg Thr Trp Asp Leu Arg Gln Leu Gln
    50                  55                  60

Val Arg Glu Arg Pro Val Ala Leu Glu Ala Leu Ala Leu Thr Leu
65                  70                  75                  80

Lys Val Leu Asp Ala Thr Ala Asp Thr Asp Pro Ala Leu Gly Asp Val
                85                  90                  95

Leu Asp Gln Pro Leu His Thr Leu His His Ile Leu Ser Gln Leu Arg
            100                 105                 110

Ala Cys Ile Gln Pro Gln Pro Thr Ala Gly Pro Arg Thr Arg Gly Arg
        115                 120                 125

Leu His Arg Trp Leu His Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Ala Arg Asp Leu Asn Cys Val Ala Ser Gly Asp Leu Cys Glu Ala
                165                 170                 175
```

<210> SEQ ID NO 20
<211> LENGTH: 163
<212> TYPE: PRT
<213> ORGANISM: Homo sapiens

<400> SEQUENCE: 20

Ala Arg Gly Cys His Ile Ala Gln Phe Lys Ser Leu Ser Pro Ala Glu
1               5                   10                  15

Leu Gln Ala Phe Lys Arg Ala Lys Asp Ala Leu Glu Glu Ser Leu Leu
            20                  25                  30

Leu Lys Asp Cys Lys Cys Arg Ser Arg Leu Phe Pro Arg Thr Trp Asp
        35                  40                  45

Leu Arg Gln Leu Gln Val Arg Glu Arg Pro Val Ala Leu Glu Ala Glu
    50                  55                  60

Leu Ala Leu Thr Leu Lys Val Leu Glu Ala Thr Ala Asp Thr Asp Pro
65                  70                  75                  80

Ala Leu Gly Asp Val Leu Asp Ala Pro Leu Ala Thr Leu His His Ile
                85                  90                  95

Leu Ser Gln Leu Arg Ala Cys Ile Gln Pro Gln Pro Thr Ala Gly Pro
            100                 105                 110

Arg Thr Arg Gly Arg Leu His Arg Trp Leu His Arg Leu Gln Glu Ala
        115                 120                 125

Pro Lys Lys Glu Ser Pro Gly Cys Leu Glu Ala Ser Val Thr Phe Asn
    130                 135                 140

Leu Phe Arg Leu Leu Ala Arg Asp Leu Asn Cys Val Ala Ser Gly Asp
145                 150                 155                 160

Leu Cys Glu

<210> SEQ ID NO 21
<211> LENGTH: 174
<212> TYPE: PRT
<213> ORGANISM: Homo sapiens

<400> SEQUENCE: 21

Leu Gly Cys Asp Leu Pro Gln Asn His Gly Leu Leu Ser Arg Asn Thr
1               5                   10                  15

Leu Val Leu Leu His Gln Met Arg Arg Ile Ser Pro Phe Leu Cys Leu
            20                  25                  30

Lys Asp Arg Arg Asp Phe Arg Phe Pro Gln Glu Met Val Lys Gly Ser
        35                  40                  45

Gln Leu Gln Lys Ala His Val Met Ser Val Leu His Glu Met Leu Gln
    50                  55                  60

Gln Ile Phe Ser Leu Phe His Thr Glu Arg Ser Ser Ala Ala Trp Asn
65                  70                  75                  80

Met Thr Leu Leu Asp Gln Leu His Thr Gly Leu His Gln Gln Leu Gln
                85                  90                  95

His Leu Glu Thr Cys Leu Leu Gln Val Val Gly Glu Gly Glu Ser Ala
            100                 105                 110

Gly Ala Ile Ser Ser Pro Ala Leu Thr Leu Arg Arg Tyr Phe Gln Gly
        115                 120                 125

Ile Arg Val Tyr Leu Lys Glu Lys Lys Tyr Ser Asp Cys Ala Trp Glu
    130                 135                 140

Val Val Arg Met Glu Ile Met Lys Ser Leu Phe Leu Ser Thr Asn Met
145                 150                 155                 160

Gln Glu Arg Leu Arg Ser Lys Asp Arg Asp Leu Gly Ser Ser
                165                 170

```
<210> SEQ ID NO 22
<211> LENGTH: 174
<212> TYPE: PRT
<213> ORGANISM: Homo sapiens

<400> SEQUENCE: 22

Leu Gly Cys Asp Leu Pro Gln Asn His Gly Leu Leu Ser Ala Asn Thr
1               5                   10                  15

Leu Val Leu Leu His Gln Met Arg Arg Ile Ser Pro Phe Leu Cys Ala
                20                  25                  30

Lys Asp Ala Arg Asp Phe Arg Phe Pro Gln Glu Met Val Lys Gly Ser
            35                  40                  45

Gln Leu Gln Lys Ala His Val Met Ser Val Leu His Glu Met Leu Gln
        50                  55                  60

Gln Ile Phe Ser Leu Phe His Thr Glu Arg Ser Ser Ala Ala Trp Asn
65                  70                  75                  80

Met Thr Leu Leu Asp Gln Leu His Thr Gly Leu His Gln Gln Leu Gln
                85                  90                  95

His Leu Glu Thr Cys Leu Leu Gln Val Val Gly Glu Gly Glu Ser Ala
            100                 105                 110

Gly Ala Ile Ser Ser Pro Ala Leu Thr Leu Arg Arg Tyr Phe Gln Gly
        115                 120                 125

Ile Arg Val Tyr Leu Lys Glu Lys Lys Tyr Ser Asp Cys Ala Trp Glu
130                 135                 140

Val Val Arg Met Glu Ile Met Ala Ser Leu Phe Leu Ser Thr Asn Met
145                 150                 155                 160

Gln Glu Arg Leu Arg Ser Lys Asp Arg Asp Leu Gly Ser Ser
                165                 170

<210> SEQ ID NO 23
<211> LENGTH: 351
<212> TYPE: PRT
<213> ORGANISM: Homo sapiens

<400> SEQUENCE: 23

Ala Arg Gly Cys His Ile Ala Gln Phe Lys Ser Leu Ser Pro Ala Glu
1               5                   10                  15

Leu Gln Ala Phe Lys Arg Ala Lys Asp Ala Leu Glu Glu Ser Leu Leu
                20                  25                  30

Leu Lys Asp Cys Lys Cys Arg Ser Arg Leu Phe Pro Arg Thr Trp Asp
            35                  40                  45

Leu Arg Gln Leu Gln Val Arg Glu Arg Pro Val Ala Leu Glu Ala Glu
        50                  55                  60

Leu Ala Leu Thr Leu Lys Val Leu Glu Ala Thr Ala Asp Thr Asp Pro
65                  70                  75                  80

Ala Leu Gly Asp Val Leu Asp Ala Pro Leu Ala Thr Leu His His Ile
                85                  90                  95

Leu Ser Gln Leu Arg Ala Cys Ile Gln Pro Gln Pro Thr Ala Gly Pro
            100                 105                 110

Arg Thr Arg Gly Arg Leu His Trp Leu His Arg Leu Gln Glu Ala
        115                 120                 125

Pro Lys Lys Glu Ser Pro Gly Cys Leu Glu Ala Ser Val Thr Phe Asn
130                 135                 140

Leu Phe Arg Leu Leu Ala Arg Asp Leu Asn Cys Val Ala Ser Gly Asp
145                 150                 155                 160
```

Leu Cys Glu Gly Ser Gly Ser Gly Leu Gly Cys Asp Leu Pro Gln Asn
            165                 170                 175

His Gly Leu Leu Ser Ala Asn Thr Leu Val Leu Leu His Gln Met Arg
        180                 185                 190

Arg Ile Ser Pro Phe Leu Cys Ala Lys Asp Ala Arg Asp Phe Arg Phe
    195                 200                 205

Pro Gln Glu Met Val Lys Gly Ser Gln Leu Gln Lys Ala His Val Met
210                 215                 220

Ser Val Leu His Glu Met Leu Gln Gln Ile Phe Ser Leu Phe His Thr
225                 230                 235                 240

Glu Arg Ser Ser Ala Ala Trp Asn Met Thr Leu Leu Asp Gln Leu His
            245                 250                 255

Thr Gly Leu His Gln Gln Leu His Leu Glu Thr Cys Leu Leu Gln
        260                 265                 270

Val Val Gly Glu Gly Glu Ser Ala Gly Ala Ile Ser Ser Pro Ala Leu
    275                 280                 285

Thr Leu Arg Arg Tyr Phe Gln Gly Ile Arg Val Tyr Leu Lys Glu Lys
    290                 295                 300

Lys Tyr Ser Asp Cys Ala Trp Glu Val Val Arg Met Glu Ile Met Ala
305                 310                 315                 320

Ser Leu Phe Leu Ser Thr Asn Met Gln Glu Arg Leu Arg Ser Lys Asp
            325                 330                 335

Arg Asp Leu Gly Ser Ser Ala Ala Ala His His His His His His
            340                 345                 350

<210> SEQ ID NO 24
<211> LENGTH: 9
<212> TYPE: PRT
<213> ORGANISM: Artificial sequence
<220> FEATURE:
<223> OTHER INFORMATION: synthetic sequence

<400> SEQUENCE: 24

His Phe Pro Gly Asn Leu Pro Asn Met
1               5

<210> SEQ ID NO 25
<211> LENGTH: 8
<212> TYPE: PRT
<213> ORGANISM: Artificial sequence
<220> FEATURE:
<223> OTHER INFORMATION: synthetic sequence

<400> SEQUENCE: 25

Leu Asp Lys Ser Asn Phe Gln Gln
1               5

<210> SEQ ID NO 26
<211> LENGTH: 8
<212> TYPE: PRT
<213> ORGANISM: Artificial sequence
<220> FEATURE:
<223> OTHER INFORMATION: synthetic sequence

<400> SEQUENCE: 26

Ile Ala Gln Phe Lys Ser Leu Ser
1               5

<210> SEQ ID NO 27
<211> LENGTH: 9

```
<212> TYPE: PRT
<213> ORGANISM: Artificial sequence
<220> FEATURE:
<223> OTHER INFORMATION: synthetic sequence

<400> SEQUENCE: 27

Arg Asp Leu Arg Asp Ala Phe Ser Arg
1               5

<210> SEQ ID NO 28
<211> LENGTH: 9
<212> TYPE: PRT
<213> ORGANISM: Artificial sequence
<220> FEATURE:
<223> OTHER INFORMATION: synthetic sequence

<400> SEQUENCE: 28

Pro Tyr Ile Thr Asn Arg Thr Phe Met
1               5

<210> SEQ ID NO 29
<211> LENGTH: 9
<212> TYPE: PRT
<213> ORGANISM: Artificial sequence
<220> FEATURE:
<223> OTHER INFORMATION: synthetic sequence

<400> SEQUENCE: 29

Pro Gln Glu Leu Gln Ala Phe Lys Arg
1               5

<210> SEQ ID NO 30
<211> LENGTH: 11
<212> TYPE: PRT
<213> ORGANISM: Artificial sequence
<220> FEATURE:
<223> OTHER INFORMATION: synthetic sequence

<400> SEQUENCE: 30

Phe Tyr Leu Glu Glu Val Met Pro Gln Ala Glu
1               5                   10

<210> SEQ ID NO 31
<211> LENGTH: 11
<212> TYPE: PRT
<213> ORGANISM: Artificial sequence
<220> FEATURE:
<223> OTHER INFORMATION: synthetic sequence

<400> SEQUENCE: 31

Phe Thr Leu Glu Glu Val Leu Phe Pro Gln Ser
1               5                   10

<210> SEQ ID NO 32
<211> LENGTH: 10
<212> TYPE: PRT
<213> ORGANISM: Artificial sequence
<220> FEATURE:
<223> OTHER INFORMATION: synthetic sequence

<400> SEQUENCE: 32

Leu Thr Leu Lys Val Leu Glu Ala Thr Ala
1               5                   10

<210> SEQ ID NO 33
<211> LENGTH: 17
<212> TYPE: PRT
```

<213> ORGANISM: Artificial sequence
<220> FEATURE:
<223> OTHER INFORMATION: synthetic sequence

<400> SEQUENCE: 33

Ile Lys Ala His Val Asn Ser Leu Gly Glu Asn Leu Lys Thr Leu Arg
1               5                   10                  15
Leu

<210> SEQ ID NO 34
<211> LENGTH: 17
<212> TYPE: PRT
<213> ORGANISM: Artificial sequence
<220> FEATURE:
<223> OTHER INFORMATION: synthetic sequence

<400> SEQUENCE: 34

Phe Gln Pro Tyr Met Gln Glu Val Val Pro Phe Leu Ala Arg Leu Ser
1               5                   10                  15
Asn

<210> SEQ ID NO 35
<211> LENGTH: 17
<212> TYPE: PRT
<213> ORGANISM: Artificial sequence
<220> FEATURE:
<223> OTHER INFORMATION: synthetic sequence

<400> SEQUENCE: 35

Leu Gly Asp Val Leu Asp Gln Pro Leu His Thr Leu His His Ile Leu
1               5                   10                  15
Ser

<210> SEQ ID NO 36
<211> LENGTH: 5
<212> TYPE: PRT
<213> ORGANISM: Artificial sequence
<220> FEATURE:
<223> OTHER INFORMATION: synthetic sequence

<400> SEQUENCE: 36

Gly Gly Gly Gly Ser
1               5

<210> SEQ ID NO 37
<211> LENGTH: 9
<212> TYPE: PRT
<213> ORGANISM: Artificial sequence
<220> FEATURE:
<223> OTHER INFORMATION: synthetic sequence

<400> SEQUENCE: 37

Gly Gly Gly Gly Gly Gly Gly Gly Gly
1               5

<210> SEQ ID NO 38
<211> LENGTH: 9
<212> TYPE: PRT
<213> ORGANISM: Artificial sequence
<220> FEATURE:
<223> OTHER INFORMATION: synthetic sequence

<400> SEQUENCE: 38

Glu Glu Glu Glu Glu Glu Glu Glu Glu
1               5

```
<210> SEQ ID NO 39
<211> LENGTH: 9
<212> TYPE: PRT
<213> ORGANISM: Artificial sequence
<220> FEATURE:
<223> OTHER INFORMATION: synthetic sequence

<400> SEQUENCE: 39

Ser Ser Ser Ser Ser Ser Ser Ser Ser
1               5

<210> SEQ ID NO 40
<211> LENGTH: 9
<212> TYPE: PRT
<213> ORGANISM: Artificial sequence
<220> FEATURE:
<223> OTHER INFORMATION: synthetic sequence

<400> SEQUENCE: 40

Gly Gly Gly Gly Gly Cys Pro Pro Cys
1               5

<210> SEQ ID NO 41
<211> LENGTH: 15
<212> TYPE: PRT
<213> ORGANISM: Artificial sequence
<220> FEATURE:
<223> OTHER INFORMATION: synthetic sequence

<400> SEQUENCE: 41

Gly Gly Gly Gly Ser Gly Gly Gly Gly Ser Gly Gly Gly Gly Ser
1               5                   10                  15

<210> SEQ ID NO 42
<211> LENGTH: 13
<212> TYPE: PRT
<213> ORGANISM: Artificial sequence
<220> FEATURE:
<223> OTHER INFORMATION: synthetic sequence

<400> SEQUENCE: 42

Ser Cys Val Pro Leu Met Arg Cys Gly Gly Cys Cys Asn
1               5                   10

<210> SEQ ID NO 43
<211> LENGTH: 14
<212> TYPE: PRT
<213> ORGANISM: Artificial sequence
<220> FEATURE:
<223> OTHER INFORMATION: synthetic sequence

<400> SEQUENCE: 43

Pro Ser Cys Val Pro Leu Met Arg Cys Gly Gly Cys Cys Asn
1               5                   10

<210> SEQ ID NO 44
<211> LENGTH: 9
<212> TYPE: PRT
<213> ORGANISM: Artificial sequence
<220> FEATURE:
<223> OTHER INFORMATION: synthetic sequence

<400> SEQUENCE: 44

Gly Asp Leu Ile Tyr Arg Asn Gln Lys
1               5
```

```
<210> SEQ ID NO 45
<211> LENGTH: 23
<212> TYPE: PRT
<213> ORGANISM: Artificial sequence
<220> FEATURE:
<223> OTHER INFORMATION: synthetic sequence

<400> SEQUENCE: 45

Gly Gly Gly Gly Gly Gly Gly Gly Pro Ser Cys Val Pro Leu Met
1               5                   10                  15

Arg Cys Gly Gly Cys Cys Asn
            20

<210> SEQ ID NO 46
<211> LENGTH: 14
<212> TYPE: PRT
<213> ORGANISM: Artificial sequence
<220> FEATURE:
<223> OTHER INFORMATION: synthetic sequence

<400> SEQUENCE: 46

Gly Ser Thr Ser Gly Ser Gly Lys Ser Ser Glu Gly Lys Gly
1               5                   10

<210> SEQ ID NO 47
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(5)
<223> OTHER INFORMATION: The residues may be repeated n times.

<400> SEQUENCE: 47

Gly Gly Gly Gly Ser
1               5
```

VARIANT TYPE III INTERFERONS AND SYNTHEKINES

CROSS REFERENCE

This application claims benefit and is a 371 application and claims the benefit of PCT Application No. PCT/US2017/054498, filed Sep. 29, 2017, which claims benefit of U.S. Provisional Patent Application No. 62/402,204, filed Sep. 30, 2016, which applications are incorporated herein by reference in their entirety.

FEDERALLY SPONSORED RESEARCH AND DEVELOPMENT

This invention was made with Government support under contracts AI109662 and CA175127 awarded by the National Institutes of Health. The Government has certain rights in the invention.

BACKGROUND

Interferons (IFN) induce an innate response to anti-viral infections and cancer. Nearly all cells in humans are responsive to Type I IFNs, however in the clinic these cytokines have been associated with severe side-effects, in part due to the systemic cellular response. Type III Interferons are a family of cytokines that provide targeted anti-viral (AV) and anti-proliferative (AP) activities to epithelial tissue such as the lung and liver. This targeted activity may impart a lower toxicity profile compared to the Type I IFNs. In vitro, Type III IFNs have a 100-fold larger EC50 than the more potent Type I IFNs. This means the type III IFNs require 100 times the amount of protein as type I IFNs to achieve the same activity (EC50). Consistent with the lower in vitro efficacy, clinical trials of type III IFNs reveal limited efficacy relative to Type I IFNs.

Type III IFNs bind and signal through a pair of receptors that are distinct from those used by Type I IFNs. The receptors for Type III IFN are IL-10 Receptor Beta (IL-10Rβ) and IFNλ Receptor 1 (IFNλR1). Affinity of the cytokine for IFNλR1 receptor has been measured to be approximately, 850 nM. The affinity for the low affinity IL-10Rβ receptor alone is estimated to be >100 NM. The limited expression of the IFNλR1 to epithelial cells, such as the lung and liver provide natural targeting for the Type III IFNs. Viruses like HCV, Norovirus, Influenza, HBV, and HBV/HDV co-infections that primarily infect epithelial tissue and cancers restricted to such tissues are candidates for treatment by Type III IFNs.

Protein engineering to improve the efficacy of Type III interferons, and improved treatment of viral infections such as HCV are of great interest. The present invention addresses this issue.

SUMMARY

Compositions and methods are provided relating to Type III IFNs, also referred to as IFNλs, where variant human IFNλ proteins are provided, which proteins comprise one or more amino acid mutations that alter the binding affinity of the variant IFNλ for one or both of its receptors. Relative to the wild-type protein, the variant IFNλs activate Jak/STAT signaling in cells with an improvement in the EC50 level, higher levels of gene induction, and improved anti-viral and anti-proliferative activities. In some embodiments the affinity matured IFNλ has an altered affinity for both IFNλR1 and IL-10Rβ relative to the wild-type protein.

Compositions and methods are also provided relating to engineered synthetic signaling molecules, herein termed "synthekines" comprising an IFNλ polypeptide. Synthekines are genetically engineered, bi-specific ligands of cell surface receptors, where the synthekine specifically binds at high affinity to the extracellular domain(s) of at least one and frequently two different cell surface receptor polypeptides. An IFNλ synthekine comprises a high affinity binding domain that binds to an IFNλ receptor, i.e. IFNλR1 or IL-10Rβ; and a Type I IFN receptor, i.e. IFNAR1 or IFNAR2.

In some embodiments an IFNλ synthekine provides for an engineered receptor binding pair disclosed herein, where the synthekine is comprised of binding domains such as Type I and Type III interferons, de novo designed binding proteins, antibody derived binding proteins, e.g. scFv, Fab, etc. and other portions of antibodies that specifically bind to one or more receptor ECD sequences; nanobody derived binding domains; knottin-based engineered scaffolds; norrin and engineered binding fragments derived therefrom, naturally occurring binding domains, and the like, where the receptor binding domains may be selected from any domain that binds the desired receptor extracellular domain at high affinity, e.g. a Kd of not more than about $1 \times 10^{-7}$ M, not more than about $1 \times 10^{-8}$ M, not more than about $1 \times 10^{-9}$ M, or not more than about $1 \times 10^{-10}$ M.

A polypeptide IFNλ synthekine may be a single chain, dimer, or higher order multimer. The binding domain/element for each receptor, e.g. IL-10IRβ, IFNλR1, IFNAR1, IFNAR2, etc. may be directly joined, or may be separated by a linker, e.g. a polypeptide linker, or a non-peptidic linker, etc. In some embodiments the synthekine does not activate a native receptor configuration, as described above. Such binding domains include, without limitation, dominant negative mutants of IFNλ and a Type I IFN. A binding domain may be affinity selected to enhance binding to a desired receptor; and/or mutagenized to prevent binding to an undesired receptor.

In some embodiments an IFNλ synthekine is a hybrid protein comprising wild type or variant IFNλ polypeptide, e.g. IFNL1, IFNL2, IFNL3, IFNL4 and a wild type or variant Type I IFN polypeptide, e.g. IFNA1, IFNA2, IFNA4, IFNA5, IFNA6, IFNA7, IFNA8, IFNA10, IFNA13, IFNA14, IFNA16, IFNA17, IFNA21, IFNβ, IFNε, IFNκ, IFNω. Such synthekines compel formation of a non-natural receptor dimer, for example a dimer composed of IFNλR1 and IFNAR1. The IFNλ synthekine may comprise a IFNλ variant polypeptide having altered binding affinity for one or both of its receptors. The synthekine may comprise a Type I IFN variant polypeptide having altered affinity for one or both of its receptors.

In certain embodiments an IFNλ synthekine is a fusion protein comprising an IFNλ variant polypeptide that binds to IFNλR1 but not IL-10Rβ and an IFNω variant polypeptide that binds to IFNAR1 but not IFNAR2. These polypeptides may be joined through a linker. The hybrid synthekine thus created then compels formation of an IFNλR1/IFNAR1 dimer. This dimer recapitulates the JAK1/TYK2 pairing used by the natural IFNλR1 dimer, except it replaces the Tyk2 of IL-10Rβ with that of IFNAR1. Ablation of binding to the binding of IL-10Rβ to IFNλ, and IFNAR2 to IFω may be accomplished by introducing mutations into the respective receptor binding sites. A striking result of an IFNλ synthekine is maintenance of IFNω STAT1 activation levels; and potent anti-proliferative activity against IFNλR1 expressing cells, e.g. virus-infected cells and epithelial tissue, e.g. lung tissue, liver tissue, etc. Epithelial cancer cells are of particular interest for inhibition of proliferation by contacting with a synthekine as described herein.

In other embodiments an IFNλ synthekine is engineered from an IFNλ polypeptide that binds to IL-10Rβ but not IFNλR1; and a Type I interferon that binds to only one of IFNAR1 or IFNAR2, which synthekine also results in a novel Tyk2/Jak1 pairing.

A synthekine polypeptide can be fused, linked, or alternatively co-administered with an agent to enhance receptor activation. A synthekine can be fused, linked or alternatively co-administered with a cytokine, chemokine, or growth factor of interest.

The synthekine binding domains may be contiguous within one globular domain, or separated by a linker, e.g. a polypeptide linker, or a non-peptidic linker, etc. The length of the linker, and therefore the spacing between the binding domains can be used to modulate the signal strength, and can be selected depending on the desired use of the synthekine. A synthekine can be multimerized, e.g. through an Fc domain, by concatenation, coiled coils, polypeptide zippers, biotin/avidin or streptavidin multimerization, and the like. The synthekine can also be joined to a moiety such as PEG, MSA, Fc, etc. as known in the art to enhance stability in vivo.

Other embodiments of the invention include isolated affinity matured IFNλ variant polypeptides and derivatives and fragments thereof, including IFNλ synthekines, pharmaceutical formulations comprising one or more of the IFNλ variant polypeptides or synthekines; and cell lines that produce these IFNλ variant polypeptides or synthekines. Also provided are amino acid sequences that confer the binding specificity of these IFNλ variant polypeptides or synthekines.

The invention further provides: isolated nucleic acid encoding the IFNλ variant polypeptides or synthekines; a vector comprising that nucleic acid, optionally operably linked to control sequences recognized by a host cell transformed with the vector; a host cell comprising that vector; a process for producing the interferons comprising culturing the host cell so that the nucleic acid is expressed and, optionally, recovering the interferon from the host cell culture (e.g. from the host cell culture medium). The invention also provides a composition comprising one or more of the IFNλ variant polypeptides or synthekines and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

In some embodiments, methods are provided for treatment of an infection, including without limitation chronic infections, the methods comprising administering an effective dose of IFNλ variant polypeptides or synthekines to a patient in need thereof. In particular embodiments the methods are used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, etc.; and intracellular protozoan pathogens, e.g. *Plasmodium* sp, *Trypanosoma* sp., *Giardia* sp., *Toxoplasma* sp., *Leishmania* sp., etc. Treatment of infection with hepatitis viruses, e.g. HBV, HCV, HDV and related liver disease, including cancer, is of interest. Inhibition of human immunodeficiency virus type 1 (HIV-1) infection of blood monocyte-derived macrophages; and herpes simplex virus type 1 (HSV1) infection of human astrocytes and neurons is also of interest.

In some embodiments, methods are provided for treatment of a cancer responsive to Type III interferon, the methods comprising administering an effective dose of IFNλ variant polypeptides or synthekines to a patient in need thereof. In some embodiments, treatment is combined with a second agent, e.g. a Type I IFN, a checkpoint inhibitor, chemotherapy, radiation, etc. Cancers response to Type III interferon generally express a receptor for Type III interferon, e.g. IFNλR1, which cells may include without limitation epithelial cells, colorectal adenocarcinoma, glioblastoma, melanoma, basal cell carcinoma, hepatocarcinoma, etc.

Other aspects and features will be readily apparent to the ordinarily skilled artisan upon reading the present disclosure.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) Wild-type IFN-λ3[22] was displayed on-yeast and stained with 1 μM monomer or 400 nM streptavidin tetramers of IL-10Rβ[21] (x-axis, FL4) in the presence or absence of 50 nM streptavidin tetramers of IFN-λR1[13] (y-axis, FL2). (FIG. 1B) Density plot of fluorescence (FL4) for the naïve and evolved first generation (error-prone) and second generation (shuffled) IFN-λ3 yeast-displayed libraries stained with 1 μM IL-10Rβ monomers in the presence IFN-λR1. (FIG. 1C) Sequences and on-yeast affinity measurements of evolved IFN-λ mutants. (FIG. 1D) IL-10Rβ affinity for the wild-type IFN-λR1/IFN-λ3 or H11-containing binary complexes was determined by surface plasmon resonance. $K_D$ values were determined by fitting to a first order equilibrium binding model.

(FIG. 2A) The structure of the ternary complex reveals the mechanism of IL-10Rβ (gold) recognition of IFN-λ3 H11 (blue) and IFN-λR1 (gray). The IL-10Rβ makes extensive and continuous contacts with H11 at sites 2a, 2b, and site 3 that is composed of stem-stem contacts with the IFN-λR1. Unique to the IFN-λ structure, a large surface area of the cytokine remains surface exposed in the ternary complex. (FIG. 2B) View of IL-10Rβ from the perspective of the IFN-λ3/IFN-λR1 binary. Comparison of the apo IL-10Rβ (pink ribbons) (PDB 3LQM[21]) to the ternary bound conformation (gold ribbons) reveals nearly identical SD1 and SD2 domain orientations and large conformational changes of tyrosine-containing loops 2, 3, and 5.

FIG. 3A-3D: Specific interactions important for stability of the ternary complex. (FIG. 3A) Overview of the IFN-λ3 H11 (blue)/IFN-λR1 (grey)/IL-10Rβ (gold) ternary complex. (FIG. 3B) Open book perspective of the cytokine/receptor and receptor/receptor highlighting the contact surface areas are painted accordingly. The site 3, receptor-receptor, interface is approximately 1400 Å$^2$ and the two cytokine-receptor contact surface areas are each approximately 1700 Å$^2$. (FIG. 3C) Detailed views of the site 2a and site 2b contacts between IFN-λ3 H11 and IL-10Rβ tyrosines 59, 82, and 140. Hydrogen bonds are indicated by dashed black lines. Tyrosines 59 and 82 dock onto pockets on IFN-λ "pinching" the end of the helical bundle (right ribbon on surface). His91 of IFN-λ H11 forms a hydrogen bond with the backbone of the Tyr82 carbonyl IL-10Rβ. (FIG. 3D) Detailed views of the site 3 stem contact between IFN-λR1 and IL-10Rβ. Hydrogen bonds are indicated by dashed black lines.

FIG. 4A-4C: Structural and chemical conservation of IL-10Rβ binding in the IL-10 superfamily. (FIG. 4A) Structures of IL-10 (green) (PDB 1J7V[14]), and IL-22 (orange) (PDB 3DLQ[15]) were aligned to IFN-λ3 H11 (blue ribbon) in the ternary complex structure, highlighting conserved features of IL-10Rβ (gold surface) recognition. IL-10Rβ surface residues within contact distance of H11 are shaded red. IFN residues at which alanine mutations have been shown to negatively impact IL-10Rβ binding are indicated as sticks (right panel). (FIG. 4B) Sequence alignments of the IL-10Rβ-contacting helical regions of IFN-λ3 with the IL-10 and IL-22 cytokines. Residues implicated in IL-10Rβ binding by alanine mutagenesis studies (depicted in FIG. 4a, right, and Extended Data FIG. 3a) are highlighted. (FIG. 4C) View of the IL-10Rβ binding interface modeled on the face of IL-10 and IL-22 using the IFN-λ3 H11 ternary complex. Cytokine residues at the IL-10Rβ interface are colored by chemical properties (red for polar/charged or white for hydrophobic) to highlight the conserved "hydrophobic" pockets in which the IL-10Rβ tyrosines likely dock.

(FIG. 5A) STAT1 activation in Hap1 cells. Curves were fitted to a first-order logistic model. (FIG. 56) Induction of ISG15 in Hap1 cells treated with 5 pM with each interferon for 6 hours as determined by qPCR. (FIG. 5C) Anti-viral activity of IFNs in Huh7.5 cells infected with HCV. (FIG. 5D) Anti-proliferative activity of IFNs in Huh7.5 cells. (FIG. 5E) Anti-proliferative activity of IFNs is enhanced in Huh7.5 cells overexpressing IFN-λR1. (FIG. 5F) Human liver chimeric mice were generated by injecting human hepatoblasts into fah−/−rag2−/−il2rgnull (FRG) mice and infected with 2×10[7] DNA copies of virus obtained from a genotype C eAg negative patient. Human albumin was tracked by ELISA (red circles) and HBV DNA quantified by qPCR (green circles) over 220 days prior to IFN treatment. (FIG. 5G) Mice were treated daily with 10 μg/kg of body weight for four weeks with either vehicle, IFN-λ3, or IFN-λ3 H11. The engineered IFN-λ3 H11 has improved in vivo activity over the wild-type IFN-λ3 (p=0.02).

FIG. 6A-6D: Probing type I IFN function via cytokine engineering and high-throughput functional screening. (FIG. 6A) A site-directed IFN-ω library designed to mutagenize the low affinity IFN-αR1 site was combined with a rationally designed affinity-enhancing Lys152Arg mutation at the IFN-αR2 interface on the cytokine. The SD4 domain of IFN-αR1 was modeled to the complex (3SE4[10]) using the mouse IFN-αR1 structure (PDB 3WCY). (FIG. 6B) 288 clones were screened for activity using a high-throughput functional screen. Displayed IFNs were cleaved from yeast by the site-specific 3C protease. The filtered supernatants were then used to treat VPN53[27] cells to measure AP activity and HCV-infected Huh-7.5 cells to measure AV activity. (FIG. 6C) Functional characterization of phospo-STAT1 signaling, AV and AP potencies as a function of complex stability. Potencies of IFN-mediated activation of STAT1 on Jurkat cells, viral clearance in HCV-infected Huh7.5 cells, and proliferation inhibition of WISH cells were used to determine $EC_{50}$s and plotted as a function of complex stability (left panel). (FIG. 6D) Fold ISG induction as measured by qPCR relative to complex stability.

(FIG. 7A) The wild-type myc-tagged IFN-λ3 (PDB 3HHC) displays on the surface of the yeast (right panel was stained with anti-Myc-647 antibody versus middle panel yeast were left unstained) and (FIG. 7B) binds to IFN-λR1 ($K_D$=400 nM). (FIG. 7C) Location of the H11 mutations (red sticks) in context of the IFN-λ3/IFN-λR1 binary complex, modeled using PDBs 3HHC and 3OG6. (FIG. 7D) IFN-λR1 affinity for the wild-type IFN-λ3 ($K_D$=850 nM) or H11 ($K_D$=150 nM) cytokines was determined by surface plasmon resonance. $K_D$ values were determined by fitting to a first order equilibrium binding model. (FIG. 7E) Size exclusion chromatograph (Superdex S75 column) of the IFN-λ3 H11 ternary complex.

FIG. 8A-8F: Electron density of the lambda-IFN/IFN-λR1/IL-10Rβ ternary complex. The 2Fo-Fc electron density maps are contoured at 1.0 σ. (FIG. 8A) Full electron density map for the lambda complex at 2.85 Å. (FIG. 8B) Close-up view of site 3 hydrogen bonds between loop 5 of IL-10Rβ and IFN-λR1. (FIG. 8C) Close-up view of site 3 hydrogen bonds between the two receptor stems. (FIG. 8D) Close-up view of site 2a near Tyr59 of IL-10Rβ. (FIG. 8E) Close-up view of site 2a near Tyr82 of IL-10Rβ. (FIG. 8F) Close-up view of site 2b near Tyr140 and Trp143 of IL-10Rβ.

(FIG. 9A) View of the IL-10Rβ binding interface of IFN-λ3 H11 mapped onto the structures of other IL-10 superfamily members. Residues that impact IL-10Rβ binding identified through mutagenesis analysis and residues that share hydrogen bonds with IL-10Rβ in the IFN-λ ternary complex structure are shown as sticks. As shown in FIG. 9B, the sequence alignments of the IL-10Rβ-contacting helical regions highlight the lack of sequence conservation in the family.

FIG. 10A-10D: Functional characterization of H11. (FIG. 10A) Induction of six ISGs in Hap1 cells treated with 5 pM of each interferon for 6 hours and measured by qPCR. (FIG. 10B) Anti-proliferative activity of IFNs in three different cell lines before and after lenti-virus transduction of IFN-λR1 receptor followed by sorting by receptor expression. The fold improvement of H11 over the wild-type is shown in the inset. (FIG. 10C) HBV sAg levels were quantified by ELISA and demonstrate H11 reductions were greater than the wild-type treatment (p=0.0083). (FIG. 10D) The human albumin levels were monitored during the course of the 4-week treatment, were stable for all groups and exclude human hepatocyte loss.

FIG. 12A-12D. Synthekine 2 is a hybrid Interferon that dimerizes type I and type III IFN receptors. (FIG. 12A) Table of IFN receptors, their associated JAKs, and STATs activated upon receptor dimerization. (FIG. 12B) Synthekine 2 is a hybrid interferon that dimerizes IFNAR1 and IFNAR1 receptors and their respective JAKs. (FIG. 12C) The Emax of phospho-STAT1 activation by Synthekine 2 (green) is equal to that of type 1 IFN (red) and twice the signal induced by type III IFNs (blue and orange). Error bars represent ±SEM (n=3). (FIG. 12D) Synthekine 2 (green) potently induces the anti-proliferative effect whereas type I IFN (red), type III IFN (blue and orange) or a combination type I and III IFN treatment (black) is ineffective. Error bars represent ±SEM (n=3). Phospho-STAT1 signaling and antiproliferative assays were performed in Hap1 cells which are naturally responsive to both type I and type III IFNs.

DETAILED DESCRIPTION OF THE EMBODIMENTS

Figures 1A, 1B, 1C, 1D:
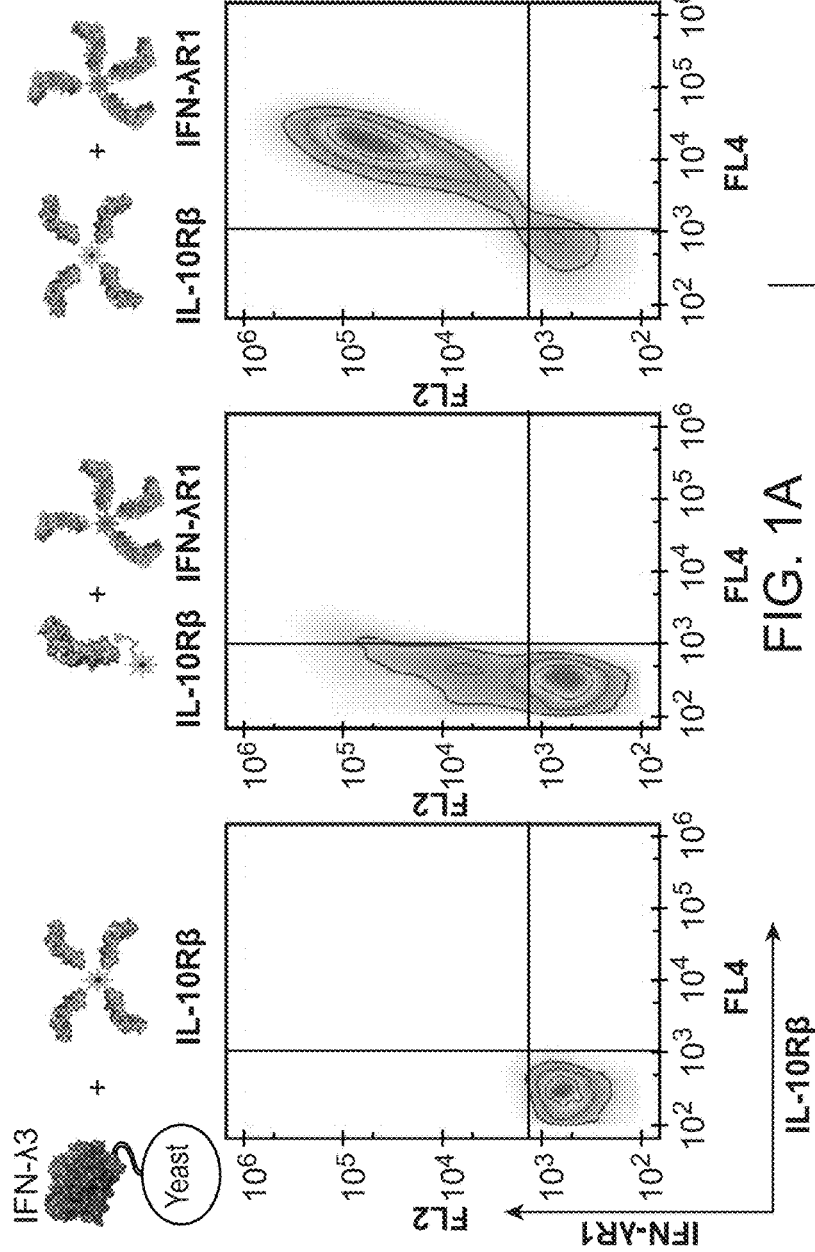
FIG. 1A-1D: Engineering a high-affinity IFN-λ.

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Type III IFN (IFNλ). IFNs are key cytokines in the establishment of a multifaceted antiviral response. Three distinct types of IFNs are now recognized (type I, II, and III) based on their structural features, receptor usage and biological activities. IFNs and IL-10-related cytokines all signal via receptors that share common motifs in their extracellular domains, known as the class II cytokine receptor family (CRF2). In humans, a family of distinct but closely related IFNλ proteins, IFNλ1, λ2, λ3, λ4 (also known as IL-29, IL-28A, IL-28B, respectively) form the type III IFN family.

Figure 11:
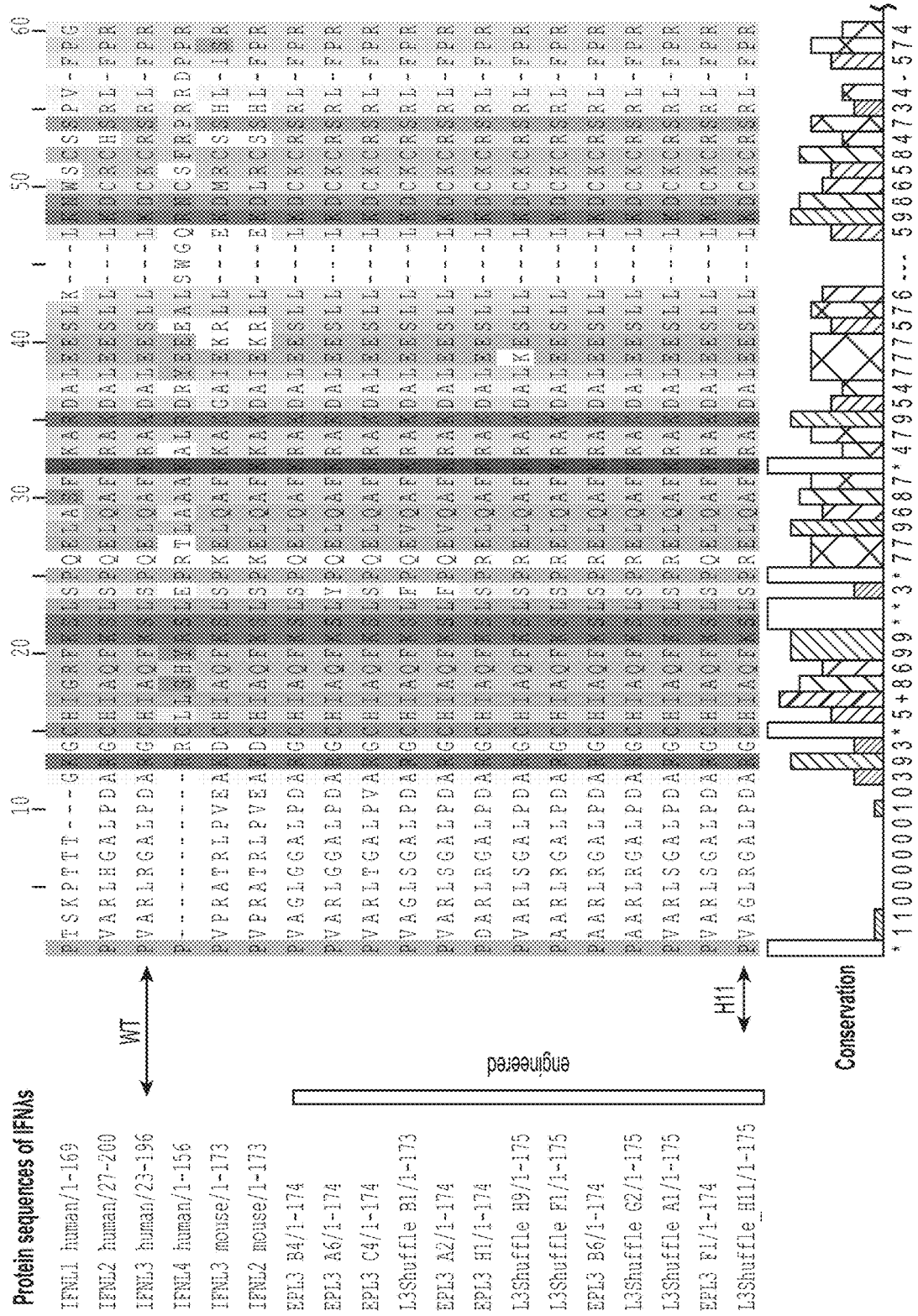
FIG. 11. Alignment of sequences, shown are SEQ ID NO:1-15.

The sequences of the human and mouse IFNλ proteins are provided for reference in the sequence listing and in FIG. 11. The reference sequences of the wild-type proteins may be provided as the mature form of the protein, as noted in FIG. 11. The reference sequences include human IFNλ1 (SEQ ID NO:1), human IFNλ2 (SEQ ID NO:2), human IFNλ3 (SEQ ID NO:3), and human IFNλ4 (SEQ ID NO:4). Mouse reference sequences provided herein are mouse IFNλ3 (SEQ ID NO:5), mouse IFNλ2 (SEQ ID NO:6). The sequence of human IFNλ3 corresponds to Genbank reference XP_005258822.1. The affinity matured variant proteins may include all or a part of the reference sequence, with appropriate amino acid substitutions. In certain embodiments the protein is truncated by deletion of residues 1-11 of a reference IFNλ3 protein.

In some embodiments of the invention, an IFNλ variant polypeptide is provided, which polypeptide comprises one or more amino acid changes relative to a wild-type IFNλ protein, including without limitation relative to IFNλ3, which changes abrogate binding to IL-10Rβ. In some embodiments the amino acid changes are substitutions at one, two or three of positions: Q26, Q99, H102, relative to SEQ ID NO:3. In some embodiments an amino acid change, including an amino acid substitution, is made at all 3 of Q26, Q99, H102. In some embodiments the amino acid change is a non-conservative substitution, e.g. a substitution to an A, G, S, F, L, I, V, etc. residue. In some embodiments the amino acid change is one or more of Q26A, Q99A, H102A.

In some embodiments an IFNλ variant polypeptide is provided, which polypeptide comprises one or more amino acid changes relative to a wild-type IFNλ protein, including without limitation relative to IFNλ3, which enhances binding to IFNλR1. These changes are optionally combined with amino acid substitutions that abrogate binding to IL-10Rβ. In some embodiments the amino acid changes are substitutions at one, two, or three of positions: H131, T161, V174, relative to SEQ ID NO:3. In some embodiments an amino acid change, including a substitution, is made at all 3 of H131, T161, V174. In some embodiments the amino acid changes are the substitutions H131R, T161A, V174E. Such IFNλ variants may be used, without limitation, as the IFNλR1 binding arm of a synthekine.

The specific set of mutations in H11, relative to SEQ ID NO:3, are Q26R, E84D, H131R, T161A, V174E. The dominant negative variant H11DN, which binds to ILFλR1 but not to IL-10Rβ comprises the set of mutations Q26A, Q99A, H102A, H131R, T161A, V174E.

The IFNλ proteins bind and signal through a receptor complex composed of the IFNλR1 chain (also known as IL-28RA) and the shared IL-10Rβ chain which is also a part of the receptor complexes for IL-10, IL-22, and IL-26. Signaling through either IFNλ or IFNα receptor complexes results in the activation of the Jak-STAT signal transduction cascade. IFNλ binds initially to the IFNλR1 chain, and the binary complex formed by the association of IFNλ with the IFNλR1 chain causes a rapid conformational change that facilitates recruitment of the second receptor chain, IL-10Rβ, to the complex. Once assembly of the ternary complex is complete, the receptor-associated Janus tyrosine kinases, Jak1 and Tyk2, mediate trans-phosphorylation of the receptor chains which results in the formation of phosphotyrosine-containing peptide motifs on the intracellular domain (ICD) of the IFNλR1 chain that provide transient docking sites for cytosolic STAT proteins, including STAT1 and STAT2. The biological activities induced by type III IFNs include induction of antiviral activity and up-regulation of major histocompatibility complex (MHC) class I antigen expression.

Cells of epithelial origin appear to be the primary targets for IFNλ because, unlike leukocytes, they express significant levels of IFNAR1. The membrane expression pattern of IFNλR1 appears to be very similar to IL-22R1, and like the IL-22R1 chain, IFNAR1 is not expressed on leukocytes.

IFNλ can activate host antitumor mechanisms that inhibit the growth of certain tumors. The antiproliferative activity of the IFNλs has been demonstrated using several target cell types, including melanoma, intestinal epithelial cells and the human glioblastoma cell line, LN319. The ability of IFNλs to induce antiproliferative activity in target cells may depend on the relative levels of IFNAR1.

Type I IFN. The human type I IFN family consists of multiple IFNα members, single IFNβ, epsilon, kappa, and omega subtypes. These cytokines induce antiviral responses by binding a common receptor, the IFNAR1/IFNAR2, expressed on a wide variety of cell types. IFNα proteins are produced by leukocytes. They are mainly involved in innate immune response against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9. IFN-β proteins are produced in large quantities by fibroblasts. They have antiviral activity that is involved mainly in innate immune response. Two types of IFN-β have been described, IFN-β1 (IFNB1) and IFN-β3 (IFNB3). IFNε, κ, ω appear, at this time, to come in a single isoform in humans. IFN-ω is released by leukocytes at the site of viral infection or tumors.

The type I interferon (IFN) receptor (IFNAR) is comprised, as other cytokine receptors, of two components, designated IFNAR1 and IFNAR2. It is unique among cytokine receptors in the number of cognate ligands. The type I IFN receptors are distinct from those required for the type II IFNγ (IFNGR1 and IFNGR2) and type III IFNs (IFNλR and IL10Rβ). Most cell types bind IFNs, with large variation in the number of binding sites (200-10,000/cell) and binding affinities. Various type I IFNs bind to IFNAR2 with Kd values mostly in the nM range (from 0.1 to 1000 nM) and bind to IFNAR1 with Kd mostly in the μM range (from 0.05 to 10 μM).

The type I IFN receptor, typical of class II hCR, lack intrinsic kinase activity and thus rely on associated Janus kinases (JAKs) to phosphorylate receptors and signal transducing molecules, such as STAT proteins, after ligand-induced receptor clustering. IFNAR1 is preassociated with Tyk2, which also stabilizes IFNAR1 cell surface expression levels.

For convenience, a reference sequence of the mature human IFNω protein is provided in the sequence listing as SEQ ID NO:21. In some embodiments, an IFNω polypeptide is provided that has abrogated binding to IFNAR2. In some embodiments the amino acid changes are substitutions at one, two, three or four of positions: R14, L32, R35, K152, relative to SEQ ID NO:21. In some embodiments an amino acid change, including an amino acid substitution, is made at all 4 of R14, L32, R35, K152. In some embodiments the amino acid change is a non-conservative substitution, e.g. a substitution to an A, G, S, F, L, I, V, etc. residue. In some embodiments the amino acid change is one or more of R14A, L32A, R35A, K152A, including all four changes.

A specific IFNω variant polypeptide that has reduced binding to IFNAR2 is provided in the sequence listing as SEQ ID NO:22, which variant may be referred to as IFNWDN2. The set of amino acid changes in IFNWDN2, relative to SEQ ID NO:21, are R14A, L32A, R35A, K152A.

The terms "specific binding," "specifically binds," and the like, refer to non-covalent or covalent preferential binding to a molecule relative to other molecules or moieties in a solution or reaction mixture (e.g., an interferon binding to a cognate receptor). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-5}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The term "ablation" of binding refers to a reduction in binding of a ligand to a receptor, such that signaling from the receptor in the presence of the ligand is reduced to substantially background levels, e.g. a reduction of at least about 10-fold relative to the level of signaling in the presence of the same concentration of the native ligand, a reduction of at least about 100-fold, a reduction of at least about $10^3$-fold, or more.

As used herein, the term "infection" refers to any state in at least one cell of an organism (i.e., a subject) is infected by an infectious agent. As used herein, the term "infectious agent" refers to a foreign biological entity, i.e. a pathogen, that reproduces in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions.

Hepatitis Virus. The hepatitis viruses include a range of unrelated and often highly unusual human pathogens. Hepatitis A virus (HAV), classified as hepatovirus, is a small, unenveloped symmetrical RNA virus which shares many of the characteristics of the picornavirus family, and is the cause of infectious or epidemic hepatitis transmitted by the fecal-oral route. Hepatitis B virus (HBV), a member of the hepadnavirus group, double-stranded DNA viruses which replicate, unusually, by reverse transcription. Hepatitis B virus is endemic in the human population and hyperendemic in many parts of the world. A number of variants of this virus have been described. Hepatitis C virus (HCV), is an enveloped single-stranded RNA virus which appears to be distantly related (possibly in its evolution) to flaviviruses, although hepatitis C is not transmitted by arthropod vectors. Several genotypes have been identified. Infection with this more recently identified virus is common in many countries. Hepatitis C virus is associated with chronic liver disease and also with primary liver cancer in some countries. Hepatitis D virus (HDV) is an unusual, single-stranded, circular RNA virus with a number of similarities to certain plant viral satellites and viroids. This virus requires hepadna virus helper functions for propagation in hepatocytes, and is an important cause of acute and severe chronic liver damage in many regions of the world. Hepatitis E virus (HEV), the cause of enterically-transmitted non-A, non-B hepatitis, is another non-enveloped, single-stranded RNA virus, which shares many biophysical and biochemical features with caliciviruses. Hepatitis E virus is an important cause of large epidemics of acute hepatitis in the subcontinent of India, Central and Southeast Asia, the Middle East, parts of Africa and elsewhere.

The terms "hepatitis C virus," "HCV," "non-A non-B hepatitis," or "NANBH" are used interchangeably herein, and include any "genotype" or "subgenotype" (also termed "subtype") of the virion, or portion thereof (e.g., a portion of the E2 protein of genotype 1a of HCV), that is encoded by the RNA of hepatitis C virus or that occurs by natural allelic variation. The HCV genome comprises a 5'-untranslated region that is followed by an open reading frame (ORF) that codes for about 3,010 amino acids. The ORF runs from nucleotide base pair 342 to 8,955 followed by another untranslated region at the 3' end. There are about six distinct HCV genotypes (e.g., genotypes 1, 2, 3, 4, 5, and 6) that are categorized by variations in the core protein and over 80 subgenotypes which exhibit further variation within each genotype, some of which include: 1a; 1b; 1c; 2a; 2b; 2c; 3a; 3b; 4a; 4b; 4c; 4d; 4e; 5a; and 6a.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

"Polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived.

As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of an polypeptide. Polypeptides suitable for use can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, particularly rat or human, from any source whether natural, synthetic, semi-synthetic or recombinant. In general, polypeptides comprising a sequence of a human polypeptide are of particular interest.

The term "derived from" indicates molecule that is obtained from the indicated source (e.g., when a protein directly purified from a cell, the protein is "derived from" the cell) or information is obtained from the source, e.g. nucleotide or amino acid sequence, from which the molecule can be synthesized from materials other than the source of information.

The term "isolated" indicates that the recited material (e.g., polypeptide, nucleic acid, etc.) is substantially separated from, or enriched relative to, other materials with which it occurs in nature (e.g., in a cell). A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. As will be evidence from the context in which the term is used, subject and patient may refer to a subject or patient infected with a virus, having cancer, etc.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Variants. IFN polypeptides, e.g. IFN sequences providing binding domains in IFN, synthekines, may also include derivatives, variants, and biologically active fragments of polypeptides described above, e.g. variants of native ligands. A "variant" polypeptide means a biologically active polypeptide as defined below having less than 100% sequence identity with a provided sequence. Such variants include polypeptides comprising one or more amino acid modifications, e.g., insertions, deletions or substitutions, as compared to the provided sequence, e.g., wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

A "functional derivative" of a sequence is a compound having a qualitative biological property in common with an initial sequence. "Functional derivatives" include, but are not limited to, fragments of a sequence and derivatives of a sequence, provided that they have a biological activity in common. The term "derivative" encompasses both amino acid sequence variants of polypeptide and covalent modifications thereof.

Binding domains for use in the subject compositions and methods may be modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

An IFNλ synthekine may be fused or bonded to an additional polypeptide sequence. Examples include immunoadhesins, which combine a synthekine with an immunoglobulin sequence particularly an Fc sequence, and epitope tagged polypeptides, which comprise a native inhibitors polypeptide or portion thereof fused to a "tag polypeptide". The tag polypeptide is short enough such that it does not interfere with biological activity of the native polypeptide. Suitable tag polypeptides generally have at least six amino acid residues and usually also between about 6-60 amino acid residues. The synthekine or IFN, may also be fused or combined in a formulation, or co-administered with an agent that enhances activity, e.g. cytokines, growth factors, chemotherapeutic agents, immunosuppressants, etc.

Linker. The binding domains of a synthekine may be separated by a linker, e.g. a polypeptide linker, or a non-peptidic linker, etc. The amino acid linkers that join domains can play an important role in the structure and function of multi-domain proteins. There are numerous examples of proteins whose catalytic activity requires proper linker composition. In general, altering the length of linkers connecting domains has been shown to affect protein stability, folding rates and domain-domain orientation (see George and Hering (2003) Prot. Eng. 15:871-879). The length of the linker in the synthekine, and therefore the spacing between the binding domains, can be used to modulate the signal strength of the synthekine, and can be selected depending on the desired use of the synthekine. The enforced distance between binding domains of a synthekine can vary, but in certain embodiments may be less than about 100 angstroms, less than about 90 angstroms, less than about 80 angstroms, less than about 70 angstroms, less than about 60 angstroms, less than about 50 angstroms, less than about 40 angstroms, less than about 30 angstroms, less than about 20 angstroms.

In some embodiments the linker is a rigid linker, in other embodiments the linker is a flexible linker. In some embodiments, the linker moiety is a peptide linker. In some embodiments, the peptide linker comprises 2 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser. Suitable linear peptides include poly glycine, polyserine, polyproline, polyalanine and oligopeptides consisting of alanyl and/or serinyl and/or prolinyl and/or glycyl amino acid residues. In some embodiments, the peptide linker comprises the amino acid sequence selected from the group consisting of $Gly_9$, $Glu_5$, $Ser_9$, $Gly_5$-Cys-$Pro_2$-Cys, $(Gly_4$-Ser$)_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and $Gly_9$-Pro-Ser-Cys-Val-Pro-Leu-Met-Arg-Cys-Gly-Gly-Cys-Cys-Asn. In one embodiment a linker comprises the amino acid sequence GSTSGSGKSSEGKG, or (GGGGS)n, where n is 1, 2, 3, 4, 5, etc.; however many such linkers are known and used in the art and may serve this purpose.

Synthekines can be provided in single-chain form, which means that the binding domains are linked by peptide bonds through a linker peptide. In other embodiments, the binding domains are individual peptides and can be joined through a non-peptidic linker.

Chemical groups that find use in linking binding domains include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hyrodrazone, lipids, and the like, as known in the art.

The linkage between binding domains may comprise spacers, e.g. alkyl spacers, which may be linear or branched, usually linear, and may include one or more unsaturated bonds; usually having from one to about 300 carbon atoms; more usually from about one to 25 carbon atoms; and may be from about three to 12 carbon atoms. Spacers of this type may also comprise heteroatoms or functional groups, including amines, ethers, phosphodiesters, and the like. Specific structures of interest include: $(CH_2CH_2O)n$ where n is from 1 to about 12; $(CH_2CH_2NH)n$, where n is from 1 to about 12; $[(CH_2)n(C=O)NH(CH_2)_m]_z$, where n and m are from 1 to about 6, and z is from 1 to about 10; $[(CH_2)nOPO_3(CH_2)_m]_z$ where n and m are from 1 to about 6, and z is from 1 to about 10. Such linkers may include polyethylene glycol, which may be linear or branched.

The binding domains may be joined through a homo- or heterobifunctional linker having a group at one end capable of forming a stable linkage to the hydrophilic head group, and a group at the opposite end capable of forming a stable linkage to the targeting moiety. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP); N, N'-(1,3-phenylene) bismaleimide; N, N'-ethylene-bis-(iodoacetamide); or 4-(N-maleimidomethyl)-cyclohexane-1-carboxylic acid N-hydroxysuccinimide ester (SMCC); m-maleimidobenzoyl-N-hydroxysuccinimide ester (MBS), and succinimide 4-(p-maleimidophenyl) butyrate (SMPB), an extended chain analog of MBS. The succinimidyl group of these cross-linkers reacts with a primary amine, and the thiol-reactive maleimide forms a covalent bond with the thiol of a cysteine residue.

Other reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); disdiazobenzidine (which reacts primarily with tyrosine and histidine); O-benzotriazolyloxy tetramethuluronium hexafluorophosphate (HATU), dicyclohexyl carbodiimde, bromo-tris (pyrrolidino) phosphonium bromide (PyBroP); N,N-dimethylamino pyridine (DMAP); 4-pyrrolidino pyridine; N-hydroxy benzotriazole; and the like. Homobifunctional cross-linking reagents include bis-maleimidohexane ("BMH").

Antibody. As used herein, the term "antibody" refers to a polypeptide that includes canonical immunoglobulin sequence elements sufficient to confer specific binding to a particular target antigen. Antibodies that bind to an extracellular domain of one or more of the receptors: IL-10Rβ, IFNλR1, IFNAR1, IFNAR2 are of interest. In some embodiments an antibody is a bispecific antibody binding to the extracellular domains of IFNλR1 and IFNAR1; or IFNλR1 and IFNAR2.

As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure.

The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation.

Any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, antibody sequence elements are humanized, primatized, chimeric, etc., as is known in the art.

Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., ZYBODIES®, etc.), single chain Fvs, Fabs, Small Modular ImmunoPharmaceuticals ("SMIPs™"), single chain or Tandem diabodies (TANDAB®), VHHs, ANTICALINS®, NANOBODIES®, minibodies, BITE®s, ankyrin repeat proteins or DARPINs®, AVIMERS®, a DART, a TCR-like antibody, ADNECTINS®, AFFILINS®, TRANS-BODIES®, AFFIBODIES®, a TRIMERX®, MicroProteins, FYNOMERS®, CENTYRINS®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload (e.g., a detectable moiety, a therapeutic moiety, a catalytic moiety, etc.), or other pendant group (e.g., poly-ethylene glycol, etc.)

Small Molecule Compositions. synthekines also include organic molecules, preferably small organic compounds having a molecular weight of more than 50 and less than about 20,000 daltons. Useful synthekines are identified by, for example, a screening assay in which molecules are assayed for high affinity binding to one or both of the extracellular domains of IL-10Rβ, IFNλR1, IFNAR1, IFNAR2. In some embodiments the molecule binds to the extracellular domains of IFNλR1 and IFNAR1; or IFNλR1 and IFNAR2 are of interest. A molecule can provide for a binding moiety that will be joined to another binding moiety, or joined to a binding domain as described above for polypeptide agents.

Candidate synthekines comprise functional groups necessary for structural interaction with receptor ECD, particularly hydrogen bonding, and typically include at least an amine, carbonyl, hydroxyl or carboxyl group, preferably at least two of the functional chemical groups. The candidate synthekines often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate synthekines are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to receptor polypeptide(s) of interest. The binding assays usually involve contacting a receptor ECD with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in Neurotransmitter Receptor Binding (Yamamura, H. I., et al., eds.), pp. 61-89.

Certain screening methods involve screening for a compound that modulates signaling activity. Such methods may involve conducting cell-based assays in which test compounds are contacted with one or more cells expressing and then detecting and an increase in expression of responsive genes, detecting changes in various adapter proteins, Jak, STAT(s), and the like.

The level of expression or activity can be compared to a baseline value. As indicated above, the baseline value can be a value for a control sample or a statistical value that is representative of expression levels for a control population. Expression levels can also be determined for cells that do not express a receptor, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal or in a cell culture model, that serves as a model for humans. The animal models utilized in validation studies generally are mammals. Specific examples of suitable animals include, but are not limited to, primates, mice, and rats.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Other definitions of terms appear throughout the specification.

Protein Compositions

Variant IFNλ polypeptides and synthekines derived therefrom are provided. Sythekines result in a measurable increase in the level of signaling by the targeted pathway, with the proviso that a different profile of signals are activated relative to a native ligand. Key features are that the synthekine specifically binds to 2 or more distinct extracellular domains (ECD) of cell surface receptors. As used herein, IFNλ, synthekines bind to one of IFNλR1 or IL-10Rβ. In some embodiments the second ECD is IFNAR1 or IFNAR2.

A synthekine can be any molecule, e.g. protein or pharmaceutical that has the desired binding properties, and may comprise variant IFNλ and Type I IFN polypeptides. Small molecules, which may be less than about 15 Kd, are of interest and can be developed through compound screening as described herein. Polypeptides are also of interest. In addition, certain synthekines may comprise both a polypeptide region or domain and a non-polypeptide region or domain. A synthekine can be a polypeptide, where binding domains for two different receptor extracellular domains are linked. A polypeptide synthekine may be a single chain, dimer, or higher order multimer. The binding domains may be directly joined, or may be separated by a linker, e.g. a polypeptide linker, or a non-peptidic linker, etc.

In some embodiments, one or all of the binding domain(s) comprise the binding domain of a native ligand, i.e. a Type I IFN, e.g. IFNA1, IFNA2, IFNA4, IFNA5, IFNA6, IFNA7, IFNA8, IFNA10, IFNA13, IFNA14, IFNA16, IFNA17, IFNA21, IFNβ, IFNε, IFNκ, IFNω joined to a Type III IFN, i.e. IFNL1, IFNL2, IFNL3, and IFNL4; where the binding domain does not activate the native receptor for the ligand. For example, a binding domain may comprise targeted amino acid substitutions that result in a lack of binding to one of the native receptor polypeptides, but not the other. Many such modified binding domains are known in the art, and can, for example, result in dominant negative mutations with respect to the native receptor configuration. Specific embodiments of such polypeptides are described herein, and include without limitation an IFNλ polypeptide with abrogated binding to IL-10Rβ as a result of amino acid changes at one or more of residues Q26, Q99, H102, relative to SEQ ID NO:3; and an IFNω polypeptide with abrogated binding to IFNAR2 as a result of amino acid changes at one or more of residues R14, L32, R35, K152, relative to SEQ ID NO:21.

In various other embodiments, the binding domain may be an antibody, or a binding portion derived therefrom, that specifically binds to one chain of a receptor.

In certain embodiments an IFNλ synthekine is a fusion protein comprising an IFNλ variant polypeptide that binds to IFNλR1 but not IL-10Rβ and a Type I IFN, including without limitation an IFNω variant polypeptide, that binds to IFNAR1 but not IFNAR2. A hybrid protein comprising the IFNλ protein set forth in SEQ ID NO:20 (H11DN) and the IFNω variant set forth in SEQ ID NO:22 (IFNWDN2), which may be fused through a short polypeptide linker, is provided as an example. The synthekine thus created then compels formation of an IFNλR1/IFNAR1 receptor dimer. This dimer recapitulates the JAK1/TYK2 pairing used by the natural IFNλR1 dimer, except it replaces the Tyk2 of IL-10Rβ with that of IFNAR1. Ablation of binding of IL-10Rβ to IFNλ, and IFNAR2 to IFNω may be accomplished by introducing mutations into the respective receptor binding sites. In other embodiments an IFNλ synthekine is engineered to ablate binding of IL-10Rβ to IFNλ, and one of IFNAR1 or IFNAR2 to a Type I IFN, e.g. IFNω, which also results in a novel Tyk2/Jak1 pairing.

In other embodiments an IFNλ synthekine binds to one of IFNλR1 or IL-10Rβ; and the ECD of a receptor that provides for JAK/STAT signaling, including without limitation, μc, γc, IL-3Rα, βIL-3R, GM-CSFRα, IL-5Rα, CNTFα, CRLF1, LIFRα, gp130, IL-6Rα, IL-11Rα, OSMRμ, IL-2Rα, IL-2Rβ, IL-2Rγ, IL-4Rα, IL-7Rα, IL-9Rα, IL-13Rα, IL-15Rα, IL-21Rα, IFNAR2, IL-23R, EpoR, IL-12Rβ, IFNAR1, G-CSFR, c-MPLR. See application U.S. provisional 62/479,993, herein specifically incorporated by reference.

Compositions and methods are also provided relating to affinity matured (variant) Type III interferons. The variant interferons comprise one or more amino acid substitutions relative to the wild-type protein, e.g. relative to the reference sequences set forth in SEQ ID NO:1-6, which changes alter the affinity of the variant interferon for a cognate receptor. A variant protein may comprise a full-length sequence with reference to the wild-type sequences provided herein, or may be a fragment or truncated version. In certain embodiments, residues 1-11 of SEQ ID NO:3 are truncated from the final form of the protein.

The variant interferons, relative to the native protein, may have increased binding with at least a 5-fold increase in affinity, at least a 10 fold increase in affinity, and may have at least a 20-fold increase in affinity or more toward IFNλR1 or IL-10Rβ; or may have at least a 5-fold decrease in affinity, at least a 10 fold decrease in affinity, and may have at least a 20-fold decrease in affinity or more toward IFNλR1 or IL-10Rβ. One or more amino acid residues may be altered to modify binding to achieve a more favored on-rate of binding, a more favored off-rate of binding, or both, such that an optimized binding constant is achieved. Affinity maturation techniques are well known in the art and can be used to alter the binding region(s), followed by screening of the resultant binding molecules for the desired change in binding.

In some embodiments, a variant Type III interferon is derived from human IFN-λ3. In some embodiments, amino acid substitutions are made that increase affinity for IL-10Rμ. The affinity of the variant interferon for IL-10Rμ may be less than about 5 μM Kd, less than about 1 μM Kd, less than about 750 nM Kd, less than about 500 nM Kd. In some embodiments, the amino acid substitution is made at one or more of residues Q26, E84, H131, T161 and V174, where numbering is made relative to SEQ ID NO:3. Where the modification is made to a sequence other than SEQ ID NO:3, reference made be made to the provided sequence alignment in FIG. 11, to determine the corresponding amino acid in SEQ ID N01, 2, 4, 5 or 6.

In some embodiments, the one or more amino acid substitutions are made with at least one residue involved in contacts between the Type III interferon and IL-10Rμ. In certain embodiments an amino acid substitution is at one or both of Q26 and E84. In some embodiments the amino acid substitution is Q26R and/or E84D. Additional substitutions include, without limitation, H131R, T161A and V174E. In some embodiments the variant comprises the sequence of SEQ ID NO:19, or a fragment thereof, e.g. a truncation of amino acid residues 1-11.

In some embodiments the one or more amino acid substitutions are made with at least one residue involved in contacts between the Type III interferon and IFNλR1 receptor. In certain embodiments an amino acid substitution is at position T161. In some embodiments the amino acid substitution is T161A.

The modified interferons may comprise a sequence set forth in any of SEQ ID NO:7-20, and may comprise one or more amino acid substitutions set forth in SEQ ID NO:7-20 relative to the reference sequence SEQ ID NO:3. In some embodiments the protein is truncated relative to any of SEQ ID NO:7-20 by deletion of amino acid residues 1-11.

The enhanced affinity of the variant protein may be manifested in increased activity. For example, in a biological system for reducing viral load, the variant interferon may reduce virus titer, e.g. hepatitis virus titer, over a period of from about 5-10 days by about 2-fold, by about 5-fold, by about 10-fold or more relative to the wild-type protein. In a cell culture system, the variant interferon can provide for an increase in induced gene expression, pSTAT1 signaling, and/or decreased virus replication by about 2-fold, by about 5-fold, by about 10-fold or more relative to the wild-type protein.

Embodiments of the invention include isolated IFNλ synthekines, variant interferons and derivatives and fragments thereof, pharmaceutical formulations comprising one or more of the IFNλ synthekines or affinity matured interferons; and cell lines that produce these IFNλ, synthekines or affinity matured interferons.

The IFNλ synthekines or IFNλ variant polypeptides may be chemically modified with one or more polyethylene glycol moieties, i.e., PEGylated; or with similar modifications, e.g. PASylated The PEG molecule or PAS molecule is conjugated to one or more amino acid side chains of the interferon. In some embodiments, the PEGylated or PASylated interferon contains a PEG or PAS moiety on only one amino acid. In other embodiments, the PEGylated or PASylated interferon contains a PEG or PAS moiety on two or more amino acids, e.g., attached to two or more, five or more, ten or more, fifteen or more, or twenty or more different amino acid residues. In some embodiments, the PEG or PAS chain is 2000, greater than 2000, 5000, greater than 5,000, 10,000, greater than 10,000, greater than 10,000, 20,000, greater than 20,000, and 30,000 Da. The polypeptide may be coupled directly to PEG or PAS (i.e., without a linking group) through an amino group, a sulfhydryl group, a hydroxyl group, or a carboxyl group.

The IFNλ synthekines or IFNλ variant polypeptides formulations of the present invention may be used to treat various conditions, for example virus infection, including without limitation hepatitis virus infection, liver diseases associated with virus infection, and cancers responsive to IFN-λ. IFNλ synthekines or IFNλ, variant polypeptides formulations may comprise one or more IFNλ synthekines or IFNλ variant polypeptides as set forth here, e.g. a cocktail of two or more IFNλ synthekines or IFNλ variant polypeptides; a combination of a IFNλ synthekines or IFNλ variant polypeptides and one or more of an α-IFN, a β-IFN or a γ-IFN; etc. Combinations may also be made with antiviral drugs, chemotherapeutics, immune-oncology agents, and the like. Antiviral agents includes pegylated interferon α, ribivarin, etc. In another example, the antibody is administered together with a polyclonal gamma-globulin (e.g., human gammaglobulin). In another example, the antibody is administered before, after, or contemporaneously with a HCV vaccine. These are generally used in the dosages and with administration routes as used hereinbefore or about from 1 to 99% of the heretofore employed dosages.

The IFNλ synthekines or IFNλ variant polypeptide formulation is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the interferon formulation may be suitably administered by pulse infusion, particularly with declining doses of the interferon.

For the prevention or treatment of disease, the appropriate dosage of IFNλ synthekines or IFNλ variant polypeptides will depend on the type of disease to be treated, the severity and course of the disease, whether the interferon is administered for preventive purposes, previous therapy, the patient's clinical history and response to the interferon, and the discretion of the attending physician. The IFNλ synthekines or IFNλ variant polypeptides is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more IFNλ synthekines or IFNλ variant polypeptides in a formulation of the invention as described above. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Therapeutic formulations comprising one or more proteins of the invention are prepared for storage by mixing the interferon having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The interferon composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the IFNλ synthekines or IFNλ variant polypeptide to be administered will be governed by such considerations, and is the minimum amount necessary to reduce virus titer in an infected individual, reduce proliferation of cancer cells, reduce tumor burden, etc.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of interferon fragments, or in the use of IFNλ synthekines or IFNλ variant polypeptides. The dosage may also be varied for localized administration, or for systemic administration, e.g. i.m., i.p., i.v., and the like.

An exemplary treatment regime entails administration daily, semi-weekly, weekly, once every two weeks, once a month, etc. In another example, treatment can be given as a continuous infusion. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

A pharmaceutically effective dose is that dose required to prevent, inhibit the occurrence, or treat (alleviate a symptom at least to some extent) of a disease state, e.g. to reduce virus titer in an infected individual, to reduce proliferation of cancer cells, etc. The pharmaceutically effective dose depends on the type of disease, the composition used, the route of administration, the type of subject being treated, subject-dependent characteristics under consideration, concurrent medication, and other factors that those skilled in the medical arts will recognize. Generally, an amount between 0.1 mg/kg and 100 mg/kg body weight/day of active ingredients is administered.

Formulations and methods of delivery of agents to the liver are known in the art, see, e.g., Wen et al., 2004, *World J. Gastroenterol.* 10:244-9; Murao et al., 2002, Pharm. Res. 19:1808-14; Liu et al., 2003, *Gene Ther.* 10:180-7; Hong et al., 2003, *J. Pharm. Pharmacol.* 54; 51-8; Herrmann et al., 2004, *Arch. Virol.* 149:1611-7; and Matsuno et al., 2003, *Gene. Ther.* 10:1559-66.

Formulations and methods of delivery of agents to the skin or mucosa are known in the art. Such delivery systems include, e.g., aqueous and nonaqueous gels, creams, multiple emulsions, microemulsions, liposomes, ointments, aqueous and nonaqueous solutions, lotions, patches, suppositories, and tablets, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Oral administration can be accomplished using pharmaceutical compositions containing an agent of interest formulated as tablets, lozenges, aqueous or oily suspensions, dispersible powders or granules, emulsion, hard or soft capsules, or syrups or elixirs. Such oral compositions can contain one or more such sweetening agents, flavoring agents, coloring agents or preservative agents in order to provide pharmaceutically elegant and palatable preparations. Tablets, which can be coated or uncoated, can be formulated to contain the active ingredient in admixture with non-toxic pharmaceutically acceptable excipients, e.g., inert diluents; such as calcium carbonate, sodium carbonate, lactose, calcium phosphate or sodium phosphate; granulating and disintegrating agents, for example, corn starch, or alginic acid; binding agents, e.g., starch, gelatin or acacia; and lubricating agents, for example magnesium stearate, stearic acid or talc. Where a coating is used, the coating delay disintegration and absorption in the gastrointestinal tract and thereby provide a sustained action over a longer period.

Where the formulation is an aqueous suspension, such can contain the active agent in a mixture with a suitable excipient(s). Such excipients can be, as appropriate, suspending agents (e.g., sodium carboxymethylcellulose, methylcellulose, hydropropyl-methylcellulose, sodium alginate, polyvinylpyrrolidone, gum tragacanth and gum acacia); dispersing or wetting agents; preservatives; coloring agents; and/or flavoring agents.

Suppositories, e.g., for rectal administration of agents, can be prepared by mixing the agent with a suitable non-irritating excipient that is solid at ordinary temperatures but liquid at the rectal temperature and will therefore melt in the rectum to release the drug. Such materials include cocoa butter and polyethylene glycols.

Dosage levels can be readily determined by the ordinarily skilled clinician, and can be modified as required, e.g., as required to modify a subject's response to therapy. In general dosage levels are on the order of from about 0.1 mg to about 140 mg per kilogram of body weight per day. The amount of active ingredient that can be combined with the carrier materials to produce a single dosage form varies depending upon the host treated and the particular mode of administration. Dosage unit forms generally contain between from about 1 mg to about 500 mg of an active ingredient.

Methods of Use

The invention includes methods of treating disease in a subject by administering to the subject an IFNλ synthekines or IFNλ variant polypeptides as described herein in an amount effective to inhibit virus infection or replication, to inhibit tumor cell growth, proliferation, etc., e.g., infection, virus or tumor-mediated symptoms or morbidity. Such diseases may include various liver conditions associated with hepatitis virus infection. Included in the treatment of patients before, during and/or after liver or kidney transplant. Treatment may include the use of the IFN, synthekines or IFNλ variant polypeptides of the invention as a single agent, or as an agent in combination with additional antiviral or anti-cancer agents, including drugs, additional antibodies, vaccines, and the like.

In some embodiments the infection is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral, hepadna, lentiviral, etc. pathogens, e.g. HIV-1; HIV-2, HTLV, Fly, SIV, etc., Hepatitis A, B, C, D, E virus, etc. In some embodiments, the methods of the invention involve diagnosis of a patient as suffering from an infection; or selection of a patient previously diagnosed as suffering from an infection; treating the patient with a regimen of variant type III interferon therapy, optionally in combination with an additional therapy; and monitoring the patient for efficacy of treatment. Monitoring may measure clinical indicia of infection, e.g. fever, white blood cell count, etc., and/or direct monitoring for presence of the pathogen. Treatment may be combined with other active agents. Cytokines may also be included, e.g. interferon γ, tumor necrosis factor α, interleukin 12, etc. Antiviral agents, e.g. acyclovir, gancyclovir, etc., may also be used in treatment. Subjects suspected of having an infection, including an HCV infection, can be screened prior to therapy. Further, subjects receiving therapy may be tested in order to assay the activity and efficacy of the treatment. Significant improvements in one or more parameters is indicative of efficacy. It is well within the skill of the ordinary healthcare worker (e.g., clinician) to adjust dosage regimen and dose amounts to provide for optimal benefit to the patient according to a variety of factors (e.g., patient-dependent factors such as the severity of the disease and the like, the compound administered, and the like). For example, HCV infection in an individual can be detected and/or monitored by the presence of HCV RNA in blood, and/or having anti-HCV antibody in their serum. Other clinical signs and symptoms that can be useful in diagnosis and/or monitoring of therapy include assessment of liver function and assessment of liver fibrosis (e.g., which may accompany chronic viral infection).

Subjects for whom the therapy described herein can be administered include naïve individuals (e.g., individuals who are diagnosed with an infection, but who have not been previously treated) and individuals who have failed prior treatment ("treatment failure" patients). For HCV therapy, previous treatment includes, for example, treatment with IFN-α monotherapy (e.g., IFN-α and/or PEGylated IFN-α) or IFN-α combination therapy, where the combination therapy may include administration of IFN-α and an antiviral agent such as ribavirin. Treatment failure patients include non-responders (i.e., individuals in whom the HCV titer was not significantly or sufficiently reduced by a previous treatment for HCV to provide a clinically significant response, e.g., a previous IFN-α monotherapy, a previous IFN-α and ribavirin combination therapy, or a previous pegylated IFN-α and ribavirin combination therapy); and relapsers (i.e., individuals who were previously treated for HCV (e.g., who received a previous IFN-α monotherapy, a previous IFN-α and ribavirin combination therapy, or a previous pegylated IFN-α and ribavirin combination therapy), in whom the HCV titer decreased to provide a clinically significant response, but in whom the decreased HCV titer was not maintained due to a subsequent increase in HCV titer).

Other subjects for whom the therapy disclosed herein is of interest include subject who are "difficult to treat" subjects due to the nature of the HCV infection. "Difficult to treat" subjects are those who 1) have high-titer HCV infection, which is normally defined as an HCV titer of at least about $10^5$, at least about $5\times10^5$, or at least about $10^6$ or more genome copies of HCV per milliliter of serum, 2) are infected with HCV of a genotype that is recognized in the field as being associated with treatment failure (e.g. HCV genotype 1, subtypes thereof (e.g., 1a, 1 b, etc.), and quasispecies thereof or 3) both.

In other embodiment methods are provided for treating or reducing primary or metastatic cancer in a regimen comprising contacting a subject in need of treatment with a therapeutically effective amount or an effective dose of IFNλ synthekines or IFNλ variant polypeptides. Effective doses for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, hematologic cancers, melanomas, sarcomas, gliomas, particularly cancers of epithelial origin that express IFNλR1 and IFNAR1 or IFNAR2, or IL-10Rβ and IFNAR1 or IFNAR2. In some embodiments a cancer is assessed for responsiveness to an IFNλ synthekine by determining whether the cancer expresses the cognate receptors that the synthekine activates, e.g. determining the expression of IFNλR1, and IFNAR1 or IFNAR2. Tissues known to express IFNλR1 include, for example, lung, heart, liver (hepatocytes), prostate, keratinocytes and melanocytes. Cancers responsive to IFNλ and IFNλ synthekines may include, without limitation, melanoma, fibrosarcoma, hepatocellular carcinoma, bladder carcinoma, Burkitt's lymphoma, colorectal carcinoma, glioblastoma, non-small cell lung cancer, esophageal carcinoma, and osteosarcoma, among others.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Polynucleotides

The invention also provides isolated nucleic acids encoding the IFNλ synthekines or IFNλ variant polypeptides of the invention, vectors and host cells comprising the nucleic acid, and recombinant techniques for the production of the IFNλ synthekines or IFNλ variant polypeptides. Exemplary polynucleotides encode the protein sequences set forth herein, e.g. SEQ ID NO:7-19; 20, 22 and 23.

Nucleic acids of interest may be at least about 80% identical to a sequence that encodes SEQ ID NO:7-19, 20, 22 and 23, at least about 85%, at least about 90%, at least about 95%, at least about 99%, or identical. In some embodiments a contiguous nucleotide sequence is at least about 20 nt., at least about 25 nt, at least about 50 nt., at least about 75 nt, at least about 100 nt, and up to the complete coding sequence may be used.

For recombinant production of the IFNλ synthekines or IFNλ variant polypeptides, the nucleic acid encoding it is inserted into a replicable vector for further cloning (amplification of the DNA) or for expression. DNA encoding the IFNλ synthekines or IFNλ variant polypeptides is readily isolated and sequenced using conventional procedures. Many vectors are available. The vector components generally include, but are not limited to, one or more of the following: a signal sequence, an origin of replication, one or more marker genes, an enhancer element, a promoter, and a transcription termination sequence.

The IFNλ synthekines or IFNλ variant polypeptides of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, and the like. A heterologous signal sequence selected preferably may be one that is recognized and processed (i.e., cleaved by a signal peptidase) by the host cell. For prokaryotic host cells that do not recognize and process the native protein signal sequence, the signal sequence is substituted by a prokaryotic signal sequence selected. A heterologous polypeptide for this purpose may include therapeutic moieties, e.g. a polypeptide that provides a desired biological activity, such as induction of apoptosis, cell death, anti-viral activity, and the like.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2).

Host cells are transformed with the above-described expression or cloning vectors for interferon production and cultured in conventional nutrient media modified as appropriate for inducing promoters, selecting transformants, or amplifying the genes encoding the desired sequences.

The interferon composition prepared from the cells can be purified using, for example, hydroxylapatite chromatography, gel electrophoresis, dialysis, and affinity chromatography, with affinity chromatography being the preferred purification technique. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the interferon of interest and contaminants may be subjected to low pH hydrophobic interaction chromatography using an elution buffer at a pH between about 2.5-4.5, preferably performed at low salt concentrations (e.g., from about 0-0.25M salt).

The invention now being fully described, it will be apparent to one of ordinary skill in the art that various changes and modifications can be made without departing from the spirit or scope of the invention.

EXAMPLES

Example 1

Structure of the Lambda-IFN Receptor Ternary Complex Coupled with Cytokine Engineering Type III IFNs (also known as the IFN-λs) possess anti-viral and anti-proliferative activities restricted to tissues of endothelial origins and barrier surfaces. The crystal structure of a high-affinity human type III IFN ternary complex reveals the mechanism by which IL-10Rβ is a shared receptor for the IL-10 superfamily. Despite the lack of sequence homology between IL-10 cytokines, receptor-ligand recognition by IL-10Rβ is enabled through a network of three tyrosine residues that act as hydrophobic "anchor points" on all IL-10 cytokines. We affinity-matured both type I and III IFNs to explore the impact on signaling for the two cytokine families. A high-affinity IFN-λ significantly enhances the potency of signaling, target gene induction, anti-proliferative and anti-viral activities in Hepatitis B infected mice, whereas wild-type type I IFN anti-viral potencies are at a maximum, and not improved by affinity enhancement. Our results provide structural insights on the mechanism of binding of the shared IL-10Rβ to the IL-10 superfamily of cytokines, and highlight the relative plasticities of the anti-viral and anti-proliferative potencies of the type I and III IFN families.

Lambda Interferons (IFN-λ), also known as type III IFNs, are the most recently described family of interferon cytokines. Like type I IFNs, these secreted cytokines elicit an innate immune response to combat viral infections and also exhibit cytostatic (anti-proliferative) activities against cancer. Type III IFNs exhibit key differences from type I IFNs in both target specificity and potency, and are restricted in their expression to endothelial and barrier tissues. The IFN-λ family is conserved throughout vertebrate evolution to specifically and locally protect endothelial tissues at high risk of infection without inducing a systemic response that would otherwise be elicited by the type I IFNs. The localized action of IFN-λ is appealing for therapeutic applications, in that administration of IFN-λs may circumvent the known toxicity associated with type I IFNs such as IFN-α. Indeed, recent studies have highlighted the importance and non-overlapping role of type III IFNs in curing persistent norovirus infections, and IFN-λs have also demonstrated efficacy against a number of other viral pathogens including influenza, cytomegalovirus, Hepatitis C (HCV) and Hepatitis B (HBV). This promising anti-viral (AV) activity of IFN-λs has led to their evaluation in clinical trials for use in HCV, HBV, and Hepatitis D (HDV) (see for example, Clinical-Trials.gov identifier NCT02765802).

There are three sub-types of Type III IFNs in humans: IFN-λ 1-3 (also called IL-29, IL-28A, and IL-28B, respectively), all of which are members of the pleiotropic IL-10 superfamily. Type I and III IFNs recognize entirely different cell surface receptors. The 16 human sub-type I IFNs bind a heterodimeric receptor comprised of IFN-αR1 and IFN-αR2. The crystal structure of the type I ternary complex reveals a similar overall binding geometry formed by different IFN sub-types, with a network of conserved residues that act as "anchor points" and a network of non-conserved residues that impart sub-type specific affinities and functions. In this system, the interaction chemistries of the different IFN sub-types with the receptors results in distinct complex stabilities that manifest as both redundant and non-overlapping functions.

Lambda IFNs bind to a distinct heterodimeric receptor composed of IL-10Rβ and IFN-λR1. IL-10Rβ serves as a shared receptor for IL-10 superfamily members IL-10, IL-22 and IL-26, whereas IFN-λR1 is a type-specific receptor. Despite poor sequence conservation (<25% identity), the IL-10 superfamily cytokines are structurally conserved, and this structural similarity is believed to facilitate engagement of the shared IL-10Rβ. A crystal structure of the high-affinity binary IFN-λ1/IFN-λR1 complex revealed molecular contacts near the inter-domain "elbow" of IFN-λR1 important for initiation of signaling. Comparison of the IFN-λ1/IFN-λR1 binary complex to other IL-10 superfamily members indicated a similar ligand-receptor docking geometry between the IFN-λ binary complex and the IL-22/IL-22R1 and IL-10/IL-10R1 binary complex structures.

While the crystal structure of unliganded IL-10Rβ has been reported, it has not been possible to crystallize IL-10Rβ complexed with any of its cytokine ligands, or within a complete ternary signaling complex, presumably because of the extremely low affinity of these interactions. Biochemical data suggests that ternary complex formation is a sequential process. The first step in this assembly is the high-affinity interaction between IFN-λ1 and IFN-λR1, ($K_D$=73 nM). The IFN-λ1/IFN-λR1 complex then recruits IL-10Rβ to form the ternary complex, which brings Jak kinases constitutively associated with the receptor intracellular domains into close proximity to initiate signaling. The affinity of IL-10Rβ for the IFN-λ/IFN-λR1 binary complex has not been reported, but is estimated to fall between 12 and 234 µM based on SPR measurements to the IL-22/IL-22R1 and IL-10/IL-10R1 complexes, respectively. Mutagenesis studies combined with computational docking models have led to several proposed models of IL-10 superfamily ternary complexes, yet an experimentally determined structure has remained elusive.

While the type I and III interferon cytokines recognize distinct cell surface receptors, the intracellular domains of their respective receptors are associated with the same Janus Kinases, Jak1 and Tyk2, and signal through a common JAK/STAT pathway to induce Interferon stimulated genes and elicit similar immunoregulatory activities. However, the IFN-λs have been shown to induce these responses with lower potency and efficacy compared to type I IFNs. One rationale for a more potent type I response is that the ligand-receptor complexes exhibit higher affinity and greater stability compared to type III complexes. In principle, creating a more potent type III IFN could translate into improved activity in the clinic while leveraging the natural tissue specificity to maintain a lower toxicity profile compared to the type I IFNs.

Here we have engineered a higher affinity IFN-λ, which we used to crystallize the IFN-λA/IL-10Rβ/IFN-λR1 complex, and characterized enhanced functional potencies in vitro and in vivo. We also developed a high-throughput (HTP) functional screen to engineer type I IFNs with diverse activity profiles, for comparison to the affinity matured IFN-λ. This large panel of IFN variants was characterized for downstream STAT signaling, anti-viral (AV) activity, anti-proliferative (AP) activity, and receptor complex stability. Through these collective structure-function studies, we find type I IFN signaling and anti-viral activity is already at a maximum and affinity maturation offered diverse AP activities but little enhancement in AV potency. By contrast, type III IFN signaling and functional potency can be improved by affinity maturation. Further, the affinity enhanced type III IFN exhibited enhanced in vivo anti-viral activity against HBV.

Results

The numbering of amino acid substitutions in the examples and drawings is made relative to a truncated form of the interferon, which lacks 11 residues at the amino terminus. For clarity, the description and claims have substitutions numbered relative to SEQ ID NO:3, which represents the complete, mature protein. Thus there is an offset of 11 amino acids in the numbering.

Figure 7A:
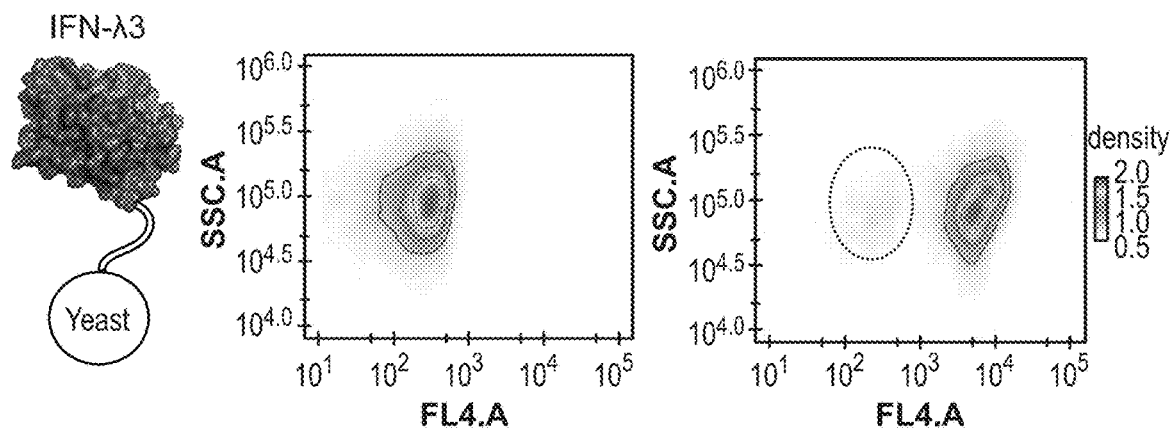
FIG. 7A-7E: Engineering a high-affinity lambda-Interferon.
Figure 7B:
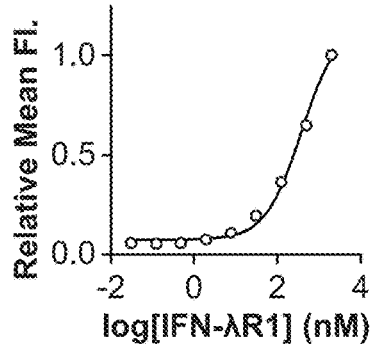

Engineering a high-affinity type III Interferon. We used yeast surface display as a platform for engineering a higher affinity IFN-λ. We focused our engineering efforts on IFN-λ3, because a crystal structure has been reported and it has the highest AV potency among the three natural lambdas. We targeted the interaction between IFN-λ3 and IL-10Rβ for affinity maturation since it is much lower affinity than IFN-λ3 binding to IFN-λR1. IFN-λ3 displayed on yeast bound to IFN-λR1 with a titration midpoint of approximately 400 nM (FIG. 7a, b). To the IFN-λ3 displayed on yeast, we tested for binding to IL-10 Rβ of both monomeric and an avidity-enhanced tetrameric form (in the absence of IFN-λR1), but did not observe binding (FIG. 1a, left panel). However, in the presence of IFN-λR1 tetramers, binding to IFN-λ3 displaying-yeast was observed when IL-10Rβ was presented as a tetramer (FIG. 1a, right panel), but not monomeric IL-10Rβ (FIG. 1a, middle panel). This data illustrates that IFN-λ3 is properly folded and displayed on yeast, and low affinity-cooperative interaction between IL-10Rβ and the composite interface of the IFN-λ/IFN-λR1 binary complex (FIG. 1a). Consequently, we carried out the affinity maturation experiments in the presence of soluble IFN-λR1 bound to IFN-λ3 on yeast.

Figure 7C:
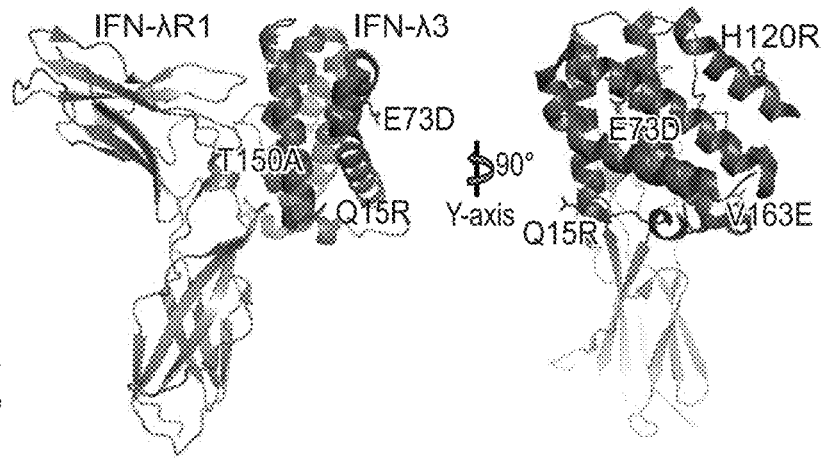
Figure 7D:
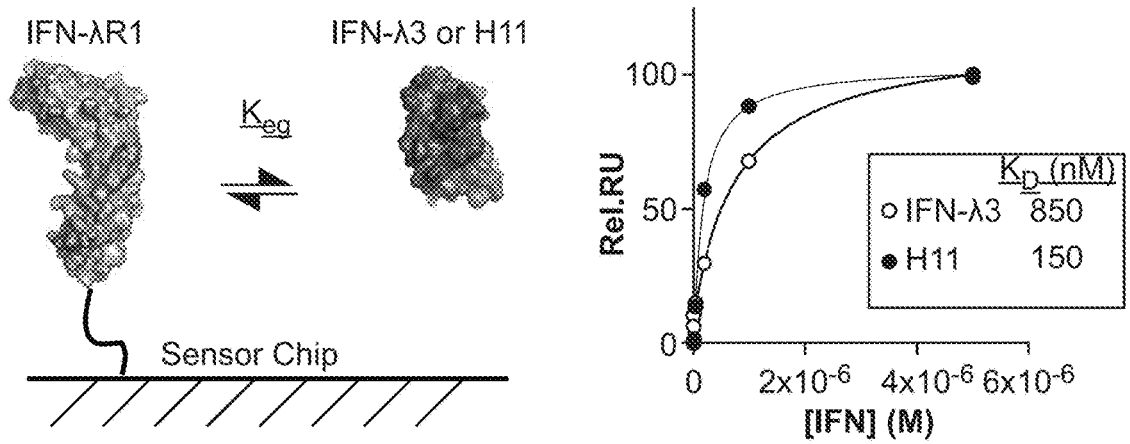

Since we lacked a structure to guide us on specific amino acids in IFN-λ3 that engage IL-10Rβ, our strategy involved error-prone PCR and gene shuffling, followed by selections on IL-10Rβ. Initially we created an error prone IFN-λ3 library containing $1 \times 10^8$ clones. Four rounds of selections were performed against increasingly stringent concentrations of IL-10Rβ (beginning with 400 nM IL-10Rβ tetramers and ending at 1 µM IL-10Rβ monomer). The enriched library showed some binding to 1 µM IL-10Rβ monomers (FIG. 1b, top two histograms). 96 clones were screened for 1 µM IL-10Rβ monomer binding and the affinities of interacting clones were measured by yeast-surface titrations with the IL-10Rβ receptor. The six highest affinity clones, (all of which had >1 µM affinities for IL-10Rβ), were then used as parental templates in a DNA shuffling reaction (FIG. 1c). The resulting second generation library contained $1 \times 10^8$ clones and was subjected to three rounds of selection against decreasing concentrations of IL-10Rβ monomer ranging from 1 µM to 125 nM. 96 clones were screened for binding to IL-10Rβ and followed up with yeast-surface titrations to measure affinity. The highest affinity clone, denoted "H11", was found to have an 'on-yeast' $K_D$ of 200 nM to IL-10Rβ (FIG. 1c). Sequence analysis of H11 revealed that the gene contained five mutations relative to the wild-type and was a combination of four first generation sequences from the DNA shuffling reaction (FIG. 1c, FIG. 7c). H11 was expressed recombinantly and the affinity of IL-10Rβ to the immobilized H11/IFN-λR1 binary complex was determined by surface plasmon resonance. The H11/IFN-λR1 complex showed a 30-fold increase in IL-10Rβ affinity ($K_D$=560 nM) compared to the wild-type IFN-λ3/IFN-λR1 binary complex (FIG. 1d). One of the H11 mutations, Thr150Ala, is located at the center of the IFN-λR1 binding site, which results in a ~five-fold higher affinity of H11 for IFN-λR1 (150 nM) relative to the wild-type IFN-λ3 affinity for IFN-λR1 (850 nM) (FIG. 1d).

Figure 2A:
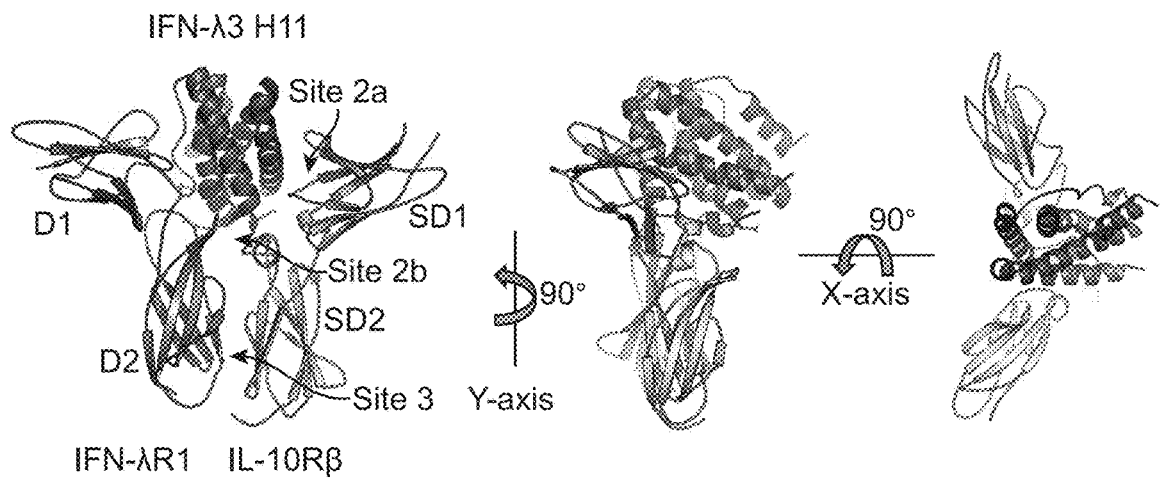
FIG. 2A-2B: Structure of the IFN-λ ternary complex.
Figure 7E:
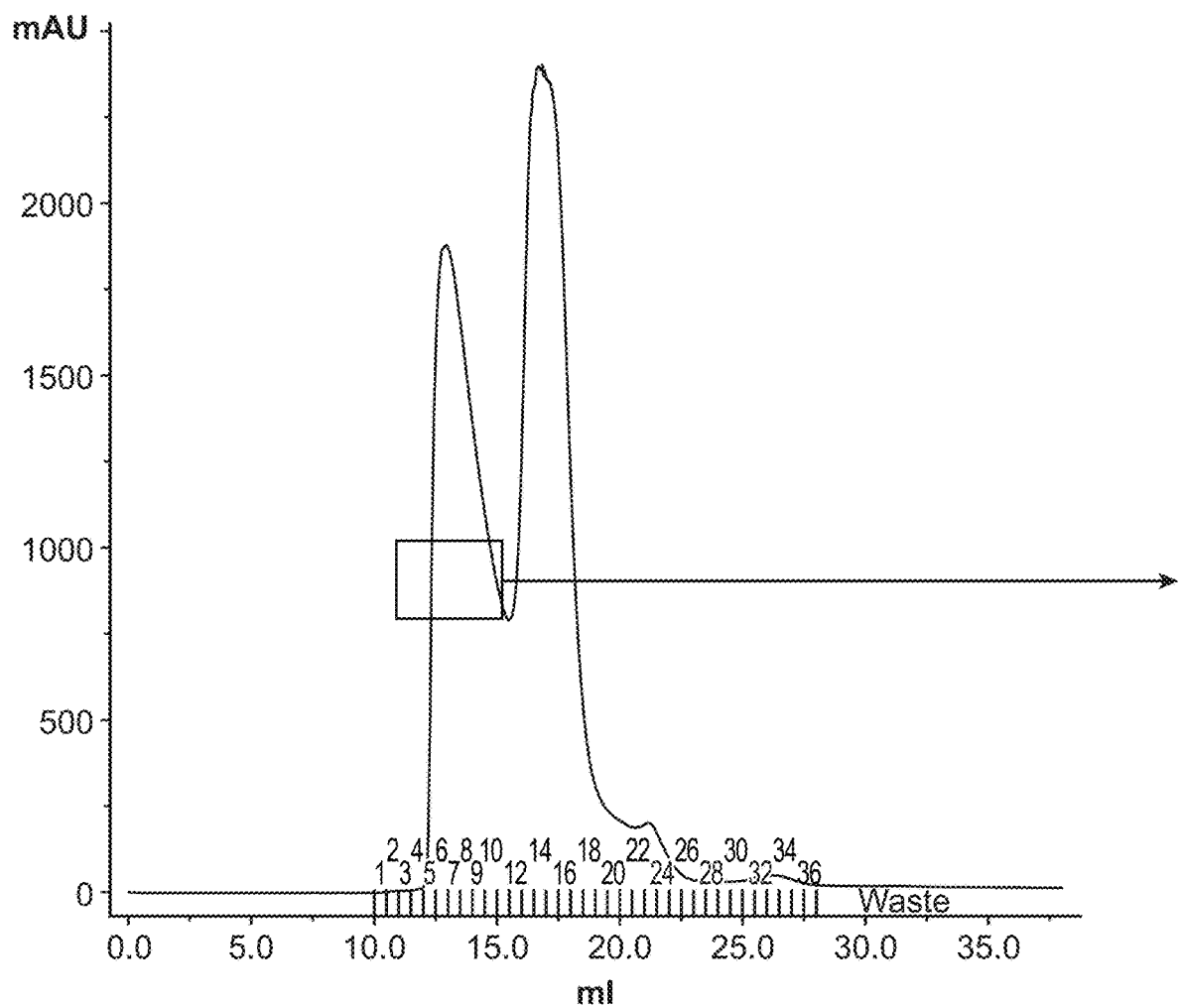
Figure 7E:
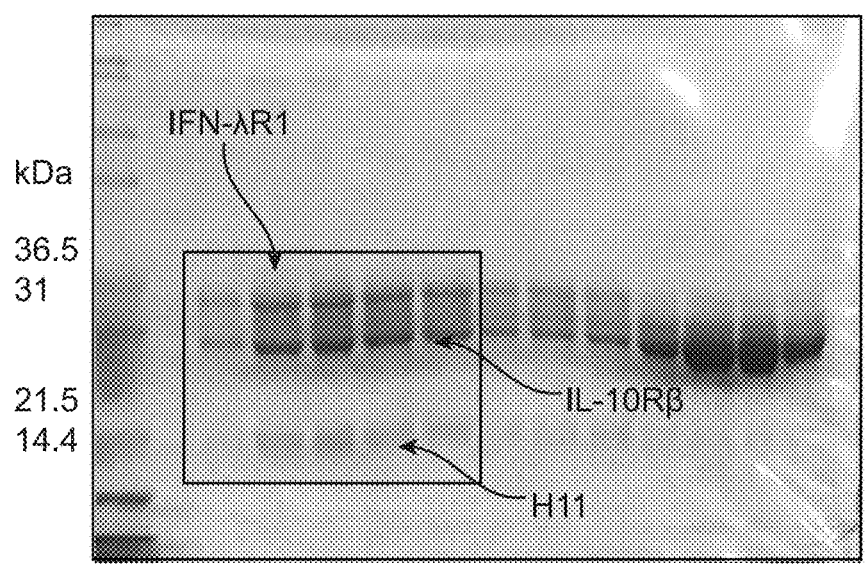
Figures 9A, 9B:
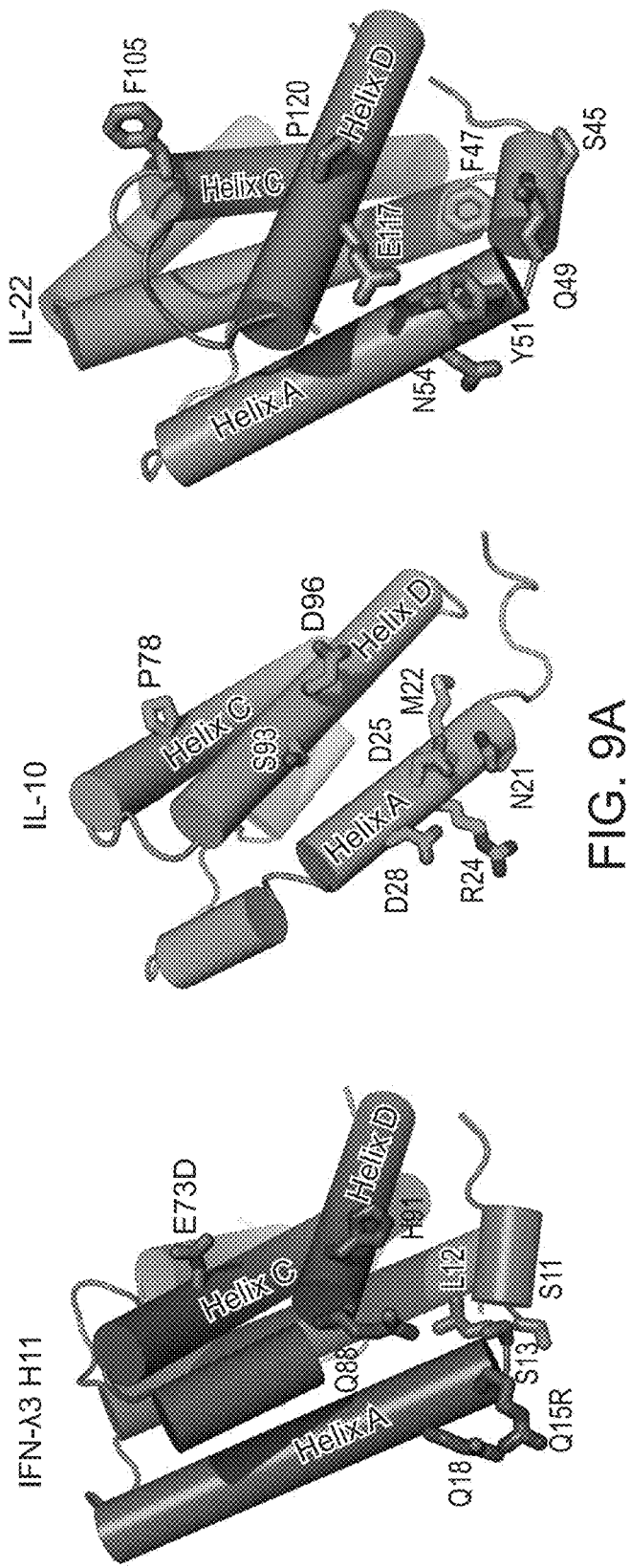
FIG. 9A-9B: Structural conservation of IL-10Rβ binding in the IL-10 superfamily.

Structure of the IFN-λ3 receptor ternary complex. The lack of a complete structure of a ternary complex of an IL-10 family cytokine is likely due to the low affinity of IL-10Rβ. Indeed, when we formed the ternary complex between wild-type IFN-λ3, IFN-λR1, and IL-10Rβ, we observed no chromatographic shift on gel filtration that would suggest a stable ternary complex. However, IFN-λ3 H11 was able to form a stable ternary complex with IFN-λR1 and IL-10Rβ (FIG. 7e). We crystallized the deglycosylated ternary complex, and obtained data to 2.85 Å (Table 1). The structure of the ternary complex was solved using molecular replacement with the binary structure of IFN-λ1/IFN-λR1, PDB 3O6G, and the unbound structure of IL-10Rβ, PDB 3LQM (FIG. 2a). No changes in domain orientations were observed from either the IFN-λ1/IFN-λR1 binary complex nor the apo IL-10Rβ structures. IL-10R3 makes extensive and contiguous contacts with the H11/IFN-λR1 binary complex, interacting with H11 through Sites 2a and 2b and with the IFN-λR1 stem at Site 3 (FIG. 2a, left panel). Interestingly, the shared IL-10Rβ receptor uniquely binds H11 at the end of the helical bundle, rather than more centrally on the face of the helical bundle, as is typical of cytokine/receptor binding interfaces (FIG. 2a, middle and right panel).

TABLE 1

| Data Collection | |
| --- | --- |
| Space group | P 31 2 1 |
| Resolution range | 46.24-2.847 (2.949-2.847) |
| Unique reflections | 20508 (2023) |
| Total reflections | 439939 (43828) |
| Completeness (%) | 1.00 (1.00) |
| Mean I/sigma(I) | 25.00 (1.16) |
| Multiplicity | 21.5 (21.7) |
| Unit cell | 106.795 106.795 129.71 90 90 120 |
| Refinement | |
| Reflections: used in refinement | 20498 (2015) |
| Reflections used for R-free | 1039 (97) |
| R-work | 0.1931 (0.3581) |
| R-free | 0.2484 (0.4600) |
| Number of non-hydrogen atoms | 4259 |
| solvent | 131.69 |
| macromolecules | 4187 |
| ligands | 61 |
| macromolecules | 135.61 |
| ligands | 195.77 |
| Protein residues | 537 |
| Average B-factor | 136.46 |
| Root-mean-square deviations | |
| RMS (bonds) | 0.002 |
| RMS (angles) | 0.59 |
| Wilson B-factor | 106.71 |
| Ramachandran | |
| Ramachandran favored (%) | 95 |
| Ramachandran allowed (%) | 4.2 |
| Ramachandran outliers (%) | 0.38 |
| Rotamer outliers (%) | 1.6 |

Figure 2B:
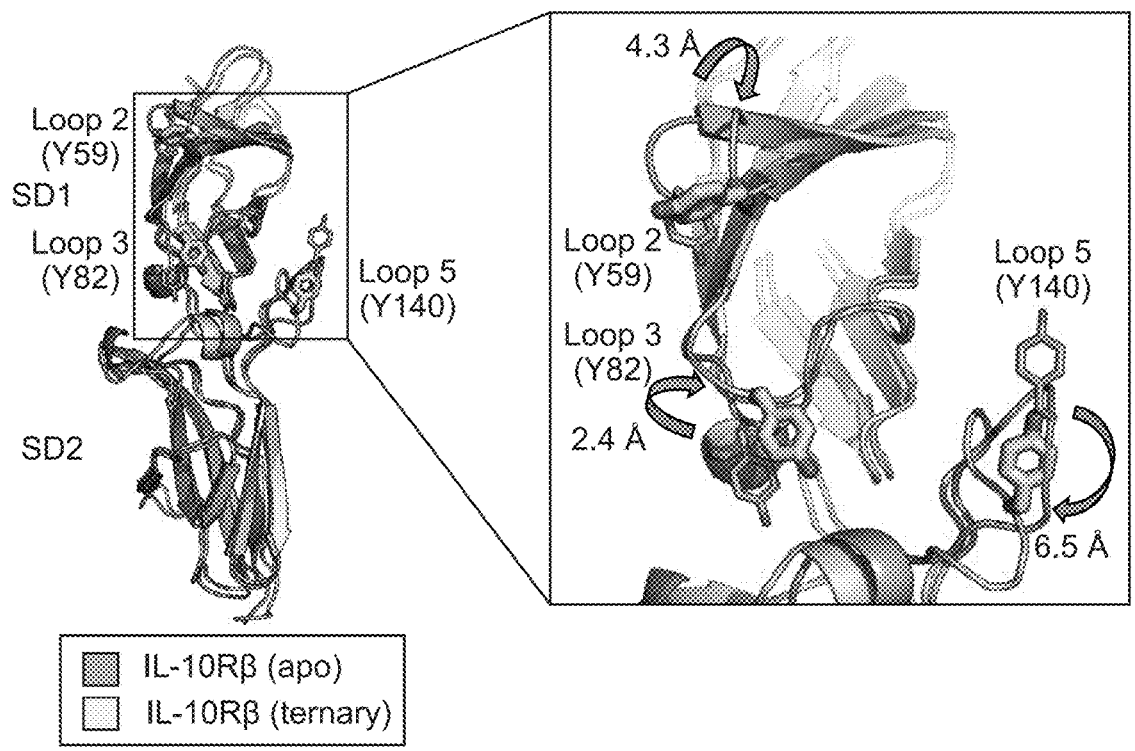

In the complex structure three IL-10Rβ loops, 2, 3 and 5, contain aromatic residues that undergo large conformational changes (2.4-6.5 Å) upon binding the IFN-λ/IFN-λR1 binary complex (FIG. 2). Notably, residues in loop 5 of IL-10Rβ are situated to share hydrogen bonds with both cytokine and receptor-receptor residues at sites 2b and 3. Tyr59 in loop 2 of IL-10Rβ binds IFN-λ3 H11 in a pocket formed by helices C and D of the cytokine (FIG. 2, 3a-c, Extended Data FIG. 2). In addition to a 4.3 Å displacement relative to the apo IL-10Rβ conformation, Tyr59 also rotates ~90° about two axes (FIG. 2b). Notably, the H11-specific mutation Glu73Asp (Helix C) forms a hydrogen bond with the hydroxyl group of Tyr59, stabilizing the interaction between the H11/IFN-λR1 binary complex and IL-10Rβ (FIG. 3c). Tyr82 on loop 3 of IL-10Rβ, also binds to IFN-λ3 H11 at site 2a and sits in the pocket formed between the N-terminus, and helices A and D of the cytokine (FIG. 2, 3a-c). In this position, Tyr82 shares two hydrogen bonds with the cytokine: One between the backbone carbonyl of Tyr82 and NE of His91 (H11) and a second between the hydroxyl group of Tyr82 and the nitrogen backbone of Ser13 (H11) (FIG. 3c).

At site 2b, Tyr140 and Trp143 of loop 5 (IL-10Rβ) bind IFN-λ3 H11 by "pinching" the N-terminus of Helix A (FIG. 3a-c). Both Tyr140 and Trp143 undergo large movements upon binding the IFN-λ3 H11/IFN-λR1 binary complex with the Cβ of the residues moving 6.5 Å and 3.6 Å, respectively, relative to the apo IL-10Rβ structure (FIG. 2b). In the ternary complex structure, Tyr140 (IL-10Rβ) forms two hydrogen bonds with H11 residues Gln18 and Gln15Arg, the latter of which is an engineered mutation of IFN-λ3 (FIG. 3c). Trp143 packs against the hydrophobic backbone of Helix A and contributes van der Waals interactions as well as a hydrogen bond shared with the backbone carbonyl of the N-terminal residue Ser1 (H11) (FIG. 3c).

Site 3 represents the shared interface between the receptor stem domains D2 of IFN-λR1 and SD2 of IL-10Rβ. The site 3 interface extends from site 2b to the C-termini of the membrane-proximal receptor domains (FIG. 2a, 3a, b, and d). This contact region is larger in surface area (1900 Å$^2$) than either of the cytokine-receptor interfaces (1700 Å$^2$ each) (FIG. 3b). Site 3 is composed of van der Waals interactions along the length of the interface, but hydrogen bonds also play an important role in stabilizing the complex. Hydrogen bonds are observed between the side chain of Arg130 (IL-10Rβ) to the backbone carbonyl Gln163 (IFN-λR1), and side chain to side chain hydrogen bonds between His128 (IL-10Rβ) and Gln163 (IFN-λR1), Glu141 (IL-10Rβ) and Tyr189 (IFN-λR1), and Thr142 (IL-10Rβ) and Thr183 (IFN-λR1) (FIG. 3d). The structure highlights the importance of receptor stem-stem contacts in the cooperative binding of IL-10Rβ to the IFN-λ3 H11/IFN-λR1 binary complex.

Implications for a shared IL-10Rβ binding mode to IL-10 family of cytokines. Our structure of the IFN-λ ternary complex provides insight into the interactions of IL-10Rβ with other members of the IL-10 superfamily. Using the IFN-λ ternary complex as a structural template, we docked IL-10Rβ onto the binary structures of IL-22/IL-22R1 (pdb 3DLQ) and IL-10/IL-10R1 (1J7V) in order to elucidate the molecular basis of IL-10Rβ binding and recognition (FIG. 4a, left). Based on our structure of the IFN-λ3 H11/IFN-λR1/IL-10Rβ ternary complex, IL-10Rβ makes contacts with three cytokine helices: A, C, and D. Structure-function studies have identified mutations believed to be important for multiple IL-10 family members binding to the shared IL-10Rβ receptor. All of these mutations fall within the IFN-λ3 H11 binding region of the receptor and contact hotspot Tyr residues of IL-10Rβ (FIG. 4a, right, red surface). Structure-based sequence alignment of the three cytokines indicates that residues mapping to the IL-10Rβ binding site are highly divergent (FIG. 4b). Despite this lack of conservation, structural comparison of the IFN-λ3, IL-10, and IL-22 residue within the site 2 interface reveals that the three cytokines have a conserved pattern of hydrophobic patches at the sites of the IL-10R3 tyrosine docking (FIG. 4c), which are surrounded by polar residues. Thus, IL-10 family members appear to have evolved chemical complementarity with IL-10Rβ, but through distinct pairwise interactions.

Figure 5A:
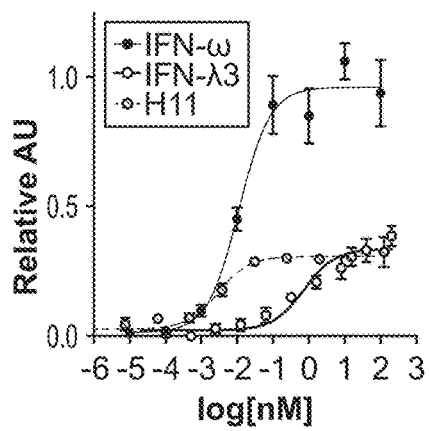
FIG. 5A-5G: Functional characterization of an engineered IFN-λ3 variant. IFN-λ3 H11 (orange) was compared to the wild-type IFN-λ3 (black) and the type I, IFN-ω (red), in several functional assays.
Figure 5B:
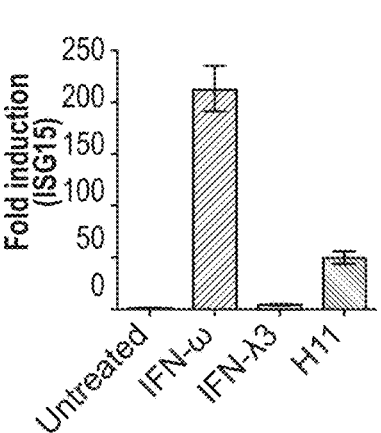
Figure 5C:
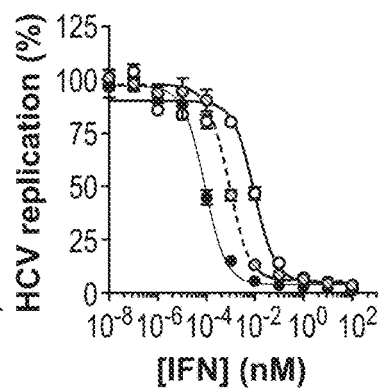
Figure 10A:
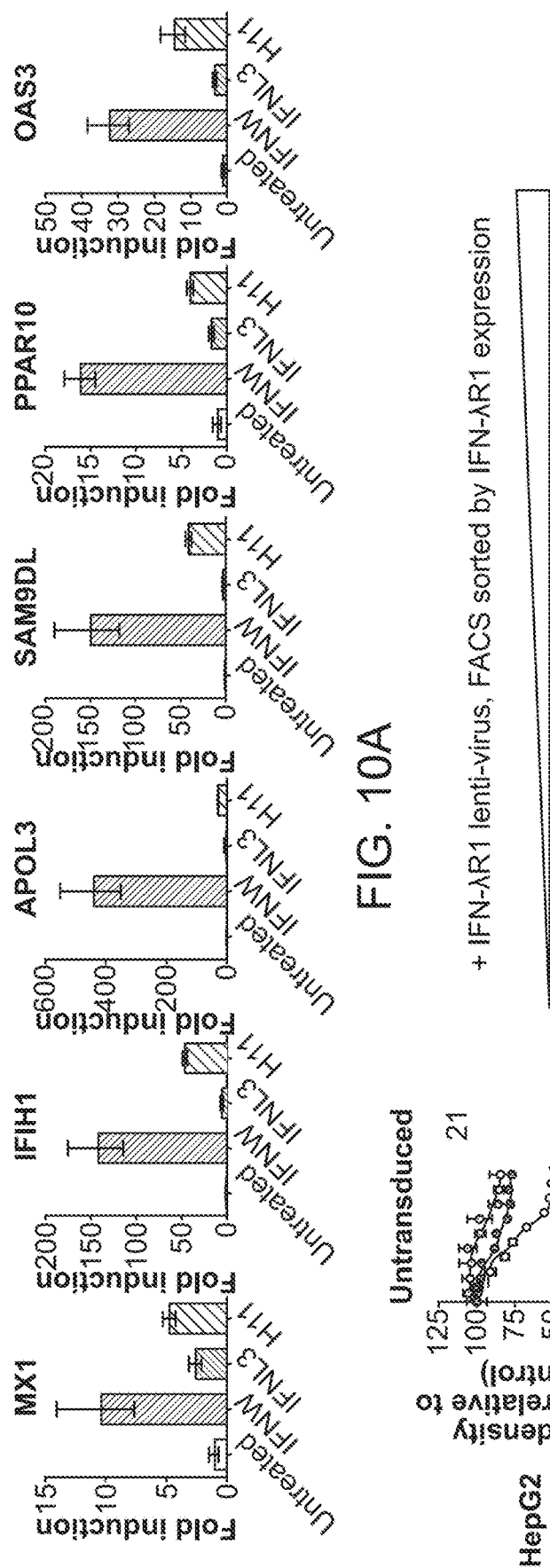

Functional behavior of high affinity IFN-λ. To determine if stabilization of the IFN-λ ternary complex could enhance type III IFN signaling and function, we measured in vitro phospho-STAT1 signaling, ISG gene induction, and antiviral and anti-proliferative activities of H11 relative to the wild-type type III IFN (IFN-λ3) and a type I IFN (IFN-ω). H11 improved the $EC_{50}$ for phospho-Stat1 on type I and III IFN-responsive Hap1 cells by 100-fold relative to the wild-type IFN-λ3, matching the potency of IFN-ω. Despite this improvement in $EC_{50}$, however, the $E_{max}$ values for both IFN-λ3 and H11 were only 30% that of IFN-ω (FIG. 5a). Similarly, H11 induced ISGs more potently than wild-type IFN-λ3 in Hap1 cells, although gene induction remained well below levels induced by the type I IFN (FIG. 5b, FIG. 10a). H11 improved AV activity, with potency 12-fold higher than wild-type IFN-λ3, though ten-fold less potent than the type I IFN on Huh7.5 cells infected with HCV (FIG. 5c).

Figure 5D:
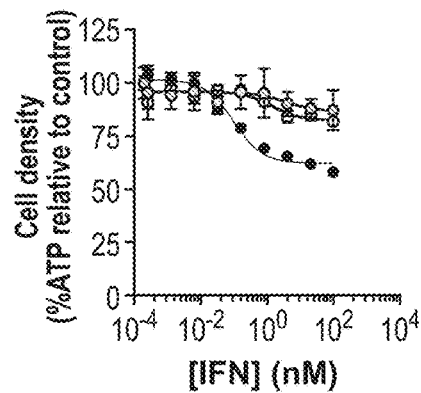
Figure 5E:
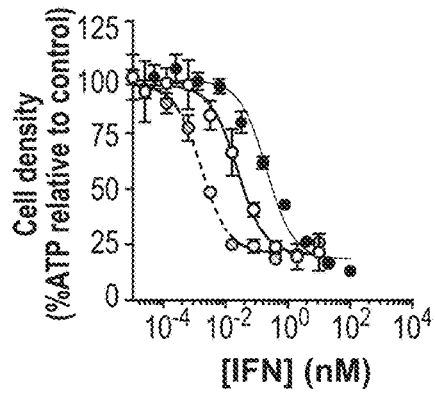
Figure 10B:
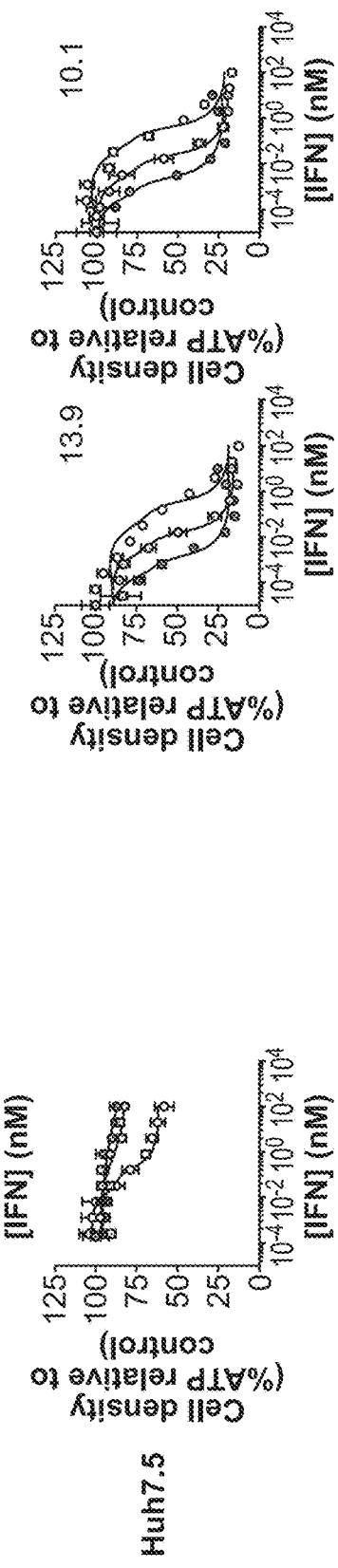

Both IFN-λ3 and the engineered high-affinity H11 mutant elicited minimal AP activity (FIG. 5d) which has been previously observed in vitro. We hypothesized that the lack of AP activity could be due to the limited expression of IFN-λR1 on Huh7.5 cells. Indeed, when IFN-λR1 was transduced into Huh7.5 or WISH cells, a lambda IFN non-responsive cell line, type III IFNs robustly induced an AP effect, even exceeding the potency of type I IFN. As anticipated, the effect of the high-affinity H11 was stronger than that of the wild-type IFN-λ3 and the magnitude of this difference depended on relative levels of IFN-λR1 expression levels (FIG. 10b). Taken together, these experiments suggest type III IFN AP activity may be limited by both IFN-λR1 receptor expression and stability of the lambda-IFN signaling complex; the latter which can be addressed through affinity maturation (FIG. 5d, e, FIG. 10).

Figure 5F:
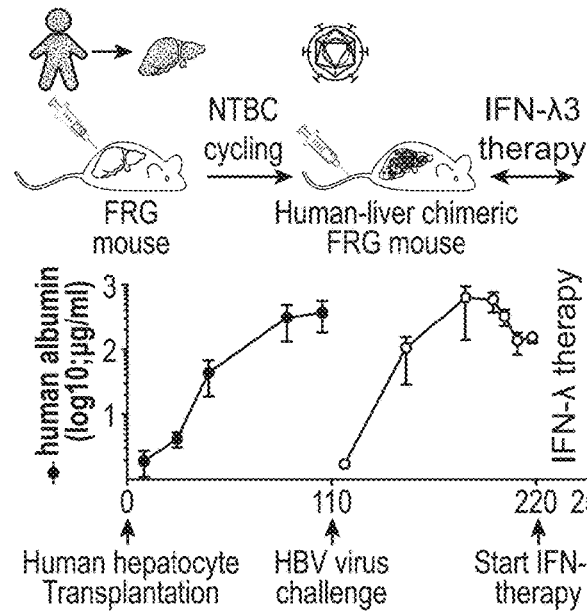
Figure 5G:
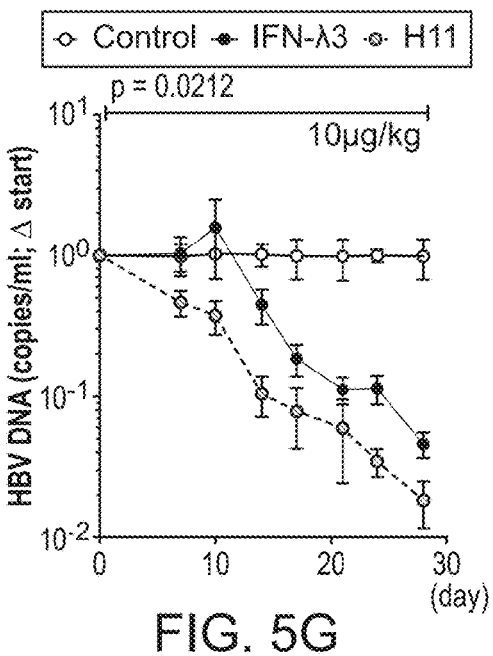

To test whether the improved in vitro potency of H11 over wild-type IFN-λ3 results in enhanced in vivo anti-viral therapy, we tested our engineered interferon in human liver chimeric mouse models of Hepatitis B virus (HBV) and Hepatitis D virus (HDV). We made use of the liver chimeric models developed by Grompe and colleagues, in which mice are fumarylacetoacetate hydrolase deficient (fah$^{-/-}$) and liver injury is controlled by administration of 2-(2-nitro-4-trifluoro-methyl-benzoyl)-1, 3 cyclohexanedione (NTBC) and Xu et al, in which NOG mice express a thymidine kinase transgene in their livers allowing liver injury to be controlled by simple ganciclovir administration (REF). After transplantation of human fetal hepatoblasts into FRG mice, we induced mouse liver damage by intermittent withdrawal of the protective drug NTBC. Alternatively, mouse liver injury was induced by ganciclovir administration to TK-NOG mice followed by transplantation with primary human adult hepatocytes. In both cases, engraftment levels over time were monitored by measuring human albumin (hAlb) levels in the sera (FIG. 5f)[31]. Mice were challenged with HBV upon plateauing hAlb levels and chronically infected mice were then subjected to IFN-λ3-based anti-viral treatment. IFN-λ3 H11 suppressed HBV viral load more effectively than the IFN-λ3 wild-type regimen (FIG. 5g). HBV surface antigen (sAg) levels also decreased more profoundly in response to H11 compared to wild-type treatment, although both the response amplitude and inter-group differential were smaller than those observed for viral loads (FIG. 10c). Human albumin levels, which serve as a proxy for toxicity, remained stable during the course of treatment, excluding the possibility of human hepatocyte loss and suggesting the higher-affinity IFN-λ was no more toxic than the wild-type. (FIG. 10d). Similarly, TK-NOG mice with humanized livers were first inoculated with HBV, followed by superinfection with HDV. Mice were then treated with wild type or H11 IFN-λ3. A significant anti-HDV effect was observed, which was more profound in the H11 compared to wild-type treated mice. Thus H11 demonstrates improved therapeutic efficacy without obvious toxicity, and suggests that affinity improvements, now using the crystal structure of the ternary complex as a guide, can generate a therapeutically improved IFN-λ for both anti-viral and anti-cancer therapy.

Figures 6A, 6B, 6C, 6D:
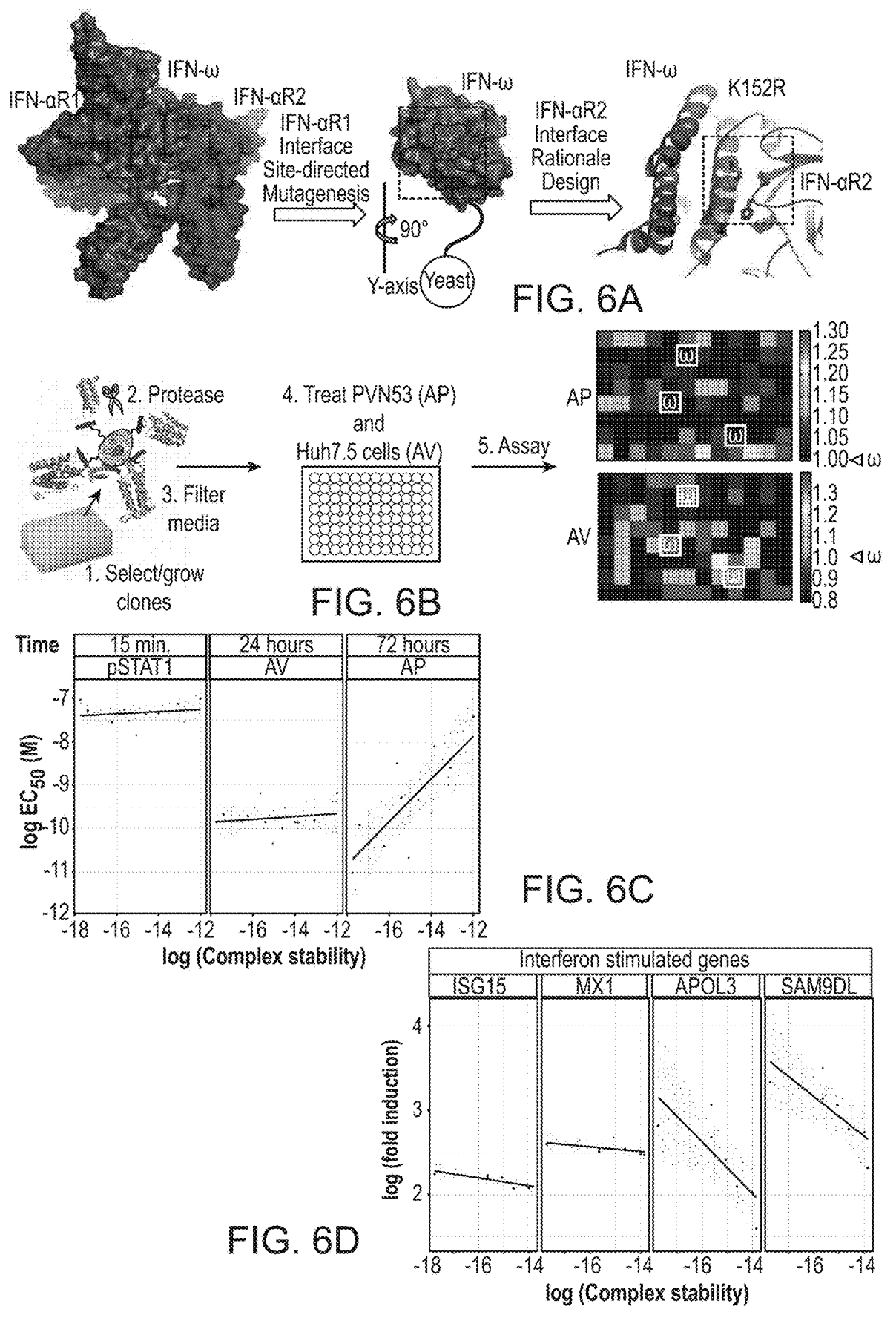

Probing type I Interferon function through structure-guided protein engineering. Having shown that affinity enhancement improved the AV and AP potency of the Type III IFN IFN-λ3, we wished to probe the sensitivity of Type I IFN AV and AP functions to receptor affinity using a combinatorial engineering approach as we used for IFN-λ3. Rather than take an error-prone approach, we were guided by the structure of the type I interferon, IFN-w, in complex with the IFN-αR1 and IFN-αR2 receptors (FIG. 6a). We generated a site-directed mutagenic library of IFN-ω that diversified its IFN-αR1 binding interface, the lower-affinity site, as a means of creating variants with modified anti-viral and anti-proliferative activities (FIG. 6a). We enriched the library for binders to wild-type IFN-αR1 affinity ($K_D$=1 µM). In order to find the most interesting variants (diverse activities), we developed a high-throughput functional screen, and characterized 288 randomly selected clones from the library (FIG. 6b). For our screen, distinct type I IFN variants were cleaved from yeast cells, and the released cytokines in the supernatant were purified away from the yeast by filtration. The IFN-containing supernatant was then used to treat cells (FIG. 6b). Based on their diverse anti-proliferative and anti-viral activities, four IFN-ω variants were selected for recombinant expression and characterization. Previously, we rationally designed an IFN-w variant (Lys152Arg), with 100-fold higher affinity for the IFN-αR2 receptor than the wild-type cytokine. We thus added the Lys152Arg mutation on to each of our engineered IFN-αR1 interface variants from the HTP screen. In addition to these mutants, we biophysically and biochemically characterized the wild-type IFN-ω, IFN-ω (Lys152Arg), and a shuffled IFNα mutant (Maxygen 9×25) that was previously reported to be biased towards AV activity.

We measured signaling potency (phospho-STAT1), gene induction, and anti-viral and anti-proliferative activities of our panel of engineered interferons relative to wild-type IFN-ω (FIG. 6c). We also determined the affinity of each cytokine for the IFN-αR1 and IFN-αR2 subunits via surface plasmon resonance (Table 2). Although receptor affinity was not used as a criterion for selection of the variants, we aimed to interrogate the correlation between complex stability (the product of the cytokine $K_D$s for binding each receptor subunit) and cytokine activity. Affinities for IFN-αR1 ranged from 20 nM to 300 µM (wild-type IFN-ω $K_D$=1.2 µM). Affinities for IFN-αR2 were between 2 nM for the unmodified IFN-ω and 200 µM in the Lys152Arg background. In all, our IFN variants constitute a 5.7-log range of complex stabilities (Table 2). The $EC_{50}$s of our variants for STAT signaling and anti-viral activity were found to be insensitive to changes in affinity, as illustrated by both minimal improvement over the wild-type EC50s and narrow range of EC50s (0.85 and 1.2 logs, respectively) for the broad range of complex stabilities (FIG. 6c, left and middle panels, Table 2). In contrast, anti-proliferative activity varied by 3.5 logs and correlated (R=0.67) with complex stability (FIG. 6c, right). We measured induction of a representative set of Interferon stimulated genes (ISGs) by seven of our IFN variants on Huh7.5 cells (FIG. 6d). As observed with the differential effects of complex stability on AV and AP activities, high-affinity variants offered little improvements in gene induction (such as ISG15 and MX1) over the wild-type (FIG. 6d, two left panels) while other genes (like APOL3 and SAM9DL) were more sensitive to complex stability (FIG. 6d, two right panels). This observation is in accord with several previous studies.

TABLE 2

| IFN | EC50 pSTAT1 (M) | EC50 AV (M) | EC50 AP (M) | KD IPNAR1 (M) | KD IFNAR2 (M) | log(KDR1* KDR2) | Fold gene induction over control ISG15 |
|---|---|---|---|---|---|---|---|
| 9X25 | 9.2E−08 | 1.4E−10 | 9.6E−12 | 6.0E−09 | 3.0E−10 | −17.74 | |
| P6B6 K152R | 5.2E−08 | 2.1E−10 | 1.2E−10 | 2.0E−08 | 2.0E−10 | −17.40 | 165 |
| P6F4 K152R | 2.8E−08 | 1.9E−10 | 3.9E−11 | 2.9E−08 | 2.0E−09 | −16.24 | |
| P6B6 | 5.4E−08 | 6.5E−10 | 3.2E−09 | 2.3E−08 | 1.0E−08 | −15.64 | 170 |
| P6P4 | 3.0E−08 | 1.4E−10 | 5.2E−10 | 4.8E−08 | 8.0E−09 | −15.42 | |
| IFNW K152R | 1.4E−08 | 4.5E−11 | 2.2E−11 | 4.3E−06 | 2.0E−10 | −15.07 | 160 |
| IFNW | 4.2E−08 | 1.0E−10 | 4.6E−10 | 1.2E−06 | 2.0E−09 | −14.62 | 120 |
| P6D2 K152R | 4.5E−08 | 1.4E−10 | 2.3E−10 | 5.0E−05 | 2.0E−10 | −14.00 | 121 |
| P6D2 | 4.8E−08 | 1.4E−10 | 7.8E−09 | 7.0E−06 | 2.0E−09 | −13.85 | 125 |
| F5C9 K152R | 7.5E−08 | 1.5E−10 | 2.5E−09 | 4.1E−04 | 2.0E−10 | −13.08 | |
| P5C9 | 9.6E−08 | 6.6E−10 | 3.8E−08 | 3.2E−04 | 3.0E−09 | −12.01 | |
| log(Range) | 0.8 | 1.2 | 3.6 | 4.8 | 1.7 | 5.7 | 0.2 |

| IFN | Fold gene induction over control | | | | | | | | | | |
|---|---|---|---|---|---|---|---|---|---|---|---|
| | MX1 | IFIH1 | TNFSF10 | CXCL10 | SAM9DL | APOL3 | PPAR10 | IFI6 | IL15RA | OAS3 | USP18 |
| 9X25 | | 382 | 8 | 28 | 2150 | 664 | 73 | 1721 | 37 | 290 | 24 |
| P6B6 K152R | 354 | 279 | 13 | 48 | 3177 | 1166 | 85 | 1431 | 40 | 214 | 24 |
| P6F4 K152R | | | | | | | | | | | |
| P6B6 | 326 | 361 | 7 | 23 | 1384 | 481 | 60 | 939 | 58 | 235 | 25 |
| P6P4 | | | | | | | | | | | |
| IFNW K152R | 475 | 290 | 6 | 17 | 1152 | 262 | 75 | 1863 | 62 | 292 | 21 |
| IFNW | 347 | 251 | 4 | 9 | 601 | 126 | 46 | 900 | 56 | 255 | 17 |
| P6D2 K152R | 299 | 221 | 3 | 8 | 553 | 106 | 39 | 953 | 31 | 247 | 14 |
| P6D2 | 302 | 200 | 2 | 4 | 209 | 39 | 33 | 834 | 123 | 242 | 13 |
| F5C9 K152R | | | | | | | | | | | |
| P5C9 | | | | | | | | | | | |
| log(Range) | 0.2 | 0.3 | 0.8 | 1.1 | 1.2 | 1.5 | 0.4 | 0.3 | 0.6 | 0.1 | 0.3 |

DISCUSSION

In this study, we implemented a protein engineering strategy to gain structural access to the lambda-IFN/IFN-λR/IL-10Rβ ternary complex, and to assess the relative potential for enhancing the functional efficacies of type III versus type I IFNs. The ternary complex illuminates several important molecular features governing the IL-10Rβ interactions of IL-10 family cytokines, which are of extremely low affinity and thus presents a barrier to their effective therapeutic use. Previously, the divergent sequences within the IL-10 superfamily cytokines placed substantial limitations on our ability to engineer more potent IL-10 family therapeutics. With the structure in hand, we observe how IL-10 superfamily cytokines present three hydrophobic patches on their surface that interlock with aromatic residues on interdomain loops of IL-10Rβ. Additionally, the structure reveals the importance of extensive IFN-λR1/IL-10Rβ stem-stem interactions in stabilizing the ternary complex, providing a molecular rationale for the role of cooperativity in the formation of IL-10 family cytokine complexes.

A hint that type III IFN AV activity could be improved was gleaned from studies establishing an intrinsic 60-fold difference in AV $EC_{50}$s between IFN-λ2 and 3. We anticipated that this effect could be further exaggerated through molecular engineering approaches given that type III IFNs bind IL-10Rβ with nearly undetectable affinities in vitro. Using directed evolution, we were able to identify variants with up to 150-fold increased complex stability, which resulted in a 100-fold improvement in the $EC_{50}$ for pSTAT1 signaling and 12-fold improvement in the $EC_{50}$ for AV activity. Studies of Hepatitis B Virus-infected human liver chimeric mice validated this improved potency in an in vivo setting by demonstrating that an engineered IFN-λ can improve upon the efficacy of the wild-type cytokine to be more type I-like; a quality recent clinical trials have exposed as being clinically desirable. A more potent IFN-λ which maintains a low toxicity profile compared to type I IFNs provides new avenues for treatment of persistent viral infections such as Hepatitis B, -C, and -B and -D co-infections, and as a broad spectrum antiviral.

In vitro, lambdas have a blunted AP activity which effects could be rescued by over-expression of the IFN-λR1 receptor. Indeed, the engineered lambda was more potent than the wild-type. While the minimal AP effects on untransduced cell lines may appear to suggest type III IFNs may have limited potential as anti-cancer agents, in vivo studies paint a different picture. Murine cancer models have demonstrated IFN-λs can significantly inhibit tumor growth while having a marked reduction in toxicity relative to type I IFN treatment. Taken together this gives hope for continued cancer related efforts.

We also developed a panel of type I IFN proteins with a range of affinities to probe the molecular mechanism underlying the observed differences in anti-viral and anti-proliferative potencies of type I versus type III IFNs. In vitro AV studies have established the type III IFNs to be less potent than the type I IFNs, which translates into a lower efficacy in the clinic, as observed in recent HCV, HBV clinical trials. Previous structure-function studies of the type I IFNs have demonstrated a modest 2-fold difference in AV potency between the highest affinity natural IFN (IFN-β) or engineered IFN such as IFN-α2 YNS relative to lower affinity ligands such as IFN-α2. However, one study reported engineering type I IFNs with >20-fold improved AV activities but relatively unchanged AP activities. This study measured AP activity using the Daudi cell line, which is more sensitive to AP effects, possibly leading aberrant AP:AV ratios. Here, using structure-based engineering, we demonstrate that STAT signaling potency, and AV activity are insensitive to complex stability and stable relative to wild-type levels. By contrast, AP activity is directly correlated with complex stability. This observation held for the synthetic IFN, 9×25, engineered from DNA shuffling which was previously reported to have a 20-fold improvement in AV activity over a wild-type IFN. In this study, the AV activity of the shuffled IFN ($EC_{50}$=140 pM) was similar to IFN-ω ($EC_{50}$=100 pM) and has a 48-fold improvement in the AP activity over the wild-type consistent with a 3-log improvement in complex stability. Collectively, these experiments demonstrate that type I IFNs vary in their AV:AP profiles mainly due to differences in AP potencies between ligands as a result of varied receptor affinities.

We were able to engineer a type III IFN with improved signaling and AV activities. The type III IFN ternary complex may further guide efforts to engineer even more potent cytokines which can close the gap in efficacy between the type I IFNs and type III IFNs.

Materials and Methods

Yeast display of IFN-ω and IFN-λ3. For both type I and III IFNs, the cytokines were displayed on yeast as previously described but containing a 3C rhinovirus protease tag at the N-terminus. Staining and selection was performed via streptavidin-phycoerythrin labeled receptors with separation of the receptor-yeast population by paramagnetic anti-phycoerythrin microbeads (Miltenyi; MACS). Expression on the yeast-surface was assayed by staining with the Myc-tag antibody conjugated to Alexa 647 (Cell Signaling). Progression of the enrichment was monitored by the receptor yeast staining by flow-cytometry (BD Accuri). A site-directed library was used for engineering type I IFNs. A round of error-prone PCR and DNA shuffling was used for the second-generation of Lambda variants.

Functional screen for IFN-ω. Individual clones from the library was plated on SD-CM plates, grown in a 96-deep well format. The protein for each clone was cleaved from the yeast using 3C protease, separated from the yeast by filtration (Whatman Unifilter 800), and assayed for anti-viral activity by tracking HCV viral replication in Huh7.5 cells and anti-proliferative activity in PVN53 treated cells by measuring cell density as previously described. Variants with diverse activities were selected for recombinant expression and characterization.

Protein expression, purification, and structural determination. Type I IFN cytokines, type I IFN receptors, type III IFNs, and type III receptors were expressed in the Hi5 insect expression system, purified as previously described and stored in 10% glycerol. For crystallography, all four glycosylation sites in IL-10Rβ were mutated from Asn to Gln as described in Yoon et. al. IFN-λR1 was expressed in HEK293 Gnti⁻ cells and de-glycosylated by treatment with EndoF and EndoH. The methylated "H11"/IFN-λR1/IL-10Rβ complex was purified by SEC on a S75 column (GE). Crystals were obtained within 24 hours at 20° C. from the MCSG3 screen (Anatrace) and optimized to 0.2 M Ca acetate, 0.1 M Imidazole pH 8.0, 10% PEG8000, and 3% sucrose as an additive (Catalog #HR2-138, Hampton). Cryoprotectant was the mother liquor plus 8% each of sucrose, glucose, and xylitol.

Crystallographic data were collected at the Advanced Light Source (ALS) Beamline 8.2.1. Data were indexed, integrated and scaled using XDS or HKL2000 program suites. Crystal structures were solved by molecular replacement with the program PHASER using the IFN-λ1/IFN-λR1 binary complex (PDB ID: 3OG6) and apo IL-10Rβ (PDB ID: 3LQM) structures as search models. The final structure was built by iterative cycles of reciprocal space refinement with PHENIX and BUSTER and manual rebuilding with COOT. Crystallographic software used in this project was installed and configured by SBGrid.

Sequence, structural, and FACS analysis. Promals3D was used to perform a structure based sequence alignment. Sequence alignments and percent identity calculations were performed with JalView (the University of Dundee). Structural alignments, homology models, surface area and distance calculations, and figures were generated in Pymol (Schrödinger, LLC). Figures of FACS data with either R with the Bioconductor source (R-project) or Prism (GraphPad Software, Inc).

Surface plasmon resonance. GE Biacore T100 was used to measure the $K_D$ by either kinetic (type I IFNs) or equilibrium (type III IFNs) methods. Approximately 100 RU of each of the receptors of were captured on a Biotin CAP-chip (GE) including a reference channel of an unrelated cytokine receptor (IL-2Rβ).

In vitro characterization. For type I IFNs, signaling, anti-viral and anti-proliferative assays were performed as previously described. For measuring gene induction, Huh7.5 cells were plated in a 6-well format and treated with 1 nM type I IFNs for 24 hours, Hap1 cells (a gift from Jan Carette) were treated with 5 pM type I or III IFNs for 6 hours, RNA was extracted with the RNeasy Micro kit (Qiagen) which was converted to cDNA by a RT-PCR reaction (HC RNA-to-cDNA kit, Thermo Fisher Scientific), and ISG induction relative to the untreated controls and normalized to 18S levels were measured by the Taqman qPCR assay system on a StepOnePlus instrument (Thermo Fisher Scientific) following manufacture instructions. For type III IFNs, pSTAT1 signaling was performed as previously described except Hap1 cells were detached after IFN treatment by incubating with trypsin (Gibco) for 5 min before fixing and staining as previously described.

Anti-proliferative activity of type III IFNs. Lentiviral pseudoparticles were generated by co-transfecting $4\times10^5$ Lenti-X 293T cells (Clontech) in poly-L-lysine coated 6-well plates with plasmids expressing the pLX304 proviral DNA encoding human IFN-λR1, HIV-1 gag-pol, and VSV-G at a ratio of 1.1/0.7/0.2, respectively. For each transfection, 5 µl Lipofectamine 2000 (Thermo Fisher Scientific) was combined with 2.0 µg total DNA in 100 µl Opti-MEM (Gibco). Transfections were carried out for 6 h, followed by a medium change to DMEM containing 3% FBS. Supernatants were collected at 24 h and 48 h, pooled, passed through a 0.45 µm filter and stored at −80° C. $3\times10^5$ Huh7.5 and WISH cells were resuspended in DMEM containing 10% FBS, 500 µl lentivirus, and 8 µg/ml polybrene in a total volume of 1.5 ml and spinocualted in 12-well plates for 1.5 h at 850×g. 48 h post transduction the cells were selected with 2.5 µg/ml blasticidin. Huh7.5 and WISH cells were harvested in PBS+5 mM EDTA and washed twice with cold PBS+0.5% BSA. Cells were then incubated with anti-IL-28RA (R&D Systems; cat #AF5260) at 5 µg antibody per $1\times10^6$ cells in 0.4 ml volume for 30 min, washed 3 times, incubated with FITC conjugated anti-sheep IgG (Abcam; cat #ab6743) at 1:2000 dilution for 30 min, and washed 3 times prior to cell sorting into low, medium, and high IFN-λR1-expressing populations using a BD FACSAria flow cytometer. HepG2, Huh7.5 and WISH cells were seeded at $1\times10^3$ cells/well in 96-well plates. The following day media was replaced with 100 µl/well of IFN-containing media. 4 d post IFN treatment cell density was measured using CellTiter-Glo (Promega) according to the manufacturer's protocol.

Generation of HBV-infected human liver chimeric mice and IFN-λ3 therapy. Human hepatoblasts were isolated from human fetal livers procured from Advanced Bioscience Resources (ABR), Inc. as described. Under anaesthesia with isoflurane, human liver cell suspensions were injected intrasplenically (0.5-1×10$^6$ cells per mouse) into male fah-/-rag2-/-il2rgnull (FRG) obtained from Jackson Laboratories. Starting on the day of transplantation, mice were cycled off the liver protective drug NTBC (Yecuris) as described by others. Human albumin levels in mouse sera were measured by ELISA (Bethyl Laboratories, Montgomery, Tex.). Human-liver chimeric mice were injected intravenously with 100 µL of mouse serum containing 2×10$^8$ DNA copies/ml of HBV originally infected with plasma from a genotype C eAg negative patient. For HBV viral load measurements, DNA from 25 µL of mouse serum was isolated using a DNA extraction kit (QIAamp DNA Blood Mini, Qiagen) and copy number was analyzed by an in-house Taqman assay as described previously. HBsAg (Autobio Diagnostics) levels in mouse serum were determined by CLIA per manufacturers' instructions. Eight mice were randomized for daily treatment for four weeks with intraperitoneal injections of vehicle (15% glycerol in PBS), IFN-λ3 wt or "H11" at 10 ug/kg body weight (2, 3, and 3 mice respectively). Every time point, data were plotted normalized to baseline values and relative to controls. Statistical analysis was performed using the regular two-way ANOVA with Bonferroni multiple comparison post-test in Graphpad Prism.

BIBLIOGRAPHY

Kotenko, S. V. et al. IFN-lambdas mediate antiviral protection through a distinct class II cytokine receptor complex. Nat. Immunol. 4, 69-77 (2003).

Sheppard, P. et al. IL-28, IL-29 and their class II cytokine receptor IL-28R. Nat. Immunol. 4, 63-68 (2003).

Muir, A. J. et al. A randomized phase 2b study of peginterferon lambda-1a for the treatment of chronic HCV infection. J. Hepatol. 61, 1238-1246 (2014).

Nice, T. J. et al. Interferon-A cures persistent murine norovirus infection in the absence of adaptive immunity. Science 347, 269-273 (2015).

Baldridge, M. T. et al. Commensal microbes and interferon-A determine persistence of enteric murine norovirus infection. Science 347, 266-269 (2015).

Lazear, H. M., Nice, T. J. & Diamond, M. S. Interferon-A: Immune Functions at Barrier Surfaces and Beyond. Immunity 43, 15-28 (2015).

Wang, X. et al. Derivation of Phase 3 dosing for peginterferon lambda-1a in chronic hepatitis C, Part 1: Modeling optimal treatment duration and sustained virologic response rates. J. Clin. Pharmacol. 55, 63-72 (2015).

Hruska, M. et al. Derivation of Phase 3 dosing for peginterferon lambda-la in chronic hepatitis C, Part 2: Exposure—response analyses for efficacy and safety variables. J. Clin. Pharmacol. 55, 73-80 (2015).

Commins, S., Steinke, J. W. & Borish, L. The extended IL-10 superfamily: IL-10, IL-19, IL-20, IL-22, IL-24, IL-26, IL-28, and IL-29. J. Allergy Clin. Immunol. 121, 1108-1111 (2008).

Thomas, C. et al. Structural linkage between ligand discrimination and receptor activation by type I interferons. Cell 146, 621-632 (2011).

Jones, B. C., Logsdon, N. J. & Walter, M. R. Structure of IL-22 bound to its high-affinity IL-22R1 chain. Struct. Lond. Engl. 1993 16, 1333-1344 (2008).

Zdanov, A. Structural analysis of cytokines comprising the IL-10 family. Cytokine Growth Factor Rev. 21, 325-330 (2010).

Miknis, Z. J. et al. Crystal structure of human interferon-A1 in complex with its high-affinity receptor interferon-λR1. J. Mol. Biol. 404, 650-664 (2010).

Josephson, K., Logsdon, N. J. & Walter, M. R. Crystal structure of the IL-10/IL-10R1 complex reveals a shared receptor binding site. Immunity 15, 35-46 (2001).

Bleicher, L. et al. Crystal structure of the IL-22/IL-22R1 complex and its implications for the IL-22 signaling mechanism. FEBS Lett. 582, 2985-2992 (2008).

Jones, B. C., Logsdon, N. J. & Walter, M. R. Crystallization and preliminary X-ray diffraction analysis of human IL-22 bound to the extracellular IL-22R1 chain. Acta Crystallograph. Sect. F Struct. Biol. Cryst. Commun. 64, 266-269 (2008).

Yoon, S. I., Logsdon, N. J., Sheikh, F., Donnelly, R. P. & Walter, M. R. Conformational changes mediate interleukin-10 receptor 2 (IL-10R2) binding to IL-10 and assembly of the signaling complex. J. Biol. Chem. 281, 35088-35096 (2006).

Witte, K. et al. Despite IFN-λ receptor expression, blood immune cells, but not keratinocytes or melanocytes, have an impaired response to type III interferons: implications for therapeutic applications of these cytokines. Genes Immun. 10, 702-714 (2009).

Logsdon, N. J. et al. The IL-10R2 binding hot spot on IL-22 is located on the N-terminal helix and is dependent on N-linked glycosylation. J. Mol. Biol. 342, 503-514 (2004).

Wu, P. W. et al. IL-22R, IL-10R2, and IL-22BP binding sites are topologically juxtaposed on adjacent and overlapping surfaces of IL-22. J. Mol. Biol. 382, 1168-1183 (2008).

Yoon, S.-I. et al. Structure and mechanism of receptor sharing by the IL-10R2 common chain. Struct. Lond. Engl. 1993 18, 638-648 (2010).

Gad, H. H. et al. Interferon-lambda is functionally an interferon but structurally related to the interleukin-10 family. J. Biol. Chem. 284, 20869-20875 (2009).

Dellgren, C., Gad, H. H., Hamming, O. J., Melchjorsen, J. & Hartmann, R. Human interferon-lambda3 is a potent member of the type III interferon family. Genes Immun. 10, 125-131 (2009).

24. Ank, N. et al. Lambda interferon (IFN-lambda), a type III IFN, is induced by viruses and IFNs and displays potent antiviral activity against select virus infections in vivo. J. Virol. 80, 4501-4509 (2006).

Spangler, J. B., Moraga, I., Mendoza, J. L. & Garcia, K. C. Insights into cytokine-receptor interactions from cytokine engineering. Annu. Rev. Immunol. 33, 139-167 (2015).

Lasfar, A. et al. Characterization of the mouse IFN-lambda ligand-receptor system: IFN-lambdas exhibit antitumor activity against B16 melanoma. Cancer Res. 66, 4468-4477 (2006).

Moraga, I., et al. Receptor density is key to the alpha2/beta interferon differential activities. Mol. Cell. Biol. 29, 4778-4787 (2009).

Zhou, Z. et al. Type III Interferon (IFN) Induces a Type I IFN-Like Response in a Restricted Subset of Cells through Signaling Pathways Involving both the Jak-STAT Pathway and the Mitogen-Activated Protein Kinases. J. Virol. 81, 7749-7758 (2007).

Grompe, M. et al. Pharmacological correction of neonatal lethal hepatic dysfunction in a murine model of hereditary tyrosinaemia type I. Nat. Genet. 10, 453-460 (1995).

Billerbeck, E. et al. Humanized mice efficiently engrafted with fetal hepatoblasts and syngeneic immune cells develop human monocytes and NK cells. J. Hepatol. 65, 334-343 (2016).

Bissig, K.-D. et al. Human liver chimeric mice provide a model for hepatitis B and C virus infection and treatment. J. Clin. Invest. 120, 924-930 (2010).

Brideau-Andersen, A. D. et al. Directed evolution of gene-shuffled IFN-alpha molecules with activity profiles tailored for treatment of chronic viral diseases. Proc. Natl. Acad. Sci. U.S.A 104, 8269-8274 (2007).

Kalie, E., et al. The stability of the ternary interferon-receptor complex rather than the affinity to the individual subunits dictates differential biological activities. J. Biol. Chem. 283, 32925-32936 (2008).

Lavoie, T. B. et al. Binding and activity of all human alpha interferon subtypes. Cytokine 56, 282-289 (2011).

Piehler, J., Thomas, C., Garcia, K. C. & Schreiber, G. Structural and dynamic determinants of type I interferon receptor assembly and their functional interpretation. Immunol. Rev. 250, 317-334 (2012).

Levin, D. et al. Multifaceted activities of type I interferon are revealed by a receptor antagonist. Sci. Signal. 7, ra50 (2014).

Jaitin, D. A. et al. Inquiring into the differential action of interferons (IFNs): an IFN-alpha2 mutant with enhanced affinity to IFNAR1 is functionally similar to IFN-beta. Mol. Cell. Biol. 26, 1888-1897 (2006).

Kalie, E., et al. An interferon alpha2 mutant optimized by phage display for IFNAR1 binding confers specifically enhanced antitumor activities. J. Biol. Chem. 282, 11602-11611 (2007).

Chan, H. L. Y. et al. Peginterferon lambda for the treatment of HBeAg-positive chronic hepatitis B: A randomized phase 2b study (LIRA-B). J. Hepatol. 64, 1011-1019 (2016).

Ciancio, A. & Rizzetto, M. Chronic hepatitis D at a standstill: where do we go from here? Nat. Rev. Gastroenterol. Hepatol. 11, 68-71 (2014).

Sato, A., Ohtsuki, M., Hata, M., Kobayashi, E. & Murakami, T. Antitumor Activity of IFN-λ in Murine Tumor Models. J. Immunol. 176, 7686-7694 (2006).

Numasaki, M. et al. IL-28 Elicits Antitumor Responses against Murine Fibrosarcoma. J. Immunol. 178, 5086-5098 (2007).

Levin, A. M. et al. Exploiting a natural conformational switch to engineer an interleukin-2 'superkine'. Nature 484, 529-533 (2012).

Walter, T. S. et al. Lysine methylation as a routine rescue strategy for protein crystallization. Struct. Lond. Engl. 1993 14, 1617-1622 (2006).

Pei, J., et al. PROMALS3D: a tool for multiple protein sequence and structure alignments. Nucleic Acids Res. 36, 2295-2300 (2008).

Andrus, L. et al. Expression of paramyxovirus V proteins promotes replication and spread of hepatitis C virus in cultures of primary human fetal liver cells. Hepatol. Baltim. Md 54, 1901-1912 (2011).

Brehm, M. A. et al. Parameters for establishing humanized mouse models to study human immunity: analysis of human hematopoietic stem cell engraftment in three immunodeficient strains of mice bearing the IL2rgamma (null) mutation. Clin. Immunol. Orlando Fla. 135, 84-98 (2010).

Azuma, H. et al. Robust expansion of human hepatocytes in Fah-/-/Rag2-/-/Il2rg-/-mice. Nat. Biotechnol. 25, 903-910 (2007).

Shlomai, A. et al. Modeling host interactions with hepatitis B virus using primary and induced pluripotent stem cell-derived hepatocellular systems. Proc. Natl. Acad. Sci. U.S.A 111, 12193-12198 (2014).

Example 2

Synthekine 2 is a Hybrid Interferon that Dimerizes Type I and Type III IFN Receptors As shown in FIG. 1, a synthekine comprising an IFNλR1 binding sequence (H11DN), and an IFNAR1 binding sequence (IFNWDN2) was generated. The complete synthekine sequence is provided in SEQ ID NO:23. The synthekine thus generated, synthekine 2, is a hybrid Interferon that dimerizes IFNAR1 and IFNAR1 receptors and their respective JAKs.

Shown in FIG. 12C, the Emax of phospho-STAT1 activation by Synthekine 2 is equal to that of type I IFNs, and twice the signal induced by type III IFNs. Error bars represent ±SEM (n=3).

Importantly, as shown in FIG. 12D, synthekine 2 potently induces the anti-proliferative effect, whereas type I IFN, type III IFN or a combination type I and III IFN treatment is ineffective. Error bars represent ±SEM (n=3). Phospho-STAT1 signaling and anti-proliferative assays were performed in Hap1 cells which are naturally responsive to both type I and type III IFNs.

It is also important to note that the combination of type I and type III interferons does not provide this activity unless linked in a hybrid polypeptide such as synthekine 2. The activity and specificity of the synthekine provides a potent agent for anti-proliferative and anti-viral activity, which provides selectivity of action and thus avoids undesirable side effects of Type I interferons.

Methods

In vitro characterization. For measuring gene induction, experiments were performed as described in Example 1. For type I, type III IFNs, and Synthekine 2, and combination type I and III IFNs, pSTAT1 signaling was performed as described except with the modifications that Hap1 cells were detached after IFN treatment by incubating with trypsin (Gibco) for 5 min before fixing and staining.

Anti-proliferative activity of type III IFNs was performed as described in Example 1, with the modifications that for the anti-proliferative activity comparing type I IFN, type III IFNs, Synthekine 2, and combination type I and III IFN, Hap1 cells were plated at 10,000 cells/well in a 96-well format. The following day, the media was replaced with 100 µl/well of IFN-containing media and incubated for 72 hours before measuring cell density.

The examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated hIFNλ variant polypeptide, the variant comprising one or more amino acid substitutions that increase affinity to IL-10Rβ and/or IFNλR1 wherein the one or more amino acid substitutions that increase affinity for IL10Rβ are selected from amino acid substitutions at positions Q26 and E84 and wherein amino acid substitutions that increase affinity for IFNλR1 are selected from H131, T161 and V174, where numbering is relative to SEQ ID NO:3 and wherein the hIFNλ variant polypeptide provides increased STAT1 signaling within a cell expressing an hIFNλ receptor.

2. The isolated hIFNλ variant polypeptide of claim 1, wherein the sequence lacks amino acid residues 1-11 of SEQ ID NO:3.

3. An isolated hIFNλ variant polypeptide of claim 1 selected from the group consisting of SEQ ID NOS: 7, 8, 9, 10, 11, 12, 13, 14, 15,16, 17, 18, 19, and 20 or a biologically active fragment thereof.

4. A pharmaceutical formulation comprising an effective dose of hIFNλ variant polypeptide according to claim 1, and a pharmaceutically acceptable excipient.

5. A method of treating a viral infection in a mammal comprising, administering to the mammal an hIFNλ variant polypeptide as set forth in claim 1, such that infection of cells or replication of virus is inhibited.

6. The method of claim 5, wherein the virus is a hepatitis virus.

7. A method of treating cancer in a mammal comprising, administering to the mammal an hIFNλ variant polypeptide as set forth in claim 1, such that growth or replication of the cancer is inhibited.

8. The method of claim 7, wherein the cancer cells express a receptor for hIFN-λ.

9. The isolated hIFNλ variant polypeptide of claim 1, wherein the one or more amino acid substitutions that increase affinity to IL-10R are selected from one or both of Q26R and E84D, where numbering is relative to SEQ ID NO:3.

10. The isolated hIFNλ variant polypeptide of claim 9, wherein the one or more amino acid substitutions that increase affinity to IFNλR1 is a substitution at T161, where numbering is relative to SEQ ID NO: 3.

11. The isolated hIFNλ variant polypeptide of claim 9, wherein comprising the amino acid substitutions Q26R, E84D, and T161A, where numbering is relative to SEQ ID NO: 3.

12. The isolated hIFNλ variant polypeptide of claim 9, further comprising one or more amino acid substitutions at H131, T161 and V174, where numbering is relative to SEQ ID NO: 3.

13. The isolated hIFNλ variant polypeptide of claim 12, wherein the one or more amino acid substitutions at H131, T161, and V174 comprise a substitution of one or more of H131R, T161A, and V174E.

* * * * *